United States Patent
Deyle et al.

(10) Patent No.: US 10,975,123 B2
(45) Date of Patent: Apr. 13, 2021

(54) MUTANT AKT-SPECIFIC CAPTURE AGENTS, COMPOSITIONS, AND METHODS OF USING AND MAKING

(71) Applicant: California Institute of Technology, Pasadena, CA (US)

(72) Inventors: Kaycie Deyle, Sylmar, CA (US); Blake Farrow, Pasadena, CA (US); James R. Heath, South Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 0 days.

(21) Appl. No.: 15/680,171

(22) Filed: Aug. 17, 2017

(65) Prior Publication Data

US 2018/0072772 A1 Mar. 15, 2018

Related U.S. Application Data

(63) Continuation of application No. 14/704,865, filed on May 5, 2015, now abandoned.

(60) Provisional application No. 61/988,839, filed on May 5, 2014.

(51) Int. Cl.
| | |
|---|---|
| A61K 38/00 | (2006.01) |
| C07K 7/06 | (2006.01) |
| G01N 33/573 | (2006.01) |
| C07K 7/00 | (2006.01) |
| C12N 9/12 | (2006.01) |
| G01N 33/574 | (2006.01) |
| C07K 14/00 | (2006.01) |

(52) U.S. Cl.
CPC .............. *C07K 7/06* (2013.01); *C07K 7/00* (2013.01); *C07K 14/001* (2013.01); *C12N 9/1205* (2013.01); *G01N 33/573* (2013.01); *G01N 33/574* (2013.01); *A61K 38/00* (2013.01); *G01N 2333/912* (2013.01)

(58) Field of Classification Search
None
See application file for complete search history.

(56) References Cited

U.S. PATENT DOCUMENTS

| | | |
|---|---|---|
| 4,899,755 A | 2/1990 | Lauffer et al. |
| 5,021,556 A | 6/1991 | Srinivasan |
| 5,075,099 A | 12/1991 | Srinivasan et al. |
| 5,118,797 A | 6/1992 | Jurisson et al. |
| 5,183,653 A | 2/1993 | Linder et al. |
| 5,364,613 A | 11/1994 | Sieving et al. |
| 5,367,080 A | 11/1994 | Toner et al. |
| 5,387,409 A | 2/1995 | Nunn et al. |
| 5,474,756 A | 12/1995 | Tweedle et al. |
| 5,608,110 A | 3/1997 | Ramalingam et al. |
| 5,656,254 A | 8/1997 | Ramalingam et al. |
| 5,662,885 A | 9/1997 | Pollak et al. |
| 5,665,329 A | 9/1997 | Ramalingam et al. |
| 5,688,487 A | 11/1997 | Linder et al. |
| 5,720,934 A | 2/1998 | Dean et al. |
| 5,780,006 A | 7/1998 | Pollak et al. |
| 5,846,519 A | 12/1998 | Tweedle et al. |
| 5,849,261 A | 12/1998 | Dean et al. |
| 5,879,658 A | 3/1999 | Dean et al. |
| 5,886,142 A | 3/1999 | Thakur et al. |
| 5,976,495 A | 11/1999 | Pollak et al. |
| 6,093,382 A | 7/2000 | Wedeking et al. |
| 6,143,274 A | 11/2000 | Tweedle et al. |
| 2010/0009896 A1 | 1/2010 | Agnew et al. |

FOREIGN PATENT DOCUMENTS

| | | |
|---|---|---|
| WO | 8606605 A1 | 11/1986 |
| WO | 9103200 A1 | 3/1991 |
| WO | 9503280 A1 | 2/1995 |
| WO | 9506633 A1 | 3/1995 |
| WO | 9528179 A1 | 10/1995 |
| WO | 9528967 A1 | 11/1995 |
| WO | 9603427 A1 | 2/1996 |
| WO | 9623526 A2 | 8/1996 |
| WO | 9736619 A2 | 10/1997 |
| WO | 9818496 A2 | 5/1998 |
| WO | 9818497 A2 | 5/1998 |
| WO | 9846612 A1 | 10/1998 |
| WO | 9852618 A1 | 11/1998 |
| WO | 9917809 A2 | 4/1999 |
| WO | 2009155420 A1 | 12/2009 |
| WO | 2012106671 A1 | 8/2012 |
| WO | 2013009869 A2 | 1/2013 |
| WO | 2013033561 A1 | 3/2013 |
| WO | 2014074907 A1 | 5/2014 |
| WO | 2015038933 A1 | 3/2015 |

OTHER PUBLICATIONS

Agnew et al. (Jan. 6, 2010) "Rapid Construction of Protein Capture Agents with Chemically Designed Stability and Antibody-Like Recognition Properties (Thesis)," California Institute of Technology. 1-187.

Deyle et al. (Apr. 6, 2015) "A Protein-Targeting Strategy Used to Develop a Selective Inhibitor of the E17K Point Mutation in the PH Domain of AKT-1," Nature Chemistry. 7:455-462.

Deyle et al. (Apr. 6-10, 2013) Proceedings: AACR 104th Annual Meeting 2013; Washington, DC.

Jo et al. (Apr. 4, 2011) "Deactivation of Akt by a small molecule inhibitor targeting pleckstrin homology domain and facilitating Akt ubiquitination," Proceedings of the National Academy of Sciences. 108(16):6486-6491.

Kim et al. (Mar. 12, 2010) "A Small Molecule Inhibits Akt through Direct Binding to Akt and Preventing Akt Membrane Translocation," Journal of Biological Chemistry. 285(11):8383-8394.

(Continued)

*Primary Examiner* — Jeanette M Lieb
(74) *Attorney, Agent, or Firm* — Pabst Patent Group LLP

(57) ABSTRACT

The present application provides stable peptide-based Akt capture agents and methods of use as detection and diagnosis agents and in the treatment of diseases and disorders. The application further provides methods of manufacturing Akt capture agents using iterative on-bead in situ click chemistry.

22 Claims, 31 Drawing Sheets

Specification includes a Sequence Listing.

(56) References Cited

OTHER PUBLICATIONS

Lin et al. (Sep. 2011) "Inhibition of HIV-1 Tat-mediated transcription by a coumarin derivative, BPRHIV001, through the Akt pathway," Journal of Virology. 85(17):9114-9126.
Millward et al. (2011) "Iterative in situ click chemistry assembles a branched capture agent and allosteric inhibitor for Akt1," Journal of the American Chemical Society. 133(45):18280-18288.
Nag et al. (2013) "A Chemical Epitope-Targeting Strategy for Protein Capture Agents: The Serine 474 Epitope of the Kinase Akt2," Angewandte Chemie International Edition. 52(52):13975-13979.
Rohde (May 27, 2009) "Developing High-Affinity Protein Capture Agents and Nanotechnology-Based Platforms for In Vitro Diagnostics (Thesis)," California Institute of Technology. 1-96.
Agnew et al. (2009) "Iterative In Situ Click Chemistry Creates Antibody-like Protein-Capture Agents," Angewandte Chemie International Edition. 48(27):4944-4948.
Alexander et al. (1998) "Intracranial black-blood MR angiography with high-resolution 3D fast spin echo," Magnetic Resonance in Medicine. 40(2):298-310.
Altschul et al. (1997) "Gapped BLAST and PSI-BLAST: a new generation of protein database search programs," Nucleic acids research. 25(17):3389-3402.
Bundgaard (ed.) (1985) Design of Prodrugs. Elsevier Publishing Company, Amsterdam. pp. 7-9, 21-24.
Capper et al. (2009) "Monoclonal antibody specific for IDH1 R132H mutation," Acta neuropathological. 118(5):599-601.
Capper et al. (2011) "Assessment of BRAF V600E mutation status by immunohistochemistry with a mutation-specific monoclonal antibody," Acta neuropathological. 122(1):11-19.
Carpten et al. (2007) "A transforming mutation in the pleckstrin homology domain of AKT1 in cancer," Nature. 448(7152):439-444.
Chong et al. (2013) "The quest to overcome resistance to EGFR-targeted therapies in cancer," Nature medicine. 19(11):1389-1400.
Claverie et al. (1993) "Information enhancement methods for large scale sequence analysis," Comput. Chem. 17:191-201.
Coin et al. (2007) "Solid-phase peptide synthesis: from standard procedures to the synthesis of difficult sequences," Nature protocols. 2(12):3247-3256.
Edelman et al. (1990) "Extracranial carotid arteries: evaluation with 'black blood' MR angiography," Radiology. 177(1)45-50.
Fan et al. (2014) "Rapid and reversible knockdown of endogenous proteins by peptide-directed lysosomal degradation," Nature neuroscience. 17(3):471-480.
Farrow et al. (2013) "A chemically synthesized capture agent enables the selective, sensitive, and robust electrochemical detection of anthrax protective antigen," ACS nano. 7(10):9452-9460.
Goodrich et al. (1996) "A Quantitative Study of Ramped Radio Frequency, Magnetization Transfer, and Slab Thickness in Three-Dimensional Time-of-Flight Magnetic Resonance Angiography in a Patient Population," Invest. Radiol. 31:323-332.
Hines et al. (2013) "Posttranslational protein knockdown coupled to receptor tyrosine kinase activation with phosphoPROTACs," Proceedings of the National Academy of Sciences. 110(22):8942-8947.
Hiromura et al. (2004) "Inhibition of Akt kinase activity by a peptide spanning the βA strand of the proto-oncogene TCL1," Journal of Biological Chemistry. 279(51):53407-53418.
Itoh et al. (2010) "Protein Knockdown Using Methyl Bestatin-Ligand Hybrid Molecules: Design and Synthesis of Inducers of Ubiquitination-Mediated Degradation of Cellular Retinoic Acid-Binding Proteins," J. Am. Chem. Soc. 132:5820-5826.
Iwata et al. (2000) "A new, convenient method for the preparation of 4-[18F]fluorobenzyl halides," Applied Radiation and Isotopes. 52:87-92.
Kodadek et al. (2004) "Synthetic molecules as antibody replacements," Accounts of Chemical Research. 37:711-718.
Lee et al. (2010) "Accurate MALDI-TOF/TOF Sequencing of One-Bead-One-Compound Peptide Libraries with Application to the Identification of Multiligand Protein Affinity Agents Using in Situ Click Chemistry Screening," Analytical chemistry. 82(2):672-679.
Liu et al. (1999) "99mTc-Labeled Small Peptides as Diagnostic Radiopharmaceuticals," Chem. Rev. 99:2235-2268.
Long et al. (2012) "Inhibitor mediated protein degradation," Chemistry & biology. 19(5):629-637.
Mahadevan et al. (2008) "Discovery of a novel class of AKT pleckstrin homology domain inhibitors," Molecular cancer therapeutics. 7(9):2621-2632.
Marschall et al. (2011) "Targeting antibodies to the cytoplasm," MAbs. 3(1):3-16.
Myers et al. (1988) "Optimal alignments in linear space," Computer Appl. Biol. Sci. 4:11-17.
Pashkova et al. (2004) "Coumarin Tags for Improved Analysis of Peptides by MALDI-TOF MS and MS/MS. 1. Enhancement in MALDI MS Signal Intensities," Analytical Chemistry. 76:4550-4557.
Pfeilsticker et al. (2013) "A cocktail of thermally stable, chemically synthesized capture agents for the efficient detection of anti-Gp41 antibodies from human sera," PloS one. 8(10):e76224.
Poethko et al. (2004) "Two-step methodology for high-yield routine radiohalogenation of peptides: 18F-labeled RGD and octreotide analogs," Journal of nuclear medicine. 45(5):892-902.
Rondon et al. (1997) "Intracellular Antibodies (Intrabodies) for Gene Therapy of Infectious Diseases," Annual Review of Microbiology. 51(1):257-283.
Rusling et al. (2010) "Measurement of biomarker proteins for point-of-care early detection and monitoring of cancer," Analyst. 135(10):2496-2511.
Sakamoto et al. (2001) "Protacs: chimeric molecules that target proteins to the Skp1-Cullin-F box complex for ubiquitination and degradation," Proceedings of the National Academy of Sciences. 98(15):8554-8559.
Sakamoto et al. (2003) "Development of Protacs to target cancer-promoting proteins for ubiquitination and degradation," Molecular & Cellular Proteomics. 2(12):1350-1358.
Schneekloth et al. (2008) "Targeted intracellular protein degradation induced by a small molecule: En route to chemical proteomics," Bioorganic & medicinal chemistry letters. 18(22):5904-5908.
Schottelius et al. (2004) "First 18F-labeled tracer suitable for routine clinical imaging of sst receptor-expressing tumors using positron emission tomography," Clinical Cancer Research. 10(11):3593-3606.
Sjin et al. (2014) "In vitro and in vivo characterization of irreversible mutant-selective EGFR inhibitors that are wild-type sparing," Molecular cancer therapeutics. 13(6):1468-1479.
Tae et al. (2012) "Identification of hydrophobic tags for the degradation of stabilize proteins," ChemBioChem. 13(4):538-541.
Testa et al. (2005) "AKT signaling in normal and malignant cells," Oncogene. 24(50):7391-7393.
Tsukiji et al. (2009) "Ligand-directed 20 tosyl chemistry for protein labeling in vivo," Nat. Chem. Biol. 5:341-343.
Vivanco et al. (2002) "The phosphatidylinositol 3-kinase-AKT pathway in human cancer," Nature Reviews Cancer. 2(7):489-501.
Wilson et al. (1990) "Reductive amination of [18F] fluorobenzaldehydes: Radiosyntheses of [2-18F]-and [4-18F] fluorodexetimides," Journal of Labelled Compounds and Radiopharmaceuticals. 28(10):1189-1199.
Wootton et al. (1993) "Statistics of local complexity in amino acid sequences and sequence databases," Computers & chemistry. 17(2):149-163.
Yu et al. (2009) "Mutation-specific antibodies for the detection of EGFR mutations in non-small-cell lung cancer," Clinical Cancer Research. 15(9):3023-3028.
International Preliminary Report on Patentability corresponding to International Patent Application No. PCT/US2015/029145, dated Nov. 8, 2016, 9 pages.
International Search Report corresponding to International Patent Application No. PCT/US2015/029145, dated Aug. 26, 2015, 16 pages.

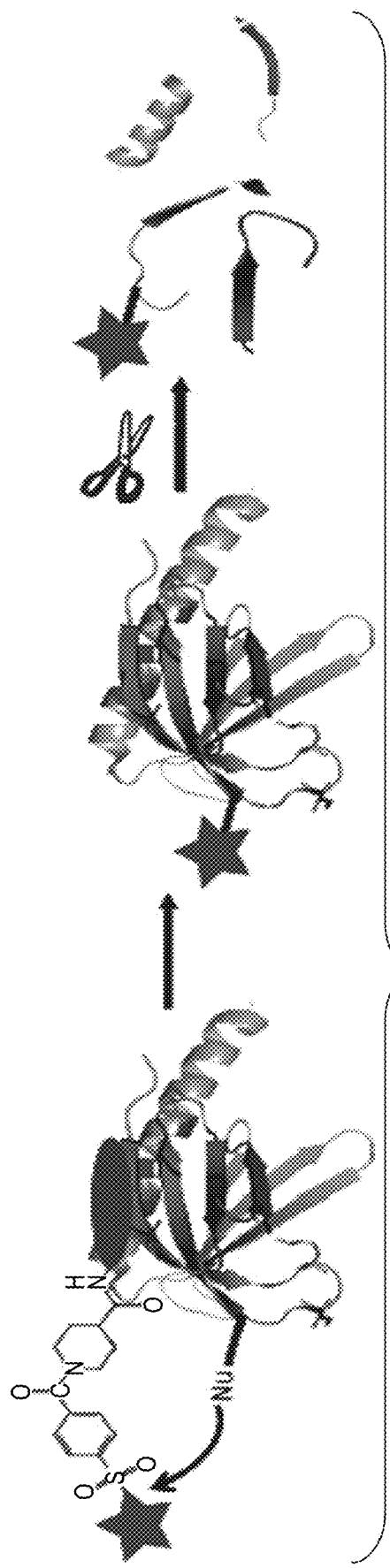
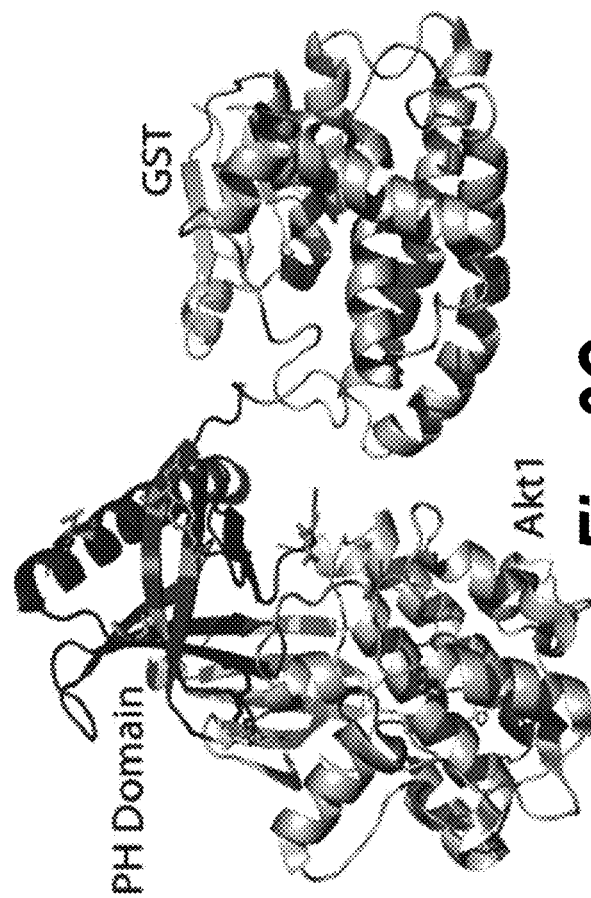
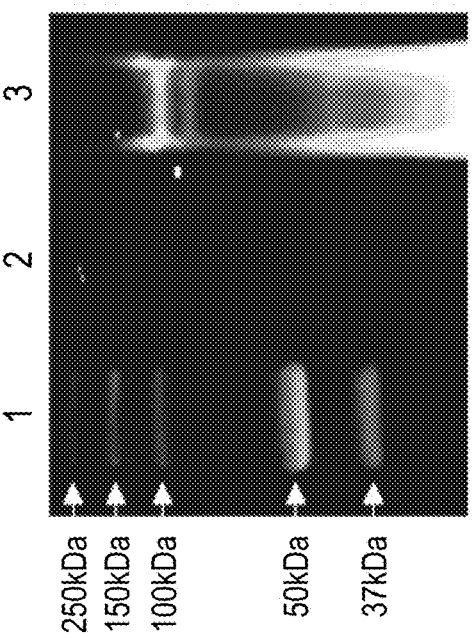
Fig. 3A
Fig. 3B
Fig. 3C

* PH Domain bound to PIP3

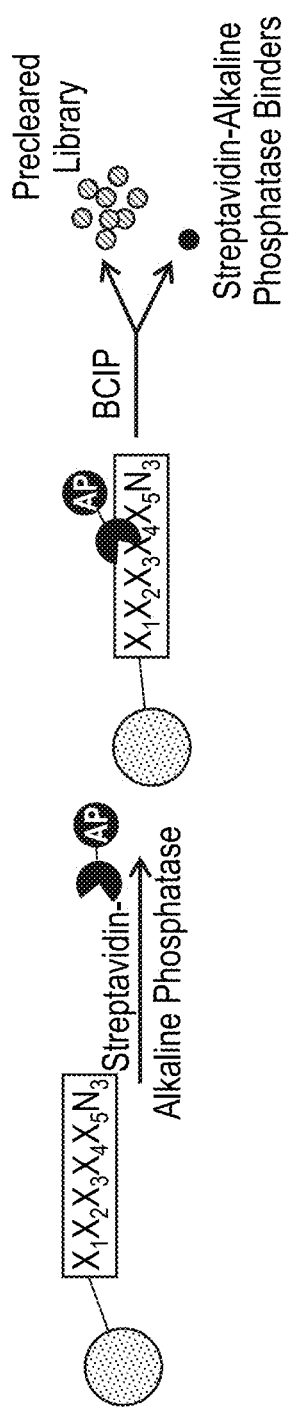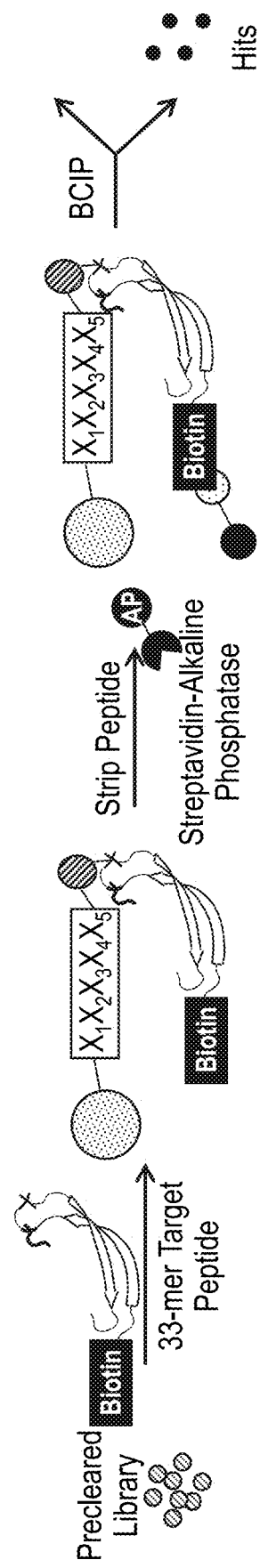
Fig. 9A
Fig. 9B

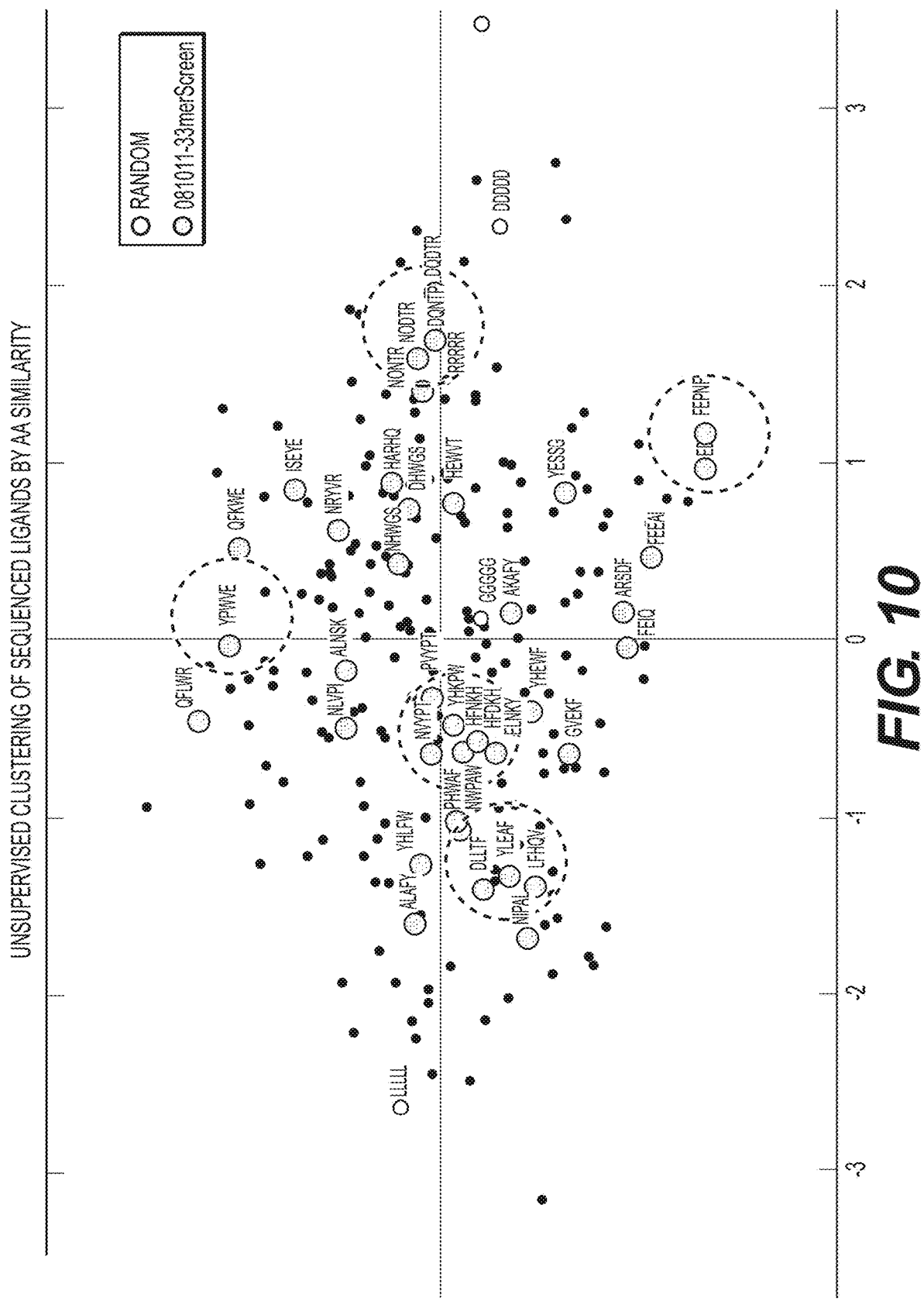

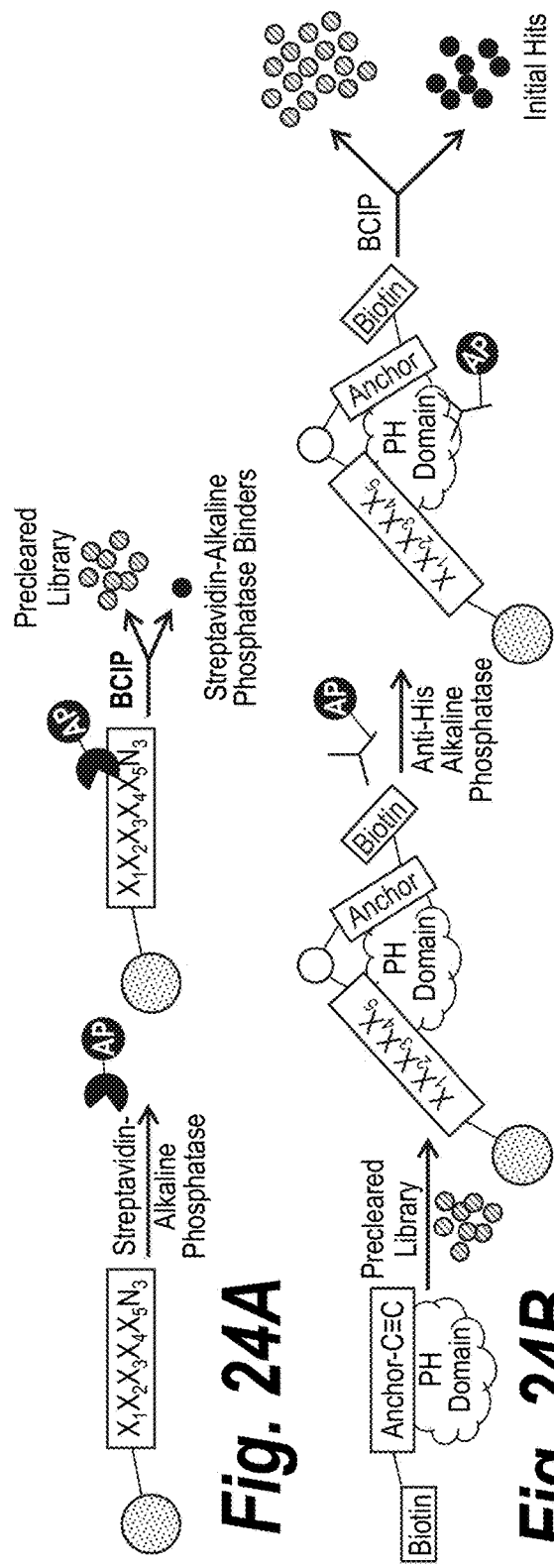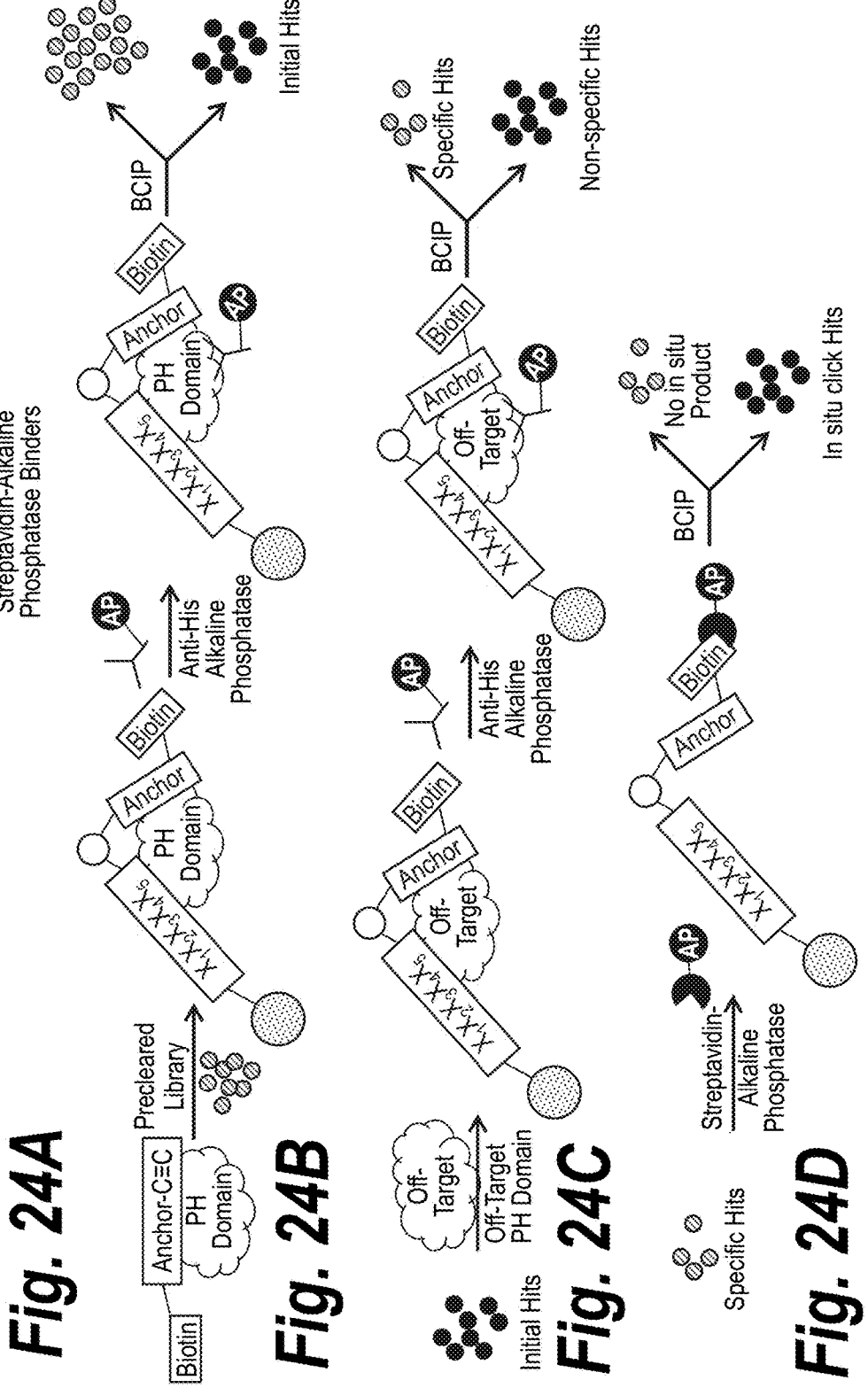

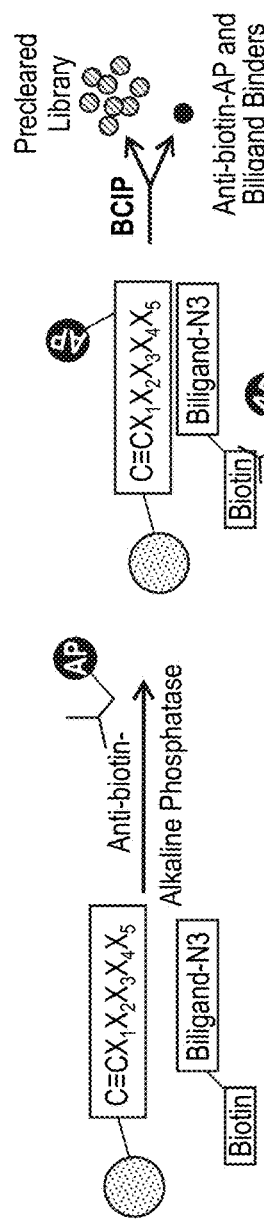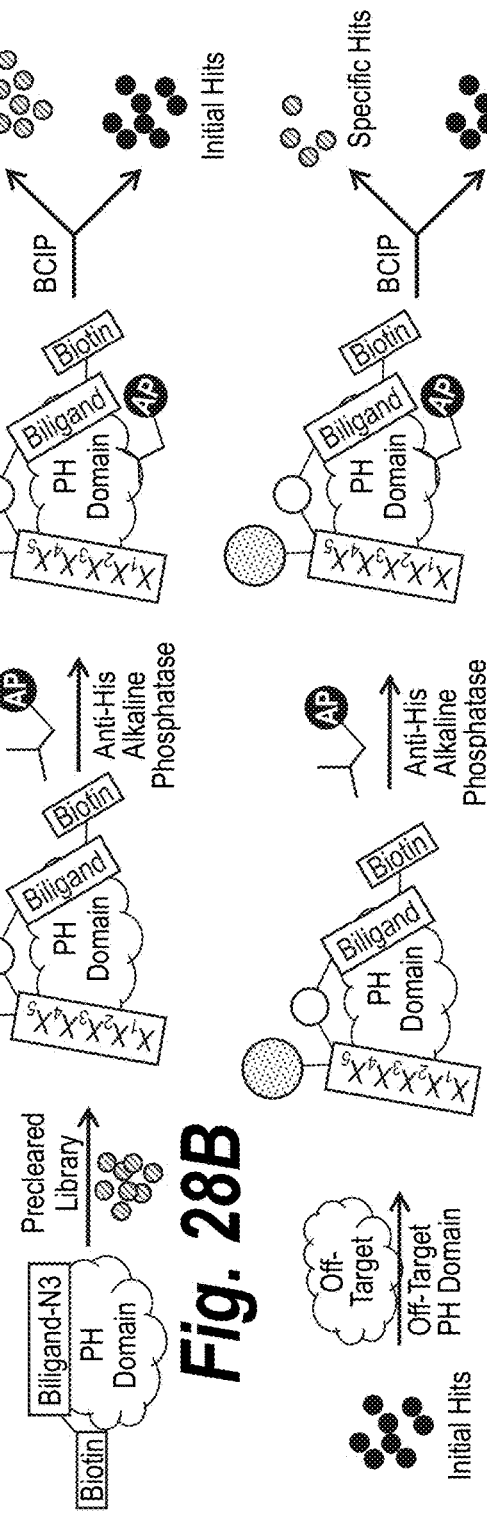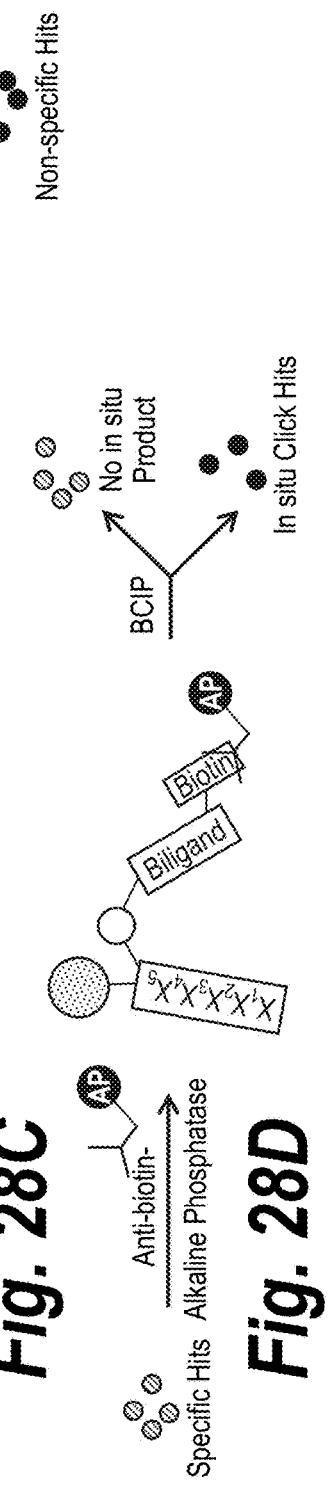

MUTANT AKT-SPECIFIC CAPTURE AGENTS, COMPOSITIONS, AND METHODS OF USING AND MAKING

RELATED APPLICATIONS

This application is a continuation of U.S. patent application Ser. No. 14/704,865, filed on May 5, 2015, which claims priority from U.S. Provisional Patent Application No. 61/988,839, filed on May 5, 2014, the contents of both of which are incorporated herein by reference.

STATEMENT OF GOVERNMENT INTEREST

This invention was made with government support under Grant No. W911NF-09-D-0001 awarded by the U.S. Army. The government has certain rights in the invention.

REFERENCE TO A SEQUENCE LISTING

The instant application contains a Sequence Listing which has been submitted in ASCII format via EFS-Web and is hereby incorporated by reference in its entirety.

BACKGROUND

Ligands that selectively bind to proteins with single amino acid point mutations are becoming increasingly important for both diagnostics and therapeutics. In a diagnostic setting, such binders can be used to assay for the mutant protein within diseased tissues, and thus potentially provide clinical guidance for treatment decisions. A more ambitious application is the development of drugs that can selectively inhibit mutant proteins, and thus avoid those toxic side-effects that stem from the inhibition of the wild-type (WT) variants that reside in non-diseased tissues.

A challenge of drug targeting a single point mutation is that the mutation may not be directly associated with a binding pocket. The presence of a binding pocket is traditionally required for small molecule inhibitor development. This requirement does not hold for antibodies and, in fact, several examples of monoclonal antibodies directed against epitopes containing single amino acid mutations do exist. However, antibodies do not readily enter the living cells that can harbor the mutated proteins, and so mutation-selective antibodies are typically only used as diagnostic reagents for staining fixed cells or tissues. Thus, there is a need for an approach that can identify small molecules that can be generally targeted against epitopes containing single amino acid point mutations, and which can potentially be developed into cell-penetrant inhibitors.

Akt1 kinase plays a critical role in the PI3K signaling pathway—the activation of which is closely linked to tumor development and cancer cell survival. The recently discovered E17K mutation in the Pleckstrin Homology Domain (PHD) of Akt1 results in an increased affinity for the phosphatidylinositol (3,4,5)-trisphosphate (PIP3) substrate at the cell membrane. Consequently, this deregulated recruitment of Akt1 to the cell membrane causes constitutive activation of the PI3K pathway, which has been shown to induce leukemia in mice. The oncogenic properties of the driving E17K single point mutation make it a target for both detection and inhibition.

SUMMARY

The present disclosure relates to chemically synthesized capture agents (called protein-catalyzed capture agents, or PCC Agents) that are designed to bind Akt, methods for making said capture agents using iterative in situ click chemistry, methods for using said capture agents to detect Akt, and assays employing said methods.

In one aspect, provided herein is a stable, synthetic capture agent that specifically binds to Akt1, wherein the capture agent comprises a designed anchor ligand, a designed secondary ligand, a designed tertiary ligand, and optionally a designed quaternary ligand, and wherein the ligands selectively bind Akt1 with a mutation of glutamate to lysine at position 17 of the pleckstrin homology domain (E17K Akt1) over wild-type Akt1

In another aspect, provided herein is a composition comprising one or more synthetic capture agents of the invention that specifically binds E17K Akt1.

In another aspect, provided herein is a method for detecting E17K Akt1 in a biological sample, comprising the step of treating the biological sample with one or more capture agents of the invention.

In another aspect, provided herein is method of diagnosing cancer in a subject, the method comprising the steps of: a) administering to the subject one or more capture agents of the invention, wherein each capture agent is linked to a detectable moiety; and b) detecting the moiety linked to each capture agent; wherein detection of the moiety diagnoses cancer in the subject.

Anchor Ligand

The secondary ligand was selected via an in situ click screen from a large (e.g., $10^6$ element) one-bead-one-compound (OBOC) peptide library. In one embodiment of the capture agent, the anchor ligand comprises the sequence yleaf (SEQ ID NO: 43). In another embodiment, the anchor ligand comprises the sequence (D-Pra)-yleaf (SEQ ID NO: 43). In some embodiments, the anchor ligand is chemically modified to comprise a detection label (e.g., biotin, biotin-PEG, DOTA, NOTA and the like).

Secondary Ligand

Secondary ligands were selected via an in situ click screen from a large (e.g., $10^6$ element) one-bead-one-compound (OBOC) peptide library. In some embodiments, the secondary ligand consists of 5 amino acids. In one embodiment, the peptide library is comprehensive for 5-mers, with a 6th amino acid at the N-terminus presenting azide functionality. In one embodiment, the library comprises non-natural (D) stereoisomers of the 20 natural amino acids, excluding cysteine and methionine. In some embodiments, the secondary ligand comprises a sequence selected from the sequences of Table 3. In a particular embodiment, the secondary ligand is yksy (SEQ ID NO: 76).

Tertiary Ligand

Tertiary ligands were selected via an in situ click screen from a large (e.g., $10^6$ element) one-bead-one-compound (OBOC) peptide library. In one embodiment, the tertiary ligand clicks to the N-terminus of a biligand. In another embodiment, the tertiary ligand clicks to the C-terminus of a biligand. In one embodiment, the tertiary ligand comprises a sequence selected from the sequences of Table 4.

In one embodiment, the tertiary ligand clicks to the N-terminus of an anchor sequence and comprises the sequence ivdae (SEQ ID NO: 78).

Quaternary Ligand

The quaternary ligands, if present, are selected via an in situ click screen from a large (e.g., $10^6$ element) one-bead-one-compound (OBOC) peptide library. Triazole Linkage In one embodiment of the capture agent, the anchor ligand and secondary ligand are linked together via a 1,4-substituted-1,2,3-triazole residue (Tz4). In another embodiment, the secondary ligand and the tertiary ligand are linked together via a 1,4-substituted-1,2,3-triazole residue (Tz4). In yet another embodiment, the tertiary ligand and the quarternary ligand are linked together via a 1,4-substituted-1,2,3-triazole residue (Tz4). In yet another embodiment, the anchor ligand and secondary ligand are linked together via a 1,4-substituted-1,2,3-triazole residue, and the secondary ligand and the tertiary ligand are linked together via a 1,4-substituted-1,2,3-triazole residue. In yet another embodiment, the anchor ligand and secondary ligand are linked together via a 1,4-substituted-1,2,3-triazole residue, the secondary ligand and the tertiary ligand are linked together via a 1,4-substituted-1,2,3-triazole residue and the tertiary ligand and the quarternary ligand are linked together via a 1,4-substituted-1,2,3-triazole residue.

Protein Target (E17K Akt1-Peptide)

The anchor ligand and higher-order ligand candidates were screened against a chemically-modified peptide comprising of the sequence of the target epitope, i.e., the 33 amino acid long N-terminal fragment of the pleckstrin homology domain of E17K Akt1 (MSDVAIVKEG-WLKKRGKY[Pra]KTWRPRYFLLKNDG) (SEQ ID NO: 1).

In one embodiment, the complex comprises an alkyne containing propargylglycine residue as an in situ click anchor site and a biotin group as an assay handle.

Biligands, Triligands and Tetraligands

In one embodiment, a capture agent of the invention is a biligand, comprising an anchor ligand and a secondary ligand.

In another embodiment, a capture agent of the invention is a triligand, comprising an anchor ligand, a secondary ligand and a tertiary ligand. Non-limiting examples of triligand capture agents of the invention are disclosed in FIG. 5b.

In still another embodiment, a capture agent of the invention is a tetraligand, comprising an anchor ligand, a secondary ligand, a tertiary ligand and a quaternary ligand.

In one embodiment, the capture agent binds to E17K Akt1.

Properties

In certain embodiments, the E17K Akt1 capture agents provided herein are stable across a wide range of temperatures, pH's, storage times, storage conditions, and reaction conditions, and in certain embodiments the capture agents are more stable than a comparable antibody or biologic. In certain embodiments, the capture agents are stable in storage as a lyophilized powder. In certain embodiment, the capture agents are stable in storage at a temperature of about −80° C. to about 60° C. In certain embodiments, the capture agents are stable at room temperature. In certain embodiments, the capture agents are stable in human serum for at least 24 hours. In certain embodiments, the capture agents are stable at a pH in the range of about 3 to about 12. In certain embodiments, the capture agents are stable as a powder for two months at a temperature of about 60° C.

Detectable Labels

In some embodiments, the capture agent is labeled with a label selected from the group consisting of biotin, copper-DOTA, biotin-PEG3, aminooxyacetate, $^{19}$FB, $^{18}$FB, FITC-PEG3, fluorescein and fluorescein derivatives (e.g., 5-carboxy fluorescein). In other embodiments, the capture agent is labeled with the detectable moiety consisting of $^{64}$Cu DOTA, $^{68}$Ga DOTA, $^{18}$F, $^{64}$Cu, $^{68}$Ga, $^{89}$Zr, $^{124}$I, $^{86}$Y, $^{94m}$Tc, $^{110m}$In, $^{11}$C and $^{76}$Br. In other embodiments, the label is a fluorescent label. In a particular embodiment, the detectable label is $^{18}$F.

Cell Penetrating Peptides

In some embodiments, the capture agent comprises a cell penetrating peptide. These cell penetrating peptides allow the capture agents to enter eukaryotic cells. In certain embodiments, these eukaryotic cells are mammalian cells. In specific embodiments, these mammalian cells are human cells. In certain embodiments, the cell penetrating peptide is an HIV-TAT sequence. In certain embodiments, the HIV-TAT sequence is a sequence at least 90% identical to $H_2$N-GRKKRRQRRRPPQQ-CONH$_2$ (SEQ ID NO: 2) or a fragment thereof. Other cell penetrating peptides that can be used include penetratin, SynB1, SynB2, PTD-4, PTD-5, FHV Coar (35-49), BMV Gag (7-25), HTLV-II Rex (4-16), D-Tat, R9-Tat ("R9" disclosed as SEQ ID NO: 3), transportan, MAP, SBP, FBP, MPG, Pep-1, Pep-2, polyarginines, or polylysines. Any sequence at least 90% identical to any of the cell penetrating peptides or fragments thereof may be used.

METHODS AND USES

Provided herein is a method of inhibiting E17K Akt1 signaling in a subject comprising administering to the subject a capture agent of the invention. In certain embodiments, methods are provided for inhibiting E17K Akt1 activity in vivo or in vitro using a E17K Akt1 capture agent as provided herein. In certain embodiments, inhibition of E17K Akt1 activity results in an effective decrease in E17K Akt1 levels and/or a change in E17K Akt1 conformation. In certain embodiments, inhibition of E17K Akt1 activity results in an effective decrease in membrane-bound E17K, and a concomitant decrease in phosphorylated Akt1.

Also provided herein is a method of treating a condition associated with increased E17K Akt1 expression and/or activity in a subject in need thereof, comprising administering a therapeutically effective amount of a capture agent as described herein. In one embodiment, the condition associated with increased E17K Akt1 expression and/or activity is cancer. In one embodiment, the cancer is ovarian cancer.

Provided is a method of diagnosing cancer in a subject, the method comprising the steps of:
a) administering one or more capture agents of the invention to the subject, wherein each capture agent is linked to a detectable moiety; and
b) detecting the moiety linked to each capture agent; wherein detection of the moiety diagnoses cancer in the subject.

Also provided is a method of detecting cancer in a subject, comprising the step of contacting a biological sample from the subject with one or more capture agents of the invention.

Also provided is a method of detecting cancer in a biological sample using an immunoassay, wherein the immunoassay utilizes a capture agent as described herein, and wherein said capture agent replaces an antibody or its equivalent in the immunoassay. In certain embodiments, methods are provided for identifying, detecting, quantifying, or separating E17K Akt1 in a biological sample using the capture agents as described herein. In one embodiment of the method, the immunoassay is selected from the group of Western blot, pull-down assay, dot blot, and ELISA.

Also provided is a method of monitoring treatment of a subject receiving cancer-directed therapy comprising the steps of:
a) contacting a first biological sample from the subject with one or more capture agents of the invention, wherein each capture agent is linked to a detectable moiety;

b) detecting the moiety linked to the capture agent, wherein the capture agent is bound to E17KAkt1;
c) administering a treatment for the cancer associated with increased E17K Akt1 expression to the subject;
d) contacting a second biological sample from the subject one or more capture agents of the invention, wherein each capture agent is linked to a detectable moiety; and
e) detecting the moiety linked to the capture agent, wherein the capture agent is bound to E17KAkt1; and
(f) comparing the level of moiety detected in step (b) with the level of moiety detected in step (d).

In one embodiment, if less of the moiety is detected in step (e) than in step (b), the treatment is improving cancer in the subject.

Also provided herein is a method of monitoring treatment of a subject receiving E17K Akt1-directed therapy comprising administering to the patient a small-molecule positron-emission-tomography ligand (PET ligand) that is bound to the E17K Akt1 capture agent, as described herein, on or near a E17K Akt1-expressing cancer in the subject.

Also provided herein is the use of one or more E17K Akt1 capture agents of the invention for use in preparing a medicament for treating a condition associated with increased E17K Akt1 expression and/or activity in a subject in need thereof.

Kits

Provided herein in certain embodiments are kits comprising one or more capture agents of the invention. In certain embodiments, these kits may be used for identifying, detecting, quantifying, and/or separating E17KAkt1, and in certain embodiments the kits may be used in the diagnosis and/or staging of a conditions associated with the presence of E17K Akt1. In certain embodiments, a kit as provided herein comprises: (a) a substrate comprising an adsorbent thereon, wherein the adsorbent is suitable for binding E17K Akt1, and (b) a washing solution or instructions for making a washing solution, wherein the combination of the adsorbent and the washing solution allows detection of E17K Akt1. In other embodiments, the kits provided herein may be used in the treatment of a condition associated with the presence of E17K Akt1.

In certain embodiments, a kit may further comprise instructions for suitable operational parameters in the form of a label or a separate insert. For example, the kit may have standard instructions informing a consumer/kit user how to wash the probe after a sample of plasma or other tissue sample is contacted on the probe.

In certain embodiments, a kit as comprises: (a) one or more capture agents that specifically bind E17K Akt1; and (b) a detection reagent. Such kits can be prepared from the materials described herein.

The kits provided herein may optionally comprise a standard or control information, and/or a control amount of material, so that the test sample can be compared with the control information standard and/or control amount to determine if the test amount of E17K Akt1 detected in a sample is an amount consistent with a diagnosis of a particular condition.

Synthesis of Capture Agents

Provided herein are methods for making (i.e., synthesizing) the E17K Akt1 capture agents of the invention. In one embodiment, the method comprises the steps of:
(a) providing an anchor ligand;
(b) identifying a secondary ligand by the following steps:
    (i) preparing an anchor ligand selection block comprising the anchor ligand and an azido group or an alkynyl group;
    (ii) preparing a plurality of candidate peptides to select a secondary ligand for the target protein, the plurality of peptides comprising an azido group, or an alkynyl group, if the anchor ligand selection block comprises an alkynyl group, or an azido group, respectively;
    (iii) contacting the anchor ligand selection block and the plurality of peptides with the target protein (e.g., an epitope of E17K Akt1);
    (iv) providing a capture agent biligand by forming a disubstituted 1,2,3-triazole linkage between the anchor ligand selection block and the secondary ligand wherein the azido group and alkynyl group of the anchor ligand selection block and the secondary ligand are brought in close proximity by binding to the target protein;
    (v) selecting the capture agent biligand that has an affinity with the target protein; and
    (vi) sequencing the secondary ligand; and optionally
(c) identifying a tertiary ligand by the following steps:
    (i) preparing a biligand selection block comprising an azido group or an alkynyl group; and
    (ii) repeating steps (b)(ii) to (b)(vi) using a third plurality, fourth plurality, etc., of candidate peptides until a capture agent having desired binding affinity to the target protein is obtained; and optionally
(d) identifying a quarternary ligand and, optionally, additional ligands by the following steps:
    (i) preparing a triligand selection block comprising an azido group or an alkynyl group; and
    (ii) repeating steps (c)(ii) to (c)(vi) using a fourth plurality, fifth plurality, etc., of candidate peptides until a capture agent having desired binding affinity to the target protein is obtained.

In one embodiment, step (a) comprises identifying an anchor ligand by the following steps:
(i) preparing a synthetic target polypeptide corresponding to an epitope of the target protein (e.g., E17K Akt1) comprising an azide or alkynyl group;
(ii) preparing a first plurality of candidate peptides to screen against the target polypeptide comprising the complementary click handle for the target peptide (an alkynyl or azide group);
(iii) contacting the target polypeptide with the first plurality of candidate peptides;
(iv) providing a capture agent anchor by forming a disubstituted 1,2,3-triazole linkage between the first plurality of candidate peptides and the polypeptide target wherein the azido group and alkynyl group of the first plurality of candidate peptides and the polypeptide target are brought in close proximity by binding to the target peptide; and
(v) sequencing the anchor ligand;

In one embodiment, step (a) comprises identifying an anchor ligand using an in situ click screen against a large one-bead-one-compound library.

Also provided is a multiplex capture agent comprising two or more capture agents that bind specifically to two or more Akt1 mutations. In one embodiment, the multiplex capture agent comprises a designed anchor ligand, a designed secondary ligand, optionally, a designed tertiary ligand and optionally, a designed quarternary ligand.

The disclosure also provides a method of diagnosing a disease comprising a) administering to the subject the multiplex capture agent of described above linked to a detectable moiety; and b) detecting the moiety linked to the multiplex capture agent in the subject; wherein detection of the moiety diagnoses a disease in the subject.

In either of these methods, the disease can be a disease associated with increased expression or activation of E17K Akt1. In certain embodiments, the disease is cancer.

Also provided is a method of diagnosing a disease associated with increased expression or activation of E17K Akt1, comprising the steps of:
a) administering to the subject a multiplex capture agent of described herein, wherein the multiplex capture agent is linked to a detectable moiety; and
b) detecting the moiety linked to the multiplex capture agent in the subject; wherein detection of the moiety diagnoses the disease associated with increased expression or activation of E17K Akt1 in the subject.

BRIEF DESCRIPTION OF DRAWINGS

FIG. 2: Anchor ligand structure and characterization.

FIG. 3: Ligand-Directed Labeling Experiments. (FIG. 3A) Schematic of the ligand-directed labeling reaction. The yleaf (SEQ ID NO: 43) anchor ligand 5 (oval) binds to the PH Domain, and a nucleophilic amino acid (Nu) on the protein surface attacks the tosyl group, transferring the dye (star) onto the protein near the anchor binding site. The protein was then digested and analyzed via MALDI-TOF MS to discover fragments that have increased in mass by the weight of the dye. This experiment was designed to locate areas of the protein that are in close proximity to the bound yleaf (SEQ ID NO: 43) anchor. (FIG. 3B) Fluorescent gel image of GST-Akt1-PH Domain prior to trypsin digestion. Lane 1 is ladder, lane 2 is unlabeled protein, and lane 3 shows fluorescently-labeled protein (and excess fluorescent ligand at the bottom), confirming that the reaction has taken place. (FIG. 3C) This Pymol-assembled fusion protein highlights the PH Domain and the 33-mer epitope fragment used for screening. Sites containing a label on the GST-Akt1-PH Domain, as identified by MS analysis, are indicated in cyan. These results indicate that the yleaf (SEQ ID NO: 43) anchor is binding only in the area of the epitope, and does not have off-target binding interactions with any other part of this large protein.

FIG. 4: Images of the Cy5-yleaf (SEQ ID NO: 43)-PEG5-TAT peptide ligand in cells.

FIG. 5: The PCC agent triligand development strategy, structure, and inhibition data.

FIG. 9 is a schematic showing a screening strategy for anchor ligand determination. (FIG. 9A) Preclear: Library beads are incubated with streptavidin-alkaline phosphatase conjugate to remove any library beads that bind to this or the BCIP reagents. (FIG. 9B) Screen: Precleared library beads are incubated with the 33-mer target peptide containing an azide in situ click handle. The fragment catalyzes triazole formation between the alkyne on the 33-mer target and the azide on beads that contain peptide sequences that bind specifically to the 33-mer in a close enough proximity to the alkyne substitution for a click reaction to occur without copper. The unclicked peptide is then stripped from the beads and the remaining covalently attached 33-mer is detected by streptavidin-alkaline phosphatase with BCIP development.

FIG. 10 is a chart showing unsupervised clustering of anchor sequence ligands by aa similarity. Hit sequences from the anchor screen were analyzed by their hydrophobicity and sequence homology using principal component analysis. Circled clusters indicate regions where a peptide was selected and scaled-up as a possible anchor sequence. The potential anchor sequences that were tested are: dqntr (SEQ ID NO: 36), ypwve (SEQ ID NO: 20), eefef (SEQ ID NO: 77), yleaf (SEQ ID NO: 43) and elnhy (SEQ ID NO: 41). FIG. 10 discloses "QFLWE," "YPWVE," "QFKWE," "ISEYE," "NLVP," "ALNSK," "NRYVR," "LLLLL," "ALAF," "YHLFW," "NVYPT," "VYPT," "NHWGS," "HARHQ," "DHWGS," "HEWVT," "NQDTR," "DQNTR," "DQDTR," "DDDDD," "HFNKH," "HFDKH," "ELNHY," "DLLTF," "YLEAF," "LFHQV," "YHEWF," "GGGGG," "AKAFY," "GVEKF," "ARSDF," "YESSG," "EEPNF," and "YHKFW" as SEQ ID NOS 19-52, respectively, in order of appearance.

FIG. 24 is a schematic showing a screening strategy for biligand determination. (FIG. 24A) Preclear: Library beads are incubated with streptavidin-alkaline phosphatase conjugate to remove any library beads that bind to this or the BCIP reagents. (FIG. 24B) Target Screen: Precleared beads are incubated with the target and anchor ligand and allowed to "click" to form a triazole. The presence of the target his-tagged PH Domain is detected via an anti-His alkaline phosphatase antibody. The hit beads are then collected, decolorized, and stripped of protein. (FIG. 24C) Anti-Screen: Hit beads from the target screen are incubated with the off-target PH Domain and anti-his alkaline phosphatase. These hit beads bind to both the target and off-target (WT and E17K mutant). (FIG. 24D) Product Screen: The remaining beads are probed with streptavidin-alkaline phosphatase to determine which contain the click product and, thereby, have shown biligand formation.

FIG. 25 discloses "NWRL," "NERY," "HYRW," "YWKG," "YWRL," "WFRI," "NVYL," "AARW," "HWPR," "LLLL," "AYLY," "DWWR," "RPYY," "RHWS," "GGGG," "RRRR," "DDDD," "VWFR," "YYSR," "GRWY," "SRFY," "YNYK," and "RDYR" as SEQ ID NOS 53-75, respectively, in order of appearance.

FIG. 28 is a schematic showing screening strategy for triligand determination. (FIG. 28A) Preclear: Library beads are incubated with streptavidin-alkaline phosphatase conjugate to remove any library beads that bind to this or the BCIP reagents. (FIG. 28B) Target Screen: Precleared beads are incubated with the target and biligand and allowed to "click" to form a triazole. The presence of the target his-tagged PH Domain is detected via an anti-His alkaline phosphatase antibody. The hit beads are then collected, decolorized, and stripped of protein. (FIG. 28C) Anti-Screen: Hit beads from the target screen are incubated with the off-target, WT PH Domain and anti-his alkaline phosphatase. These hit beads bind to both the target and off-target (WT and E17K mutant). (FIG. 28D) Product Screen: The remaining beads are probed with streptavidin-alkaline phosphatase to determine which contain the click product and, thereby, have shown triligand formation.

DETAILED DESCRIPTION

Figure 1:
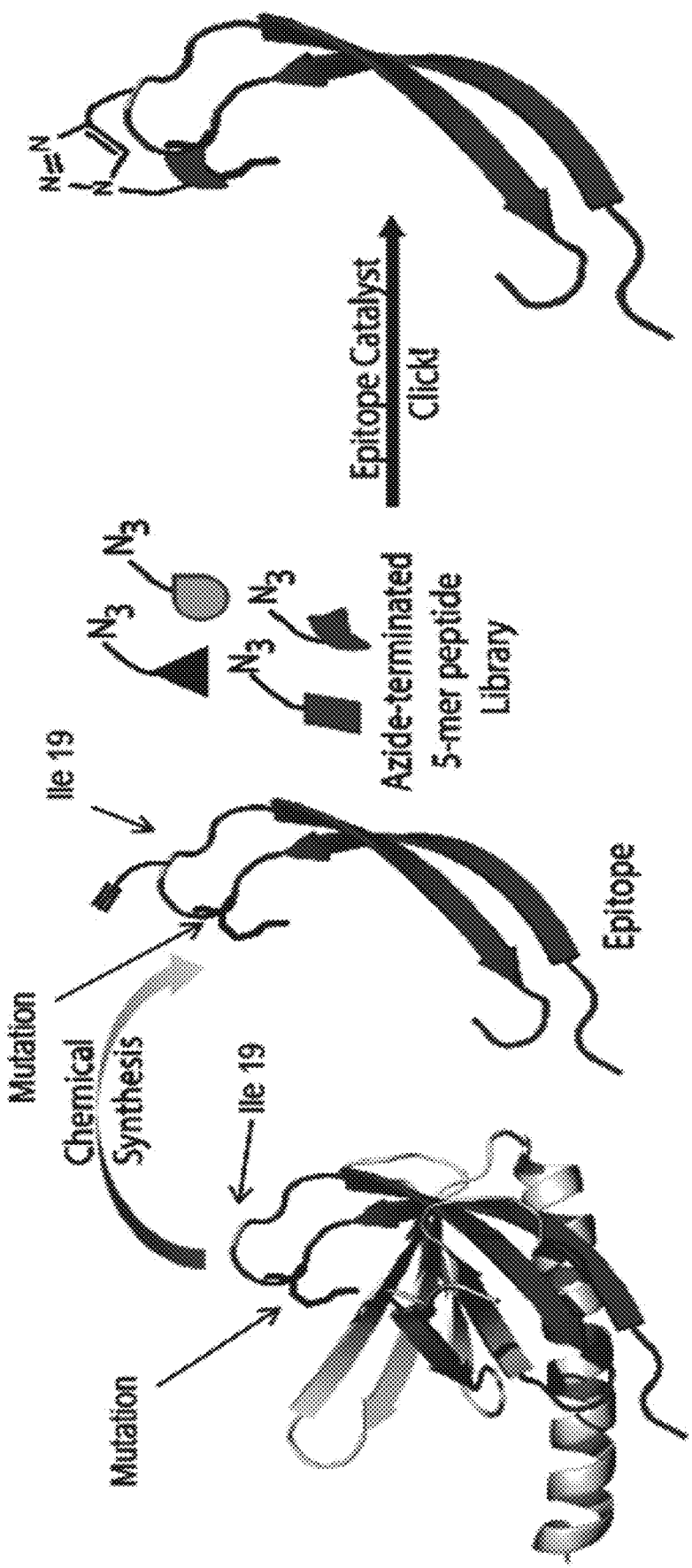
FIG. 1: Epitope design strategy for in situ click screen. The full Akt1 PH Domain protein contains an E17K mutation. To focus a chemical library screen on the region surrounding this mutation, only a portion of the PH Domain containing the E17K mutation was synthesized as a separate peptide epitope. Chemical synthesis of the epitope allowed for the substitution of the isoleucine at residue 19, the most proximal side-chain to the E17K mutation, with an alkyne-containing propargylglycine amino acid. This substitution focused the azide library screening directly to the site of the mutation. This in situ click screen format allows for the determination of peptides that bind in close proximity to the E17K mutation. Triazoles formed between an azide-containing library peptide and the alkyne-substituted epitope must be catalyzed by a molecular recognition event, indicating that the library peptide binds strongly near the mutation.

Provided herein is an epitope targeting strategy used to develop capture agents that preferentially bind to mutant versus wild type proteins. In one embodiment, the target peptide is a short-chain peptide to bind to the E17K oncogenic mutation of Akt1. According to other embodiments, the capture agent is made into a binder that is a cell-penetrant, mutant-selective inhibitor.

The targeting strategy directly substitutes an alkyne click handle into a chemically-synthesized peptide epitope which makes an easily addressable residue for selectively targeting a region of interest in a protein. This technique potentially eliminates the need for a binding pocket or a naturally addressable residue such as a phosphorylation site. For this work, the peptide represents the epitope of Akt1 containing the E17K point mutation. The epitope target is subjected to an in situ click screen against an OBOC peptide library of 5-mers (comprehensive in 18 amino acids), each terminated in an azide-presenting amino acid. For such a screen, the protein fragment provides a highly-selective scaffold that replaces the Cu(I) catalyst typically used in promoting the cyclo-addition between the alkyne and azide groups to form a triazole linkage (the Huisgen click reaction)[14]. Hits are defined as those compounds that are covalently coupled to the synthetic epitope through a triazole linkage. The juxtaposition of the chemically-substituted alkyne click handle to the E17K point mutation should mean that any hit peptide that has been covalently linked to the target sequence should bind in close proximity to the mutation.

This technique focused PCC agent development to a location on the PH Domain that was adjacent to the E17K oncogenic mutation. A 5-mer peptide was identified that exhibited a 10:1 selectivity for Akt1$^{E17K}$ relative to WT. The chemical flexibility and modularity of the PCC agent was exploited to append a dye and a cell penetrating peptide. The resultant ligand could preferentially localize in live cells expressing Akt1$^{E17K}$, again with high selectivity relative to WT. Finally, the PCC agent was developed into a biligand and then a triligand through the use of iterative in situ click chemistry[14]. These larger PCC agents could serve as highly selective inhibitors of Akt1$^{E17K}$ by blocking binding of the Pleckstrin Homology Domain of Akt1 to the PIP3 substrate.

The following description of the invention is merely intended to illustrate various embodiments of the invention. As such, the specific modifications discussed are not to be construed as limitations on the scope of the invention. It will be apparent to one skilled in the art that various equivalents, changes, and modifications may be made without departing from the scope of the invention, and it is understood that such equivalent embodiments are to be included herein.

Unless the context requires otherwise, throughout the present specification and claims, the word "comprise" and variations thereof, such as, "comprises" and "comprising" are to be construed in an open, inclusive sense, that is as "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Definitions

As used herein, the terms "capture agent of the invention", and "capture agents of the invention" refer to synthetic protein-catalyzed capture agents which bind Akt (e.g., Akt1, especially mutants of Akt1 such as E17K), as described herein.

"Amino" refers to the —NH$_2$ radical.
"Cyano" refers to the —CN radical.
"Hydroxy" or "hydroxyl" refers to the —OH radical.
"Imino" refers to the =NH substituent.
"Nitro" refers to the —NO$_2$ radical.
"Oxo" refers to the =O substituent.
"Thioxo" refers to the =S substituent.

"Alkyl" refers to a straight or branched hydrocarbon chain radical consisting solely of carbon and hydrogen atoms, which is saturated or unsaturated (i.e., contains one or more double and/or triple bonds), having from one to twelve carbon atoms ($C_1$-$C_{12}$ alkyl), preferably one to eight carbon atoms ($C_1$-$C_8$ alkyl) or one to six carbon atoms ($C_1$-$C_6$ alkyl), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, ethenyl, prop-1-enyl, but-1-enyl, pent-1-enyl, penta-1,4-dienyl, ethynyl, propynyl, butynyl, pentynyl, hexynyl, and the like. Unless stated otherwise specifically in the specification, an alkyl group may be optionally substituted.

"Alkylene" or "alkylene chain" refers to a straight or branched divalent hydrocarbon chain linking the rest of the molecule to a radical group, consisting solely of carbon and hydrogen, which is saturated or unsaturated (i.e., contains one or more double and/or triple bonds), and having from one to twelve carbon atoms, e.g., methylene, ethylene, propylene, n-butylene, ethenylene, propenylene, n-butenylene, propynylene, n-butynylene, and the like. The alkylene chain is attached to the rest of the molecule through a single or double bond and to the radical group through a single or double bond. The points of attachment of the alkylene chain to the rest of the molecule and to the radical group can be through one carbon or any two carbons within the chain. Unless stated otherwise specifically in the specification, an alkylene chain may be optionally substituted.

"Alkoxy" refers to a radical of the formula —OR$_a$ where R$_a$ is an alkyl radical as defined above containing one to twelve carbon atoms. Unless stated otherwise specifically in the specification, an alkoxy group may be optionally substituted.

"Aminocarbonyl" refers to a radical of the formula —C(=O)NR$_a$R$_a$, where each R$_a$ is independently H, alkyl or a linker moiety.

"α-amino carbonyl" refers to a radical of the formula —C(=O)CR$_b$(NR$_a$R$_a$)—, where each R$_a$ is independently H, alkyl or a linker moiety and R$_b$ is H or alkyl. In some embodiments, an alpha amino carbonyl is part of a cyclic moiety (e.g., peptide) where the carbonyl is within the ring and the amino (NR$_a$R$_a$) is exocyclic. For example, in certain embodiments and alpha aminocarbonyl is useful for Edman degradation of cyclic peptides.

"α-amido carbonyl" refers to a radical of the formula —C(=O)CR$_b$(N(C=O)R$_a$R$_a$)—, where each R$_a$ is independently H, alkyl or a linker moiety and R$_b$ is H or alkyl. In some embodiments, an alpha amido carbonyl is part of a cyclic moiety (e.g., peptide) where the carbonyl is within the ring and the amido (N(C=O)R$_a$R$_a$) is exocyclic.

"Alkylamino" refers to a radical of the formula —NHR$_a$ or —NR$_a$R$_a$ where each R$_a$ is, independently, an alkyl radical as defined above containing one to twelve carbon atoms. Unless stated otherwise specifically in the specification, an alkylamino group may be optionally substituted.

"Thioalkyl" refers to a radical of the formula —SR$_a$ where R$_a$ is an alkyl radical as defined above containing one to twelve carbon atoms. Unless stated otherwise specifically in the specification, a thioalkyl group may be optionally substituted.

"Aryl" refers to a hydrocarbon ring system radical comprising hydrogen, 6 to 18 carbon atoms and at least one aromatic ring. For purposes of this invention, the aryl radical may be a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

"Aralkyl" refers to a radical of the formula —R$_b$—R$_c$ where R$_b$ is an alkylene chain as defined above and R$_c$ is one or more aryl radicals as defined above, for example, benzyl, diphenylmethyl and the like. Unless stated otherwise specifically in the specification, an aralkyl group may be optionally substituted.

"Cycloalkyl" or "carbocyclic ring" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond.

Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethyl-bicyclo[2.2.1]heptanyl, and the like. Unless otherwise stated specifically in the specification, a cycloalkyl group may be optionally substituted.

"Cycloalkylalkyl" refers to a radical of the formula —$R_bR_d$ where $R_b$ is an alkylene chain as defined above and $R_d$ is a cycloalkyl radical as defined above. Unless stated otherwise specifically in the specification, a cycloalkylalkyl group may be optionally substituted.

"Fused" refers to any ring structure described herein which is fused to an existing ring structure in the compounds of the invention. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Heterocyclyl" or "heterocyclic ring" refers to a stable 3- to 18-membered non-aromatic ring radical which consists of two to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocyclyl group may be optionally substituted.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. Unless stated otherwise specifically in the specification, a N-heterocyclyl group may be optionally substituted.

"Heterocyclylalkyl" refers to a radical of the formula —$R_bR_e$ where $R_b$ is an alkylene chain as defined above and $R_e$ is a heterocyclyl radical as defined above, and if the heterocyclyl is a nitrogen-containing heterocyclyl, the heterocyclyl may be attached to the alkyl radical at the nitrogen atom. Unless stated otherwise specifically in the specification, a heterocyclylalkyl group may be optionally substituted.

"Heteroaryl" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, a heteroaryl group may be optionally substituted.

"N-heteroaryl" refers to a heteroaryl radical as defined above containing at least one nitrogen and where the point of attachment of the heteroaryl radical to the rest of the molecule is through a nitrogen atom in the heteroaryl radical. Unless stated otherwise specifically in the specification, an N-heteroaryl group may be optionally substituted.

"Heteroarylalkyl" refers to a radical of the formula —RbRf where Rb is an alkylene chain as defined above and Rf is a heteroaryl radical as defined above. Unless stated otherwise specifically in the specification, a heteroarylalkyl group may be optionally substituted.

The term "substituted" used herein means any of the above groups (e.g., alkyl, alkylene, alkoxy, alkylamino, aminocarbonyl, α-aminocarbonyl, α-amidocarbonyl, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl) wherein at least one hydrogen atom is replaced by a bond to a non-hydrogen atoms such as, but not limited to: a halogen atom such as F, C, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NR_gR_h$, —NR$_g$C(=O)R$_h$, —NR$_g$C(=O)NR$_g$R$_h$, —NR$_g$C(=O)OR$_h$, —NR$_g$SO$_2$R$_h$, —OC(=O) NR$_g$R$_h$, —OR$_g$, —SR$_g$, —SOR$_g$, —SO$_2$R$_g$, —OSO$_2$R$_g$, —SO$_2$OR$_g$, =NSO$_2$R$_g$, and —SO$_2$NR$_g$R$_h$. "Substituted" also means any of the above groups in which one or more hydrogen atoms are replaced with C(=O)R$_g$, C(=O)OR$_g$, C(=O)NR$_g$R$_h$, CH$_2$SO$_2$R$_g$, CH$_2$SO$_2$NR$_g$R$_h$. In the foregoing, R$_g$ and R$_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl group. In addition, each of the foregoing substituents may also be optionally substituted with one or more of the above substituents.

"Prodrug" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a mammalian organism (see, Bundgard, H., Design of Prodrugs (1985), pp. 7-9, 21-24 (Elsevier, Amsterdam)). A discussion of prodrugs is provided in Higuchi, T., et al., A.C.S. Symposium Series, Vol. 14, and in Bioreversible Carriers in Drug Design, Ed. Edward B. Roche, American Pharmaceutical Association and Pergamon Press, 1987.

The term "prodrug" is also meant to include any covalently bonded carriers, which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol or amide derivatives of amine functional groups in the compounds of the invention and the like.

The invention disclosed herein is also meant to encompass all pharmaceutically acceptable peptides of structure (I) or (I') being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively. These radiolabelled compounds could be useful to help determine or measure the effectiveness of the compounds, by characterizing, for example, the site or mode of action, or binding affinity to pharmacologically important site of action. Certain isotopically-labelled peptides of the invention, for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled peptides can generally be prepared by conventional techniques known to those skilled in the art or by processes analogous to those described in the Preparations and Examples as set out below using an appropriate isotopically-labeled reagent in place of the non-labeled reagent previously employed.

The invention disclosed herein is also meant to encompass the in vivo metabolic products of the disclosed peptides. Such products may result from, for example, the oxidation, reduction, hydrolysis, amidation, esterification, and the like of the administered compound, primarily due to enzymatic processes. Accordingly, the invention includes compounds produced by a process comprising administering a compound of this invention to a mammal for a period of time sufficient to yield a metabolic product thereof. Such products are typically identified by administering a radiolabelled compound of the invention in a detectable dose to an animal, such as rat, mouse, guinea pig, monkey, or to human, allowing sufficient time for metabolism to occur, and isolating its conversion products from the urine, blood or other biological samples.

"Mammal" includes humans and both domestic animals such as laboratory animals and household pets (e.g., cats, dogs, swine, cattle, sheep, goats, horses, rabbits), and non-domestic animals such as wildlife and the like.

"Mutant" or "Variant" refers to a protein that has high homology to a wild-type amino acid sequence, but not 100% identity with the wild-type amino acid sequence. High homology associated with mutants or variants is higher than 95, 96, 97, 98 or 99% but less than 100%. In certain embodiments, a mutant or variant differs from a wild-type sequence at 1, 2, 3, 4, 5, 6, 7, 8, 9 or 10 amino acids. In certain embodiments, a variant includes a protein with an amino acid sequence of E17K Akt1 provided below.

(SEQ ID NO: 6)
MSDVAIVKEGWLHKRGKYIKTWRPRYFLLKNDGTFIGYKERPQDVDQREA

PLNNFSVAQCQLMKTERPRPNTFIIRCLQWTTVIERTFHVETPEEREEWT

TAIQTVADGLKKQEEEEMDFRSGSPSDNSGAEEMEVSLAKPKHRVTMNEF

EYLKLLGKGTFGKVILVKEKATGRYYAMKILKKEVIVAKDEVAHTLTENR

VLQNSRHPFLTALKYSFQTHDRLCFVMEYANGGELFFHLSRERVESEDRA

RFYGAEIVSALDYLHSEKNVVYRDLKLENLMLDKDGHIKITDFGLCKEGI

KDGATMKTFCGTPEYLAPEVLEDNDYGRAVDWWGLGVVMYEMMCGRLPFY

NQDHEKLFELILMEEIRFPRTLGPEAKSLLSGLLKKDPKQRLGGGSEDAK

EIMQHRFFAGIVWQHVYEKKLSPPFKPQVTSETDTRYFDEEFT

According to other embodiments, a variant protein includes an epitope with the amino acid sequence of: MSDVAIVKEGWLKKRGKYIKTWRPRYFLLKNDG (SEQ ID NO: 7). According to certain embodiments, this epitope is located at the N-terminus of the protein.

"Wild-type" refers to a sequence that differs in sequence from the mutant or variant sequence. In certain embodiments, the wild-type sequence of Akt1 is shown below.

```
                                              (SEQ ID NO: 8)
MSDVAIVKEGWLHKRGEYIKTWRPRYFLLKNDGTFIGYKERPQDVDQREA

PLNNFSVAQCQLMKTERPRPNTFIIRCLQWTTVIERTFHVETPEEREEWT

TAIQTVADGLKKQEEEEMDFRSGSPSDNSGAEEMEVSLAKPKHRVTMNEF

EYLKLLGKGTFGKVILVKEKATGRYYAMKILKKEVIVAKDEVAHTLTENR

VLQNSRHPFLTALKYSFQTHDRLCFVMEYANGGELFFHLSRERVESEDRA

RFYGAEIVSALDYLHSEKNVVYRDLKLENLMLDKDGHIKITDFGLCKEGI

KDGATMKTFCGTPEYLAPEVLEDNDYGRAVDWWGLGVVMYEMMCGRLPFY

NQDHEKLFELILMEEIRFPRTLGPEAKSLLSGLLKKDPKQRLGGGSEDAK

EIMQHRFFAGIVWQHVYEKKLSPPFKPQVTSETDTRYFDEEFT
```

According to other embodiments, a wild-type protein includes an epitope with the amino acid sequence of: MSDVAIVKEGWLKKRGEYIKTWRPRYFLLKNDG (SEQ ID NO: 9). According to certain embodiments, this epitope is located at the N-terminus of the protein.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

The compounds (peptides) of the invention, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included. (D)-amino acids (also referred to as D-amino acids) are referred to herein in lower case letters (e.g. D-valine is referred to as "v"), while (L)-amino acids (also referred to herein as L-amino acids) are referred to in upper case letters (e.g. L-valine or valine is referred to as "V"). Glycine is non-chiral and is referred to as "G".

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present invention includes tautomers of any said compounds.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

The term "capture agent" as used herein refers to a composition that comprises one or more target-binding moieties and which specifically binds to a target protein via those target-binding moieties. Each target-binding moiety exhibits binding affinity for the target protein, either individually or in combination with other target-binding moieties. In certain embodiments, each target-binding moiety binds to the target protein via one or more non-covalent interactions, including for example hydrogen bonds, hydrophobic interactions, and van der Waals interactions. A capture agent may comprise one or more organic molecules, including for example polypeptides, peptides, polynucleotides, and other non-polymeric molecules. In some aspects a capture agent is a protein catalyzed capture agent (PCC).

The term "epitope" as used herein refers to a distinct molecular surface of a protein (e.g., the Akt1 protein). Typically, the epitope is a polypeptide and it can act on its own as a finite sequence of 10-40 amino acids. In the present disclosure, the epitope is prepared from the 33 amino acid long N-terminal fragment of the pleckstrin homology (PH) domain of Akt1, amino acids MSDVAIVKEGWLKKRGKY[Pra]KTWRPRYFLLKNDG (SEQ ID NO: 1). where the alkynyl containing Pra was substituted for an isoleucine in the actual Akt1 sequence. The E17K-containing crystal structure for the pleckstrin homology domain of Akt1 is PDB accession 2UZR. The full length Akt1 crystal structure which includes the (wildtype) pleckstrin homology domain is PDB accession 3O96.

The terms "polypeptide," "peptide," and "protein" are used interchangeably herein to refer to an amino acid sequence comprising a polymer of amino acid residues. The terms apply to amino acid polymers in which one or more amino acid residues is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function in a manner similar to the naturally occurring amino acids, and isomers thereof. Naturally occurring amino acids are those encoded by the genetic code, as well as those amino acids that are later modified, e.g., hydroxyproline, carboxyglutamate, 0-phosphoserine, and isomers thereof. The term "amino acid analogs" refers to compounds that have the same basic chemical structure as a naturally occurring amino acid, i.e., a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. The term "amino acid mimetics" refers to chemical compounds that have a structure that is different from the general chemical structure of an amino acid, but that functions in a manner similar to a naturally occurring amino acid. Amino acids may be referred to herein by either their commonly known three letter symbols or by the one-letter symbols recommended by the IUPAC-IUB Biochemical Nomenclature Commission.

The term "non-natural amino acid" as used herein refers to an amino acid that is different from the twenty naturally occurring amino acids (alanine, arginine, glycine, asparagine, aspartic acid, cysteine, glutamine, glutamic acid, serine, threonine, histidine, lysine, methionine, proline, valine, isoleucine, leucine, tyrosine, tryptophan, phenylalanine) in its side chain functionality. The non-natural amino acid can be a close analog of one of the twenty natural amino acids, or it can introduce a completely new functionality and chemistry, as long as the hydrophobicity of the non-natural amino acid is either equivalent to or greater than that of the natural amino acid. The non-natural amino acid can either replace an existing amino acid in a protein (substitution), or be an addition to the wild type sequence (insertion). The incorporation of non-natural amino acids can be accomplished by known chemical methods including solid-phase peptide synthesis or native chemical ligation, or by biological methods.

The terms "specific binding," "selective binding," "selectively binds," or "specifically binds" as used herein refer to capture agent binding to an epitope on a predetermined antigen. Typically, the capture agent binds with an affinity ($K_D$) of approximately less than $10^{-5}$ M, such as approximately less than $10^{-6}$ M, $10^{-7}$ M, $10^{-8}$ M, $10^{-9}$ M or $10^{-10}$ M or even lower.

The term "$K_D$" as used herein refers to the dissociation equilibrium constant of a particular capture agent-antigen interaction. Typically, the capture agents of the invention bind to an Akt protein with a dissociation equilibrium constant ($K_D$) of less than approximately $10^{-6}$ M, $10^{-7}$ M, $10^{-8}$ M, $10^{-9}$ M or $10^{-10}$ M or even lower, for example, as determined using surface plasmon resonance (SPR) technology in a Biacore instrument using the capture agent as the ligand and the Akt protein as the analyte, and bind to an Akt protein with an affinity corresponding to a $K_D$ that is at least ten-fold lower, such as at least 100 fold lower, for instance at least 1000 fold lower, such as at least 10,000 fold lower, for instance at least 100,000 fold lower than its affinity for binding to a non-specific antigen (e.g., BSA, casein) other than the predetermined antigen or a closely-related antigen. The amount with which the affinity is lower is dependent on the $K_D$ of the capture agent, so that when the $K_D$ of the capture agent is very low (that is, the capture agent is highly specific), then the amount with which the affinity for the antigen is lower than the affinity for a non-specific antigen may be at least 10,000 fold.

The term "$k_d$" ($sec^{-1}$) as used herein refers to the dissociation rate constant of a particular capture agent-antigen interaction. Said value is also referred to as the $k_{off}$ value.

The term "$k_a$" ($M^{-1} \times sec^{-1}$) as used herein refers to the association rate constant of a particular capture agent-antigen interaction.

The term "$K_D$" (M) as used herein refers to the dissociation equilibrium constant of a particular capture agent-antigen interaction.

The term "$K_A$" ($M^{-1}$) as used herein refers to the association equilibrium constant of a particular capture agent-antigen interaction and is obtained by dividing the $k_a$ by the $k_d$.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

The term "condition" as used herein refers generally to a disease, event, or a change in health status. A change in health status may be associated with a particular disease or event, in which case the change may occur simultaneously with or in advance of the disease or event. In those cases where the change in health status occurs in advance of a disease or event, the change in health status may serve as a predictor of the disease or event. For example, a change in health status may be an alteration in the expression level of a particular gene associated with a disease or event. Alternatively, a change in health status may not be associated with a particular disease or event.

The terms "treat," "treating," or "treatment" as used herein generally refer to preventing a condition or event, slowing the onset or rate of development of a condition or delaying the occurrence of an event, reducing the risk of developing a condition or experiencing an event, preventing or delaying the development of symptoms associated with a condition or event, reducing or ending symptoms associated with a condition or event, generating a complete or partial regression of a condition, lessening the severity of a condition or event, or some combination thereof.

An "effective amount" or "therapeutically effective amount" as used herein refers to an amount effective, at dosages and for periods of time necessary, to achieve a desired therapeutic result. A therapeutically effective amount of a capture agent may vary according to factors such as the disease state, age, sex, and weight of the individual, and the ability of the capture agent to elicit a desired response in the individual.

The term "antibody" as used herein refers to a protein of the kind that is produced by activated B cells after stimulation by an antigen and can bind specifically to the antigen promoting an immune response in biological systems. Full antibodies typically consist of four subunits including two heavy chains and two light chains. The term antibody includes natural and synthetic antibodies, including but not limited to monoclonal antibodies, polyclonal antibodies or fragments thereof. Exemplary antibodies include IgA, IgD, IgG1, IgG2, IgG3, IgM and the like. Exemplary fragments include Fab, Fv, Fab', F(ab')$_2$ and the like. A monoclonal antibody is an antibody that specifically binds to and is thereby defined as complementary to a single particular spatial and polar organization of another biomolecule which is termed an "epitope." In some forms, monoclonal antibodies can also have the same structure. A polyclonal antibody refers to a mixture of different monoclonal antibodies. In some forms, polyclonal antibodies can be a mixture of monoclonal antibodies where at least two of the monoclonal antibodies binding to a different antigenic epitope. The different antigenic epitopes can be on the same target, different targets, or a combination. Antibodies can be prepared by techniques that are well known in the art, such as immunization of a host and collection of sera (polyclonal) or by preparing continuous hybridoma cell lines and collecting the secreted protein (monoclonal).

The term "stable" as used herein with regard to a capture agent protein catalyzed capture agent or pharmaceutical formulation thereof refers to the agent or formulation retaining structural and functional integrity for a sufficient period of time to be utilized in the methods described herein.

The term "synthetic" as used herein with regard to a protein catalyzed capture agent or capture agent refers to the capture agent has been generated by chemical rather than biological means.

Unless otherwise stated, sequence identity/similarity values provided herein refer to the value obtained using the BLAST 2.0 suite of programs using default parameters (Altschul, et al., (1997) Nucleic Acids Res. 25:3389-402).

As those of ordinary skill in the art will understand, BLAST searches assume that proteins can be modeled as random sequences. However, many real proteins comprise regions of nonrandom sequences, which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, (1993) Comput. Chem. 17:149-63) and XNU (Claverie and States, (1993) Comput. Chem. 17:191-201) low-complexity filters can be employed alone or in combination.

As used herein, "sequence identity" or "identity" in the context of two nucleic acid or polypeptide sequences includes reference to the residues in the two sequences, which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Sequences, which differ by such conservative substitutions, are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, (1988) Computer Applic. Biol. Sci. 4:11-17, e.g., as implemented in the program PC/GENE (Intelligenetics, Mountain View, Calif., USA).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" or "substantially identical" of polynucleotide sequences means that a polynucleotide comprises a sequence that has between 50-100% sequence identity, preferably at least 50% sequence identity, preferably at least 60% sequence identity, preferably at least 70%, more preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of between 55-100%, preferably at least 55%, preferably at least 60%, more preferably at least 70%, 80%, 90% and most preferably at least 95%.

The term "Akt" collectively refers to the three Akt isoforms (Akt1, Akt2, and Akt3). Akt is a member of the serine/threonine protein kinase family and is involved in processes such as glucose metabolism, apoptosis, and cell proliferation. Akt plays a central regulatory role in growth factor signaling, and serves as a key node in phosphatidylinositol 3-kinase (PI3K) signaling.

Overexpression and/or hyperactivation of Akt is associated with diabetes and many cancers, making Akt an important target for the development of drugs and diagnostics. Overexpression and/or activation of Akt can increase resistance of tumors to chemo or radio therapies.

Development of Akt Capture Agents

Antibodies are currently the default detection agent for use in diagnostic platforms. However, antibodies possess several disadvantages, including high cost, poor stability, and, in many cases, lack of proper characterization and high specificity. The ideal replacement for use in diagnostic assays should be synthetic, stable to a range of thermal and chemical conditions, and display high affinity and specificity for the target of interest.

A high quality monoclonal antibody possesses low-nanomolar affinity and high target specificity. Interestingly, structural and genetic analyses of the antigen recognition surface have shown that the majority of the molecular diversity of the variable loops is contained in a single highly variable loop (CDR-H3). In humans, this loop ranges in size from 1-35 residues (15 on average), can adopt a wide range of structural conformations, and is responsible for most of the interactions with the antigen. The other five loops are significantly less diverse and adopt only a handful of conformations. This suggests that a carefully selected "anchor" peptide can dominate the mode and strength of the interaction between a capture agent and its target protein. It also suggests that other peptide components, while providing only modest contributions to the total interaction energy, can supply important scaffolding features and specificity elements.

In situ click chemistry is a technique in which a small molecule enzymatic inhibitor is separated into two moieties, each of which is then expanded into a small library—one containing acetylene functionalities, and the other containing azide groups. The enzyme itself then assembles the 'best fit' inhibitor from these library components by selectively promoting 1,3-dipolar cycloaddition between the acetylene and azide groups to form a triazole linkage (the 'click' reaction). The protein effectively plays the role of an extremely selective variant of the Cu(I) catalyst that is commonly used for such couplings. The enzyme promotes the click reaction only between those library components that bind to the protein in the right orientation. The resultant inhibitor can exhibit far superior affinity characteristics relative to the initial inhibitor that formed the basis of the two libraries.

Sequential in situ click chemistry extends the in situ click chemistry concept to enable the discovery of multiligand capture agents (see: USSN 20100009896, incorporated herein by reference). This process was used previously to produce a triligand capture agent against the model protein carbonic anhydrase II (CAII). Sequential in situ click chemistry has several advantages. First, structural information about the protein target is replaced by the ability to sample a very large chemical space to identify the ligand components of the capture agent. For example, an initial ligand may be identified by screening the protein against a large ($>10^6$ element) one-bead-one-compound (OBOC) peptide library, where the peptides themselves may be comprised of natural, non-natural, and/or artificial amino acids. The resultant anchor ligand is then utilized in an in situ click screen, again using a large OBOC library, to identify a biligand binder. A second advantage is that the process can be repeated, so that the biligand is used as an anchor to identify a triligand, and so forth. The final capture agent can then be scaled up using relatively simple and largely automated chemistries, and it can be developed with a label, such as a biotin group, as an intrinsic part of its structure. This approach permits the exploration of branched, cyclic, and linear capture agent architectures. While many strategies for protein-directed multiligand assembly have been described, most require detailed structural information on the target to guide the screening strategy, and most (such as the original in situ click approach), are optimized for low-diversity small molecule libraries.

The present embodiment further generalizes the in situ click application to naively find an anchor ligand using in situ click. In previous approaches, a known binder was necessary to begin the ligand. This method provides a mechanism to find an anchor ligand de novo.

As described herein, an iterative in situ click chemistry approach was utilized to synthesize a biligand capture agent that specifically binds Akt. This in situ click chemistry approach comprised two steps. First, a synthetic polypeptide derived from Akt was selected as the initial screening target. Second, the secondary ligand selection process took advantage of the fact that an in situ click screen, in which an anchor ligand and full-length protein target are screened against a large OBOC library, will selectively generate multiligand products on the hit beads. This concept was expanded in the form of "product screens," in which the presence of on-bead clicked product is taken to be the signature of a hit bead. Such a product screen can be utilized to increase both the affinity and/or selectivity of the final multiligand capture agent.

The capture agents generated by the methods disclosed herein were found to display binding affinity for Akt. The capture agents were shown to function as both capture and detection agents in ELISA assays and efficiently immunoprecipitate Akt.

Akt Capture Agents

In one aspect, provided herein is a stable, synthetic capture agent that specifically binds Akt, wherein the capture agent comprises a designed anchor ligand, a designed secondary ligand, optionally a designed tertiary ligand, and optionally a designed quarternary ligand, and wherein the ligands selectively bind Akt. In one embodiment, the capture agent specifically binds Akt1. In another embodiment, the ligands selectively bind Akt1. In another embodiment, the capture agent selectively binds to an E17K PH domain mutation of Akt1 over binding to wild-type Akt1.

In certain embodiments, provided herein are biligand Akt capture agents comprising two target-binding moieties. The first target-binding moiety is referred to as an anchor ligand, and the second is referred to as a secondary ligand. Also provided are triligand and tetraligand capture agents, wherein the third target-binding moiety is referred to as a tertiary ligand, and the fourth target-binding moiety is referred to as a quarternary ligand.

In certain embodiments, a target-binding moiety comprises one or more polypeptides or peptides. In certain of these embodiments, a target-binding moiety comprises one or more peptides comprising D-amino acids, L-amino acids, and/or amino acids substituted with functional groups selected from the group consisting of substituted and unsubstituted alkyl, substituted and unsubstituted azido, substituted and unsubstituted alkynyl, substituted and unsubstituted biotinyl, substituted and unsubstituted azioalkyl, substituted and unsubstituted polyethyleneglycolyl, and substituted and unsubstituted 1,2,3-triazole.

In certain embodiments, the anchor ligand and secondary ligand are linked to one another via a covalent linkage to form a capture agent biligand. In certain of these embodiments, the anchor ligand and secondary ligand are linked to one another via an amide bond or a 1,4-disubstituted-1,2,3-triazole linkage as shown below:

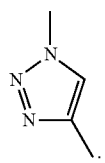

1,4-disubstituted-1,2,3-triazole linkage

In those embodiments where the anchor and secondary ligands are linked to one another via a 1,4-disubstituted-1,2,3-triazole linkage, the 1,4-disubstituted-1,2,3-triazole linkage may be formed by Cu-Catalyzed Azide/Alkyne Cycloaddition (CuAAC).

In certain embodiments, the anchor and secondary ligands are linked to one another by a Tz4 linkage having the following structure:

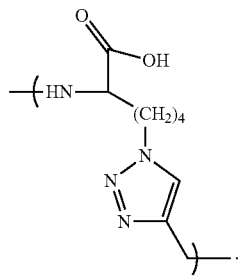

In certain embodiments, the anchor and secondary ligands are linked to one another by a Tz5 linkage having the following structure:

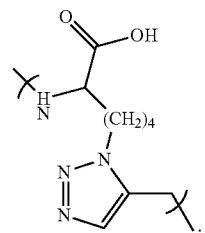

In certain embodiments, the tertiary and/or quarternary ligand is linked to the capture agent biligand by a covalent linkage, preferably via the secondary ligand in the biligand. In certain of these embodiments, the tertiary ligand and the biligand and/or the quarternary ligand and the tertiary ligand are linked to one another by a Tz4 linkage.

In those embodiments wherein one or more of the anchor, secondary, tertiary, and/or quarternary ligands are linked to one another via amide bonds, the amide bond may be formed by coupling a carboxylic acid group and an amine group in the presence of a coupling agent (e.g., O-(7-azabenzotriazo-1-yl)-N,N,N',N'-tetramethyluronium hexafluorophosphate (HATU), N-hydroxy-7-aza-benzotriazole (HOAt), or diisopropylethylamine (DIEA) in DMF).

In certain embodiments, the capture agents provided herein are stable across a range of reaction conditions and/or storage times. A capture agent that is "stable" as used herein maintains the ability to specifically bind to a target protein. In certain embodiments, the capture agents provided herein are more stable than an antibody binding to the same target protein under one or more reaction and/or storage conditions. For example, in certain embodiments the capture agents provided herein are more resistant to proteolytic degradation than an antibody binding to the same target protein.

In certain embodiments, the capture agents provided herein have a shelf-life of greater than six months, meaning that they are stable in storage for greater than six months. In certain of these embodiments, the capture agents have a shelf-life of one year or greater, two years or greater, or more than three years. In certain of these embodiments, the capture agents are stored as a lyophilized powder. In certain embodiments, the capture agents provided herein have a longer shelf-life than an antibody binding to the same target protein.

In certain embodiments, the capture agents provided herein are stable at temperatures ranging from about −80° to about 120° C. In certain of these embodiments, the capture agents are stable within a temperature range of −80° to −40° C.; −40° to −20° C.; −20° to 0° C.; 0° to 20° C.; 20° to 40° C.; 40° to 60° C.; 60° to 80° C.; and/or 80° to 120° C. In certain embodiments, the capture agents provided herein are stable across a wider range of temperatures than an antibody binding to the same target protein, and/or remain stable at a specific temperature for a longer time period than an antibody binding to the same target protein.

In certain embodiments, the capture agents provided herein are stable at a pH range from about 3.0 to about 8.0. In certain embodiments, the range is about 4.0 to about 7.0. In certain embodiments, the range is about 7.0 to about 8.0.

In certain embodiments, the capture agents provided herein are stable in human serum for more than 12 hours. In certain of these embodiments, the capture agents are stable in human serum for more than 18 hours, more than 24 hours, more than 36 hours, or more than 48 hours. In certain embodiments, the capture agents provided herein are stable for a longer period of time in human serum than an antibody binding to the same target protein. In certain embodiments, the capture agents are stable as a powder for two months at a temperature of about 60° C.

In certain embodiments, the capture agents provided herein may comprise one or more detection labels, including for example biotin, copper-1,4,7,10-tetraazacyclododecane-1,4,7,10-tetraacetic acid (copper-DOTA), $^{64}$Cu DOTA, $^{68}$Ga DOTA, $^{18}$F, $^{64}$Cu, $^{68}$Ga, $^{89}$Zr, $^{124}$I, $^{86}$Y, $^{94m}$Tc, $^{110m}$In, $^{11}$C, $^{76}$Br, $^{123}$I, $^{131}$I $^{67}$Ga, $^{111}$In and $^{99m}$Tc, or other radiolabeled products that may include gamma emitters, proton emitters, positron emitters, tritium, or covered tags detectable by other methods (i.e., gadolinium) among others. In a particular embodiment, the detection label is $^{18}$F. In certain embodiments, the capture agents may be modified to be used as imaging agents. The imaging agents may be used as diagnostic agents.

In certain embodiments, the capture agents provided herein may be modified to obtain a desired chemical or biological activity. Examples of desired chemical or biological activities include, without limitation, improved solubility, stability, bioavailability, detectability, or reactivity. Examples of specific modifications that may be introduced to a capture agent include, but are not limited to, cyclizing the capture agent through formation of a disulfide bond; modifying the capture agent with other functional groups or molecules. Similarly, a capture agent may be synthesized to bind to non-canonical or non-biological epitopes on proteins, thereby increasing their versatility. In certain embodiments, the capture agent may be modified by modifying the synthesis blocks of the target-binding moieties before the coupling reaction.

Methods of Making/Screening Capture Agents

Provided herein in certain embodiments are methods of screening target-binding moieties and/or making capture agents that comprise these target-binding moieties. Methods for screening target-binding moieties and/or making capture agents that comprise these target-binding moieties can also be found in International Publication Nos. WO 2012/106671, WO 2013/033561, WO 2013/009869 and WO 2014/074907, each of which is incorporated by reference, herein, in their entireties.

The capture agent production methods disclosed herein begin with identification of a short-chain anchor peptide, then proceed by adding additional covalently coupled peptide ligands via a process that is promoted by the target protein. The specificity and inhibitory potency of the final multiligand capture agent are augmented by the peripheral peptide ligands.

In certain embodiments, the methods provided herein comprise the following steps:
(a) identifying an anchor ligand by the following steps:
  (i) preparing a synthetic target polypeptide corresponding to an epitope of the target protein comprising an azide or alkynyl group;
  (ii) preparing a first plurality of candidate peptides to screen against the target polypeptide comprising the complementary click handle for the target peptide (an alkynyl or azide group);
  (iii) contacting the target polypeptide with the first plurality of candidate peptides;
  (iv) providing a capture agent anchor by forming a disubstituted 1,2,3-triazole linkage between the first plurality of candidate peptides and the polypeptide target wherein the azido group and alkynyl group of the first plurality of candidate peptides and the polypeptide target are brought in close proximity by binding to the target peptide; and
  (v) sequencing the anchor ligand;
(b) identifying a secondary ligand by the following steps:
  (i) preparing an anchor ligand selection block comprising the anchor ligand and an azido group or an alkynyl group;
  (ii) preparing a second plurality of candidate peptides to select a secondary ligand for the target protein, the second plurality of peptides comprising an azido group or an alkynyl group if the anchor ligand selection block comprises an alkynyl group and azido group respectively;
  (iii) contacting the anchor ligand selection block and the second plurality of peptides with the target protein;
  (iv) providing a capture agent biligand by forming a disubstituted 1,2,3-triazole linkage between the anchor ligand selection block and the secondary ligand wherein the azido and alkynyl group of the anchor ligand selection block and the secondary ligand are brought in close proximity by binding to the target protein;
  (v) selecting the capture agent biligand that has an affinity with the target protein; and
  (vi) sequencing the secondary ligand;
(c) identifying a tertiary ligand by the following steps:
  (i) preparing a biligand selection block comprising an azido group or an alkynyl group; and
  (ii) repeating steps (b)(ii) to (b)(vi) using a third plurality of candidate peptides until a capture agent having desired binding affinity to the target protein is obtained;
(d) identifying a quarternary ligand and, optionally, additional ligands by the following steps:
  (i) preparing a triligand selection block comprising an azido group or an alkynyl group; and
  (ii) repeating steps (c)(ii) to (c)(vi) using a fourth plurality, fifth plurality, etc., of candidate peptides until a capture agent having desired binding affinity to the target protein is obtained.

In certain embodiments, steps (b)(ii) to (b)(vi) are repeated one time, resulting in production of a capture agent triligand.

In certain embodiments, the first, second, and any additional pluralities of candidate peptides comprise a "one bead one compound" (OBOC) peptide library, wherein the peptides comprise 5 to 7 D-amino acid residues and coupled with a D-propargylglycine at the N-terminus. In certain embodiments, the pluralities of candidate peptides may be different. In other embodiments, one or more of the pluralities may contain the same peptide pool.

In certain embodiments, the secondary ligand is covalently bound to the anchor ligand, and the tertiary ligand is covalently bound to the secondary ligand. In another embodiment, the secondary and tertiary ligands are covalently bound to the anchor ligand.

In certain embodiments, the methods provided herein utilize a known peptide target.

In certain embodiments, the anchor ligand used for the screening process may be modified with a biotin. For example, the anchor ligand used for the screening process may be Biotin-PEG$_5$-LIGAND-Pra.

In one embodiment, the screening/preparation process comprises the following steps:
a) contacting the Akt with the Biotin-PEG$_5$-LIGAND-Pra anchor ligand to provide an Akt-anchor complex;

b) contacting the Akt-anchor complex with a first plurality of candidate peptides to select a secondary ligand, the peptides coupled with an Az4-CONH$_2$ moiety at its N-terminus;

c) providing a capture agent biligand by forming a disubstituted-1,2,3-triazole linkage between the anchor ligand selection block and the secondary ligand, wherein the azido and alkynyl group of the anchor ligand selection block and the secondary ligand are brought in close proximity by binding to the target protein to provide a bead modified with the capture agent biligand;

d) selecting the beads modified with the capture agent biligand;

e) removing the capture agent biligands from the beads;

f) sequencing the secondary ligand of the capture agent biligand;

g) preparing the capture agent biligand with an N-terminal Biotin-(PEG)$_5$ label and a C-terminal Az4; and h) repeating the above steps until an Akt capture agent having the desired properties is identified.

In certain embodiments, methods are provided for synthesizing a capture agent as provided herein. In certain embodiments, these methods comprise:

a) preparing a synthesis block of a target-binding moiety, the synthesis block comprising the target-binding moiety and at least one reactive group that can form a desired linkage with another synthesis block, wherein:
i) the linkage is selected from the group consisting of amide linkage, 1,4-disubstituted 1,2,3-triazole linkage, and 1,5-disubstituted 1,2,3-triazole linkage; and
ii) all other active functional groups of the target-binding moiety are protected to avoid undesired reactions; and b) coupling the synthesis blocks of the target-binding moieties to provide the capture agent.

Methods for Targeting Akt

An approach for synthesizing molecules that bind Akt is described and demonstrated. The invention includes first preparing a peptide or polypeptide fragment corresponding to the 33 amino acid long of the E17K pleckstrin homology (PH) domain of Akt1. That polypeptide can be site-specifically modified by either substituting one of the naturally occurring amino acids with an artificial amino acid, or the polypeptide fragment is modified after synthesis by chemically altering a specific amino acid. In both cases, the polypeptide can be modified to incorporate either an alkyne or an azide chemical group near the site-specific modification. That azide (or alkyne) containing fragment is then incubated with a very large molecular library. This library, while typically chemically diverse, is also characterized by the fact that each element contains an alkyne (or, instead, each element contains an azide) group. The incubation can be done under conditions that the modified polypeptide fragment can provide a catalytic scaffold for promoting the covalent coupling between select library elements and the polypeptide fragment. In this embodiment, it promotes this coupling by catalyzing the formation of a triazole linkage that is the reaction product of the acetylene and azide groups. According to several embodiments, the selectivity of this catalyzed process is very high. This means that only a very small fraction of the elements in the molecular library will be coupled. Those elements are identified through analytical techniques, and then tested for binding to the polypeptide fragment, or to the entire protein biomolecule from which the polypeptide fragment was extracted. This approach provides a route towards identifying molecules that selectively bind to the intended epitope of the protein target. Approaches known in the art may then be utilized to increase the selectivity and the affinity of the identified binders, without sacrificing their epitope selective binding characteristics.

The following steps are performed in one embodiment of the process. A protein target (1) is selected for developing capture agent molecules that will bind to that protein target. The protein target contains an epitope with a known sequence of amino acids (2). A polypeptide fragment (3) corresponding to the epitope of the protein is synthesized, but with two modifications. First, (3) is either substituted or chemically modified so as to provide an azide or alkyne group. Second, a site on the polypeptide is modified (4) with a label (a fluorophore or biotin group, for example) for use during the screening steps. There are many ways through which this label can be introduced.

If a molecular library of 1 million molecules, designed to span a broad chemical space, is incubated with a ~50-100 nM concentration solution of the modified polypeptide fragment (3), under standard blocking conditions to prevent non-selective binding, then that screen will generate about 20-100 hit molecules. Of those hit molecules, a small number (1-10) will be molecules that specifically bind to the protein target of interest. Approaches described herein can then be utilized to increase the affinity and specificity of those protein target-specific binders.

In Vitro

For detection of Akt in solution, a capture agent of the invention can be detectably labeled, then contacted with the solution, and thereafter formation of a complex between the capture agent and the Akt target can be detected. As an example, a fluorescently labeled capture agent can be used for in vitro Akt detection assays, wherein the capture agent is added to a solution to be tested for Akt under conditions allowing binding to occur. The complex between the fluorescently labeled capture agent and the Akt target can be detected and quantified by, for example, measuring the increased fluorescence polarization arising from the complex-bound peptide relative to that of the free peptide.

Alternatively, a sandwich-type "ELISA" assay can be used, wherein a capture agent is immobilized on a solid support such as a plastic tube or well, then the solution suspected of containing Akt is contacted with the immobilized binding moiety, non-binding materials are washed away, and complexed polypeptide is detected using a suitable detection reagent for recognizing Akt.

For detection or purification of soluble Akt from a solution, capture agents of the invention can be immobilized on a solid substrate such as a chromatographic support or other matrix material, then the immobilized binder can be loaded or contacted with the solution under conditions suitable for formation of a capture agent/Akt complex. The non-binding portion of the solution can be removed and the complex can be detected, for example, using an anti-Akt antibody, or an anti-binding polypeptide antibody, or the Akt can be released from the binding moiety at appropriate elution conditions.

In Vivo Diagnostic Imaging

A particularly preferred use for the capture agents of the invention is for creating visually readable images of Akt or Akt-expressing cells in a biological fluid, such as, for example, in human serum. The Akt capture agents disclosed herein can be converted to imaging reagents by conjugating the capture agents with a label appropriate for diagnostic detection. Preferably, a capture agent exhibiting much greater specificity for Akt than for other serum proteins is conjugated or linked to a label appropriate for the detection methodology to be employed. For example, the capture agent can be conjugated with or without a linker to a paramagnetic chelate suitable for Magnetic Resonance Imaging (MRI), with a radiolabel suitable for x-ray, Positron Emission Tomography (PET), Single Photon Emission Computed Tomography (SPECT) or scintigraphic imaging (including a chelator for a radioactive metal), with an ultrasound contrast agent (e.g., a stabilized microbubble, a microballoon, a microsphere or what has been referred to as a gas filled "liposome") suitable for ultrasound detection, or with an optical imaging dye.

In another embodiment, rather than directly labeling a capture agent with a detectable label or radiotherapeutic construct, one or more peptides or constructs of the invention can be conjugated with for example, avidin, biotin, or an antibody or antibody fragment that will bind the detectable label or radiotherapeutic.

A. Magnetic Resonance Imaging

The Akt capture agents described herein can advantageously be conjugated with a paramagnetic metal chelate in order to form a contrast agent for use in MRI. Preferred paramagnetic metal ions have atomic numbers 21-29, 42, 44, or 57-83. This includes ions of the transition metal or lanthanide series which have one, and more preferably five or more, unpaired electrons and a magnetic moment of at least 1.7 Bohr magneton. Preferred paramagnetic metals include, but are not limited to, chromium (III), manganese (II), manganese (III), iron (II), iron (III), cobalt (II), nickel (II), copper (II), praseodymium (III), neodymium (III), samarium (III), gadolinium (III), terbium (III), dysprosium (III), holmium (III), erbium (III), europium (III) and ytterbium (III), chromium (III), iron (III), and gadolinium (III). The trivalent cation, $Gd^{3+}$, is particularly preferred for MRI contrast agents, due to its high relaxivity and low toxicity, with the further advantage that it exists in only one biologically accessible oxidation state, which minimizes undesired metabolism of the metal by a patient. Another useful metal is $Cr^{3+}$, which is relatively inexpensive. Gd(III) chelates have been used for clinical and radiologic MR applications since 1988, and approximately 30% of MRI exams currently employ a gadolinium-based contrast agent.

The paramagnetic metal chelator is a molecule having one or more polar groups that act as a ligand for, and complex with, a paramagnetic metal. Suitable chelators are known in the art and include acids with methylene phosphonic acid groups, methylene carbohydroxamine acid groups, carboxyethylidene groups, or carboxymethylene groups. Examples of chelators include, but are not limited to, diethylenetriaminepentaacetic acid (DTPA), 1,4,7,10-tetraazacyclo-tetradecane-1,4,7,10-tetraacetic acid (DOTA), 1-substituted 1,4,7,-tricarboxymethyl-1,4,7,10-teraazacyclododecane (DO3A), ethylenediaminetetraacetic acid (EDTA), and 1,4,8,11-tetra-azacyclotetradecane-1,4,8,11-tetraacetic acid (TETA). Additional chelating ligands are ethylene bis-(2-hydroxy-phenylglycine) (EHPG), and derivatives thereof, including 5-Cl-EHPG, 5-Br-EHPG, 5-Me-EHPG, 5-t-Bu-EHPG, and 5-sec-Bu-EHPG; benzodiethylenetriamine pentaacetic acid (benzo-DTPA) and derivatives thereof, including dibenzo-DTPA, phenyl-DTPA, diphenyl-DTPA, benzyl-DTPA, and dibenzyl DTPA; bis-2 (hydroxybenzyl)-ethylene-diaminediacetic acid (HBED) and derivatives thereof; the class of macrocyclic compounds which contain at least 3 carbon atoms, more preferably at least 6, and at least two heteroatoms (0 and/or N), which macrocyclic compounds can consist of one ring, or two or three rings joined together at the hetero ring elements, e.g., benzo-DOTA, dibenzo-DOTA, and benzo-NOTA, where NOTA is 1,4,7-triazacyclononane N,N',N"-triacetic acid, benzo-TETA, benzo-DOTMA, where DOTMA is 1,4,7,10-tetraazacyclotetradecane-1,4,7,10-tetra(methyl tetraacetic acid), and benzo-TETMA, where TETMA is 1,4,8,11-tetraazacyclotetradecane-1,4,8,11-(methyl tetraacetic acid); derivatives of 1,3-propylene-diaminetetraacetic acid (PDTA) and triethylenetetraaminehexaacetic acid (TTHA); derivatives of 1,5,10?N,N',N"-tris(2,3-dihydroxybenzoyl)-tricatecholate (LICAM); and 1,3,5-N,N',N"-tris(2,3-dihydroxybenzoyl)aminomethylbenzene (MECAM). A preferred chelator for use in the present invention is DTPA, and the use of DO3A is particularly preferred. Examples of representative chelators and chelating groups contemplated by the present invention are described in WO 98/18496, WO 86/06605, WO 91/03200, WO 95/28179, WO 96/23526, WO 97/36619, PCT/US98/01473, PCT/US98/20182, and U.S. Pat. Nos. 4,899,755, 5,474,756, 5,846,519 and 6,143,274, all of which are hereby incorporated by reference.

In accordance with the present invention, the chelator of the MRI contrast agent is coupled to the Akt capture agent. The positioning of the chelate should be selected so as not to interfere with the binding affinity or specificity of the Akt capture agent. The chelate also can be attached anywhere on the capture agent.

In general, the Akt capture agent can be bound directly or covalently to the metal chelator (or other detectable label), or it can be coupled or conjugated to the metal chelator using a linker, which can be, without limitation, amide, urea, acetal, ketal, double ester, carbonyl, carbamate, thiourea, sulfone, thioester, ester, ether, disulfide, lactone, imine, phosphoryl, or phosphodiester linkages; substituted or unsubstituted saturated or unsaturated alkyl chains; linear, branched, or cyclic amino acid chains of a single amino acid or different amino acids (e.g., extensions of the N- or C-terminus of the Akt binding moiety); derivatized or underivatized polyethylene glycols (PEGs), polyoxyethylene, or polyvinylpyridine chains; substituted or unsubstituted polyamide chains; derivatized or underivatized polyamine, polyester, polyethylenimine, polyacrylate, poly (vinyl alcohol), polyglycerol, or oligosaccharide (e.g., dextran) chains; alternating block copolymers; malonic, succinic, glutaric, adipic and pimelic acids; caproic acid; simple diamines and dialcohols; any of the other linkers disclosed herein; or any other simple polymeric linkers known in the art (see, for example, WO 98/18497 and WO 98/18496). Preferably the molecular weight of the linker can be tightly controlled. The molecular weights can range in size from less than 100 to greater than 1000. Preferably the molecular weight of the linker is less than 100. In addition, it can be desirable to utilize a linker that is biodegradable in vivo to provide efficient routes of excretion for the imaging reagents of the present invention. Depending on their location within the linker, such biodegradable functionalities can include ester, double ester, amide, phosphoester, ether, acetal, and ketal functionalities.

In general, known methods can be used to couple the metal chelate and the Akt capture agent using such linkers (WO 95/28967, WO 98/18496, WO 98/18497 and discussion therein). The Akt binding moiety can be linked through an N- or C-terminus via an amide bond, for example, to a metal coordinating backbone nitrogen of a metal chelate or to an acetate arm of the metal chelate itself. The present disclosure contemplates linking of the chelate on any position, provided the metal chelate retains the ability to bind the metal tightly in order to minimize toxicity.

MRI contrast reagents prepared according to the disclosures herein can be used in the same manner as conventional MRI contrast reagents. Certain MR techniques and pulse sequences can be preferred to enhance the contrast of the site to the background blood and tissues. These techniques include (but are not limited to), for example, black blood angiography sequences that seek to make blood dark, such as fast spin echo sequences (Alexander, A. et al., 1998. Magn. Reson. Med., 40: 298-310) and flow-spoiled gradient echo sequences (Edelman, R. et al., 1990. Radiology, 177: 45-50). These methods also include flow independent techniques that enhance the difference in contrast, such as inversion-recovery prepared or saturation-recovery prepared sequences that will increase the contrast between Akt-expressing tissue and background tissues. Finally, magnetization transfer preparations also can improve contrast with these agents (Goodrich, K. et al., 1996. Invest. Radia, 31: 323-32).

The labeled reagent is administered to the patient in the form of an injectable composition. The method of administering the MRI contrast agent is preferably parenterally, meaning intravenously, intraarterially, intrathecally, interstitially, or intracavitarilly. For imaging Akt-expressing tissues, such as tumors, intravenous or intraarterial administration is preferred. For MRI, it is contemplated that the subject will receive a dosage of contrast agent sufficient to enhance the MR signal at the site Akt expression by at least 10%. After injection with the Akt capture agent containing MRI reagent, the patient is scanned in the MRI machine to determine the location of any sites of Akt expression. In therapeutic settings, upon identification of a site of Akt expression (e.g., fluid or tissue), an anti-cancer agent (e.g., inhibitors of Akt) can be immediately administered, if necessary, and the patient can be subsequently scanned to visualize viral load.

B. Nuclear Imaging (Radionuclide Imaging) and Radiotherapy

The Akt capture agents of the invention can be conjugated with a radionuclide reporter appropriate for scintigraphy, SPECT, or PET imaging and/or with a radionuclide appropriate for radiotherapy. Constructs in which the Akt capture agents are conjugated with both a chelator for a radionuclide useful for diagnostic imaging and a chelator useful for radiotherapy are within the scope of the invention.

For use as a PET agent a peptide or multimeric polypeptide construct is complexed with one of the various positron emitting metal ions, such as $^{51}Mn$, $^{52}Fe$, $^{60}Cu$, $^{68}Ga$, $^{72}As$, $^{94m}Tc$, or $^{110}In$. The binding moieties of the invention can also be labeled by halogenation using radionuclides such as $^{18}F$, $^{124}I$, $^{125}I$, $^{131}I$, $^{123}I$, $^{77}Br$, and $^{76}Br$. Preferred metal radionuclides for scintigraphy or radiotherapy include $^{99m}Tc$, $^{51}Cr$, $^{67}Ga$, $^{68}Ga$, $^{47}Sc$, $^{51}Cr$, $^{167}Tm$, $^{141}Ce$, $^{111}In$, $^{168}Yb$, $^{175}Yb$, $^{140}La$, $^{90}Y$, $^{88}Y$, $^{153}Sm$, $^{166}Ho$, $^{165}Dy$, $^{166}Dy$, $^{62}Cu$, $^{64}Cu$, $^{67}Cu$, $^{97}Ru$, $^{103}Ru$, $^{186}Re$, $^{188}Re$, $^{203}Pb$, $^{211}Bi$, $^{212}Bi$, $^{213}Bi$, $^{214}Bi$, $^{105}Rh$, $^{109}Pd$, $^{117m}Sn$, $^{149}Pm$, $^{161}Tb$, $^{177}Lu$, $^{198}Au$ and $^{199}Au$. The choice of metal will be determined based on the desired therapeutic or diagnostic application. For example, for diagnostic purposes the preferred radionuclides include $^{64}Cu$, $^{67}Ga$, $^{68}Ga$, $^{99m}Tc$, and $^{111}In$. For therapeutic purposes, the preferred radionuclides include $^{64}Cu$, $^{90}Y$, $^{105}Rh$, $^{111}In$, $^{117m}Sn$, $^{149}Pm$, $^{153}Sm$, $^{161}Tb$, $^{166}Tb$, $^{166}Dy$, $^{166}Ho$, $^{175}Yb$, $^{177}Ln$, $^{186/188}Re$, and $^{199}Au$. $^{99m}Tc$ is useful for diagnostic applications because of its low cost, availability, imaging properties, and high specific activity. The nuclear and radioactive properties of $^{99m}Tc$ make this isotope an ideal scintigraphic imaging agent. This isotope has a single photon energy of 140 keV and a radioactive half-life of about 6 hours, and is readily available from a $^{99}Mo$-$^{99m}Tc$ generator. $^{18}F$, 4-[$^{18}F$]fluorobenzaldehyde ($^{18}FB$), Al[$^{18}F$]-NOTA, $^{68}Ga$-DOTA, and $^{68}Ga$-NOTA are typical radionuclides for conjugation to Akt capture agents for diagnostic imaging.

The metal radionuclides may be chelated by, for example, linear, macrocyclic, terpyridine, and $N_3S$, $N_2S_2$, or $N_4$ chelants (see also, U.S. Pat. Nos. 5,367,080, 5,364,613, 5,021,556, 5,075,099, 5,886,142), and other chelators known in the art including, but not limited to, HYNIC, DTPA, EDTA, DOTA, DO3A, TETA, NOTA and bisamino bisthiol (BAT) chelators (see also U.S. Pat. No. 5,720,934). For example, N.sub.4 chelators are described in U.S. Pat. Nos. 6,143,274; 6,093,382; 5,608,110; 5,665,329; 5,656,254; and 5,688,487. Certain $N_3S$ chelators are described in PCT/CA94/00395, PCT/CA94/00479, PCT/CA95/00249 and in U.S. Pat. Nos. 5,662,885; 5,976,495; and 5,780,006. The chelator also can include derivatives of the chelating ligand mercapto-acetyl-acetyl-glycyl-glycine (MAG3), which contains an $N_3S$, and $N_2S_2$ systems such as MAMA (monoamidemonoaminedithiols), DADS ($N_2S$ diaminedithiols), CODADS and the like. These ligand systems and a variety of others are described in, for example, Liu, S, and Edwards, D., 1999. Chem. Rev., 99:2235-2268, and references therein.

The chelator also can include complexes containing ligand atoms that are not donated to the metal in a tetradentate array. These include the boronic acid adducts of technetium and rhenium dioximes, such as are described in U.S. Pat. Nos. 5,183,653; 5,387,409; and 5,118,797, the disclosures of which are incorporated by reference herein, in their entirety.

The chelators can be covalently linked directly to the Akt capture agent via a linker, as described previously, and then directly labeled with the radioactive metal of choice (see, WO 98/52618, U.S. Pat. Nos. 5,879,658, and 5,849,261).

Akt capture agents comprising $^{18}F$, 4-[$^{18}F$]fluorobenzaldehyde ($^{18}FB$), Al[$^{18}F$]-NOTA, $^{68}Ga$-DOTA, and $^{68}Ga$-NOTA are of preferred interest for diagnostic imaging. Complexes of radioactive technetium are also useful for diagnostic imaging, and complexes of radioactive rhenium are particularly useful for radiotherapy. In forming a complex of radioactive technetium with the reagents of this invention, the technetium complex, preferably a salt of $^{99m}Tc$ pertechnetate, is reacted with the reagent in the presence of a reducing agent. Preferred reducing agents are dithionite, stannous and ferrous ions; the most preferred reducing agent is stannous chloride. Means for preparing such complexes are conveniently provided in a kit form comprising a sealed vial containing a predetermined quantity of a reagent of the invention to be labeled and a sufficient amount of reducing agent to label the reagent with $^{99m}Tc$. Alternatively, the complex can be formed by reacting a peptide of this invention conjugated with an appropriate chelator with a pre-formed labile complex of technetium and another compound known as a transfer ligand. This process is known as ligand exchange and is well known to those skilled in the art. The labile complex can be formed using such transfer ligands as tartrate, citrate, gluconate or mannitol, for example. Among the $^{99m}Tc$ pertechnetate salts useful with the present invention are included the alkali metal salts such as the sodium salt, or ammonium salts or lower alkyl ammonium salts.

Preparation of the complexes of the present invention where the metal is radioactive rhenium can be accomplished using rhenium starting materials in the +5 or +7 oxidation state. Examples of compounds in which rhenium is in the Re(VII) state are $NH_4ReO_4$ or $KReO_4$. $R_e(V)$ is available as, for example, [$ReOCl_4$](NBu$_4$), [$ReOCl_4$](AsPh$_4$), $ReOCl_3$(PPh$_3$)$_2$ and as $ReO_2$(pyridine)$_4^{4+}$, where Ph is phenyl and Bu is n-butyl. Other rhenium reagents capable of forming a rhenium complex also can be used.

Radioactively labeled PET, SPECT, or scintigraphic imaging agents provided by the present invention are encompassed having a suitable amount of radioactivity. Generally, the unit dose to be administered has a radioactivity of about 0.01 mCi to about 100 mCi, preferably 1 mCi to 20 mCi. The solution to be injected at unit dosage is from about 0.01 mL to about 10 mL. It is generally preferred to form radioactive complexes in solutions containing radioactivity at concentrations of from about 0.01 mCi to 100 mCi per mL.

Typical doses of a radionuclide-labeled Akt capture agent according to the invention provide 10-20 mCi. After injection of the radionuclide-labeled Akt capture agents into the patient, a gamma camera calibrated for the gamma ray energy of the nuclide incorporated in the imaging agent is used to image areas of uptake of the agent and quantify the amount of radioactivity present in the site. Imaging of the site in vivo can take place in a matter of a few minutes. However, imaging can take place, if desired, in hours or even longer, after the radiolabeled peptide is injected into a patient. In most instances, a sufficient amount of the administered dose will accumulate in the area to be imaged within about 0.1 of an hour to permit the taking of scintiphotos.

Proper dose schedules for the radiotherapeutic compounds of the present invention are known to those skilled in the art. The compounds can be administered using many methods including, but not limited to, a single or multiple IV or IP injections, using a quantity of radioactivity that is sufficient to cause damage or ablation of the targeted Akt-expressing tissue, but not so much that substantive damage is caused to non-target (normal tissue). The quantity and dose required is different for different constructs, depending on the energy and half-life of the isotope used, the degree of uptake and clearance of the agent from the body and the mass of the Akt-expressing tissue. In general, doses can range from a single dose of about 30-50 mCi to a cumulative dose of up to about 3 Ci.

The radiotherapeutic compositions of the invention can include physiologically acceptable buffers, and can require radiation stabilizers to prevent radiolytic damage to the compound prior to injection. Radiation stabilizers are known to those skilled in the art, and can include, for example, para-aminobenzoic acid, ascorbic acid, gentistic acid and the like.

A single, or multi-vial kit that contains all of the components needed to prepare the complexes of this invention, other than the radionuclide, is an integral part of this invention.

A single-vial kit preferably contains a chelating ligand, a source of stannous salt, or other pharmaceutically acceptable reducing agent, and is appropriately buffered with pharmaceutically acceptable acid or base to adjust the pH to a value of about 3 to about 9. The quantity and type of reducing agent used would depend on the nature of the exchange complex to be formed. The proper conditions are well known to those that are skilled in the art. It is preferred that the kit contents be in lyophilized form. Such a single vial kit can optionally contain labile or exchange ligands such as glucoheptonate, gluconate, mannitol, malate, citric or tartaric acid and can also contain reaction modifiers such as diethylenetriamine-pentaacetic acid (DPTA), ethylenediamine tetraacetic acid (EDTA), or a, β, or γ cyclodextrin that serve to improve the radiochemical purity and stability of the final product. The kit also can contain stabilizers, bulking agents such as mannitol, that are designed to aid in the freeze-drying process, and other additives known to those skilled in the art.

A multi-vial kit preferably contains the same general components but employs more than one vial in reconstituting the radiopharmaceutical. For example, one vial can contain all of the ingredients that are required to form a labile Tc(V) complex on addition of pertechnetate (e.g., the stannous source or other reducing agent). Pertechnetate is added to this vial, and after waiting an appropriate period of time, the contents of this vial are added to a second vial that contains the ligand, as well as buffers appropriate to adjust the pH to its optimal value. After a reaction time of about 5 to 60 minutes, the complexes of the present invention are formed. It is advantageous that the contents of both vials of this multi-vial kit be lyophilized. As above, reaction modifiers, exchange ligands, stabilizers, bulking agents, etc. can be present in either or both vials.

Also provided herein is a method to incorporate an $^{18}$F radiolabeled prosthetic group onto an Akt capture agent. In one embodiment, 4-[$^{18}$F]fluorobenzaldehyde ($^{18}$FB) is conjugated onto a capture agent bearing an aminooxy moiety, resulting in oxime formation. In another embodiment, [$^{18}$F]fluorobenzaldehyde is conjugated onto a capture agent bearing an acyl hydrazide moiety, resulting in a hydrazone adduct. 4-Fluorobenzaldehyde, can be prepared in $^{18}$F form by displacement of a leaving group, using $^{18}$F ion, by known methods.

$^{18}$F-labeled capture agents can also be prepared from capture agents possessing thiosemicarbazide moieties under conditions that promote formation of a thiosemicarbozone, or by use of a $^{18}$F-labeled aldehyde bisulfite addition complex.

The above methods are particularly amenable to the labeling of capture agents, e.g., the capture agents described herein, which can be modified during synthesis to contain a nucleophilic hydroxylamine, thiosemicarbazide or hydrazine (or acyl hydrazide) moiety that can be used to react with the labeled aldehyde. The methods can be used for any capture agent that can accommodate a suitable nucleophilic moiety. Typically the nucleophilic moiety is appended to the N-terminus of the peptide, but the skilled artisan will recognize that the nucleophile also can be linked to an amino acid side chain or to the peptide C-terminus. Methods of synthesizing a radiolabeled peptide sequence are provided in which 4-[$^{18}$F]fluorobenzaldehyde is reacted with a peptide sequence comprising either a hydroxylamine, a thiosemicarbazide or a hydrazine (or acyl hydrazide) group, thereby forming the corresponding oximes, thiosemicarbazones or hydrazones, respectively. The 4-[$^{18}$F]fluorobenzaldehyde typically is generated in situ by the acid-catalyzed decomposition of the addition complex of 4-[$^{18}$F]fluorobenzaldehyde and sodium bisulfite. The use of the bisulfite addition complex enhances the speed of purification since, unlike the aldehyde, the complex can be concentrated to dryness. Formation of the complex is also reversible under acidic and basic conditions. In particular, when the complex is contacted with a peptide containing a hydroxylamine, a thiosemicarbazide or a hydrazine (or acyl hydrazide) group in acidic medium, the reactive free 4-[$^{18}$F]fluorobenzaldehyde is consumed as it is formed in situ, resulting in the corresponding F-18 radiolabeled peptide sequence.

In the instances when the oxime, thiosemicarbazone or hydrazone linkages present in vivo instability, an additional reduction step may be employed to reduce the double bond connecting the peptide to the F-18 bearing substrate. The corresponding reduced peptide linkage would enhance the stability. One of skill in the art would appreciate the variety of methods available to carry out such a reduction step. Reductive amination steps as described in Wilson et al., Journal of Labeled Compounds and Radiopharmaceuticals, XXVIII (10), 1189-1199, 1990 may also be used to form a Schiff's base involving a peptide and 4-[$^{18}$F]fluorobenzaldehyde and directly reducing the Schiff's base using reducing agents such as sodium cyanoborohydride.

The 4-[$^{18}$F]fluorobenzaldehyde may be prepared as described in Wilson et al., Journal of Labeled Compounds and Radiopharmaceuticals, XXVIII (10), 1189-1199, 1990; Iwata et al., Applied radiation and isotopes, 52, 87-92, 2000; Poethko et al., The Journal of Nuclear Medicine, 45, 892-902, 2004; and Schottelius et al., Clinical Cancer Research, 10, 3593-3606, 2004. The Na.sup.18F in water may be added to a mixture of kryptofix and $K_2CO_3$. Anhydrous acetonitrile may be added and the solution is evaporated in a heating block under a stream of argon. Additional portions of acetonitrile may be added and evaporated to completely dry the sample. The 4-trimethylammoniumbenzaldehyde triflate may be dissolved in DMSO and added to the dried F-18. The solution may then be heated in the heating block. The solution may be cooled briefly, diluted with water and filtered through a Waters® Oasis HLB LP extraction cartridge. The cartridge may be washed with 9:1 water:acetonitrile and water to remove unbound F-18 and unreacted 4-trimethylammoniumbenzaldehyde triflate. The 4-[$^{18}$F] fluorobenzaldehyde may then be eluted from the cartridge with methanol in fractions.

Therapeutic Applications

Provided herein in certain embodiments are methods of using the Akt capture agents disclosed herein to identify, detect, quantify, and/or separate Akt in a biological sample. In certain embodiments, these methods utilize an immunoassay, with the capture agent replacing an antibody or its equivalent. In certain embodiments, the immunoassay may be a Western blot, pull-down assay, dot blot, or ELISA.

A biological sample for use in the methods provided herein may be selected from the group consisting of organs, tissue, bodily fluids, and cells. Where the biological sample is a bodily fluid, the fluid may be selected from the group consisting of blood, serum, plasma, urine, sputum, saliva, stool, spinal fluid, cerebral spinal fluid, lymph fluid, skin secretions, respiratory secretions, intestinal secretions, genitourinary tract secretions, tears, and milk. The organs include, e.g., the adrenal glands, bladder, bones, brain, breasts, cervix, esophagus, eyes, gall bladder, genitals, heart, kidneys, large intestine, liver, lungs, lymph nodes, ovaries, pancreas, pituitary gland, prostate, salivary glands, skeletal muscles, skin, small intestine, spinal cord, spleen, stomach, thymus gland, trachea, thyroid, testes, ureters, and urethra. Tissues include, e.g., epithelial, connective, nervous, and muscle tissues.

Provided herein in certain embodiments are methods of using the Akt capture agents disclosed herein to diagnose and/or classify (e.g., stage) a condition associated with Akt expression, including for example various cancers. In certain of these embodiments, the methods comprise (a) obtaining a biological sample from a subject; (b) measuring the presence or absence of Akt in the sample with the Akt capture agent; (c) comparing the levels of Akt to a predetermined control range for Akt; and (d) diagnosing a condition associated with Akt expression based on the difference between Akt levels in the biological sample and the predetermined control.

In other embodiments, the Akt capture agents disclosed herein are used as a mutant specific targeted therapeutic. In certain aspects of this embodiment, the Akt capture agent is administered alone without delivering DNA, a radiopharmaceutical or another active agent. In certain embodiments, administration of one or more of the Akt capture agents disclosed herein should decrease the phosphorylation/activation of proliferation-inducing E17K Akt1 in mutant cells.

The Akt capture agents of the invention also can be used to target genetic material to Akt expressing cells. Thus, they can be useful in gene therapy, particularly for treatment of cancer. In this embodiment, genetic material or one or more delivery vehicles containing genetic material useful in treating cancer can be conjugated to one or more Akt capture agents of the disclosure and administered to a patient. The genetic material can include nucleic acids, such as RNA or DNA, of either natural or synthetic origin, including recombinant RNA and DNA and antisense RNA and DNA. Types of genetic material that can be used include, for example, genes carried on expression vectors such as plasmids, phagemids, cosmids, yeast artificial chromosomes (YACs) and defective or "helper" viruses, antigene nucleic acids, both single and double stranded RNA and DNA and analogs thereof, such as phosphorothioate and phosphorodithioate oligodeoxynucleotides. Additionally, the genetic material can be combined, for example, with lipids, proteins or other polymers. Delivery vehicles for genetic material can include, for example, a virus particle, a retroviral or other gene therapy vector, a liposome, a complex of lipids (especially cationic lipids) and genetic material, a complex of dextran derivatives and genetic material, etc.

In an embodiment the capture agents of the invention are utilized in gene therapy for treatment of cancer. In this embodiment, genetic material, or one or more delivery vehicles containing genetic material, e.g., useful in treating cancer, can be conjugated to one or more Akt capture agents of this disclosure and administered to a patient.

Constructs including genetic material and Akt capture agents of this disclosure can be used, in particular, to selectively introduce genes into proliferating cancer cells (e.g., epithelial cells), which can be useful to treat cancer.

Therapeutic agents and the Akt capture agents disclosed herein can be linked or fused in known ways, optionally using the same type of linkers discussed elsewhere in this application. Preferred linkers will be substituted or unsubstituted alkyl chains, amino acid chains, polyethylene glycol chains, and other simple polymeric linkers known in the art. More preferably, if the therapeutic agent is itself a protein, for which the encoding DNA sequence is known, the therapeutic protein and Akt binding polypeptide can be coexpressed from the same synthetic gene, created using recombinant DNA techniques, as described above. The coding sequence for the Akt binding polypeptide can be fused in frame with that of the therapeutic protein, such that the peptide is expressed at the amino- or carboxy-terminus of the therapeutic protein, or at a place between the termini, if it is determined that such placement would not destroy the required biological function of either the therapeutic protein or the Akt binding polypeptide. A particular advantage of this general approach is that concatamerization of multiple, tandemly arranged Akt capture agents is possible, thereby increasing the number and concentration of Akt binding sites associated with each therapeutic protein. In this manner, Akt binding avidity is increased, which would be expected to improve the efficacy of the recombinant therapeutic fusion protein.

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Other tags that can be used to provide degradation signals include nutlin-3 (Schneekloth, et al. Bioorg. Med. Chem. Lett. 18, 5904-5908 (2008)); Boc3Arginine (Long, et al. Chem. Biol. 19, 629-637 (2012)); methyl bestatin (Itoh, et al. J. Am. Chem. Soc. 132, 5820-5826 (2010)); HyT13 or HyT36 (Tae, et al. ChemBioChem 13, 538-541 (2012)); HIF-1a VHL binding peptides (Hines, et al. Proc. Natl. Acad. Sci. 110, 8942-8947 (2013) and Sakamoto, et al. Mol. Cell. Proteomics 2, 1350-1358 (2003)); lysosomal-targeting peptide derived from Rhase A, hsc 70 and hemoglobin (Fan, et al. Nat. Neurosci. 17, 471-480 (2014)); amd SCFTrCP-targeting IκBα phosphopeptide (Sakamoto, et al. Proc. Natl. Acad. Sci. 98, 8554-8559 (2001)) Each of the references cited in the paragraph are incorporated by reference herein in their entireties.

EXAMPLES

Figure 6:
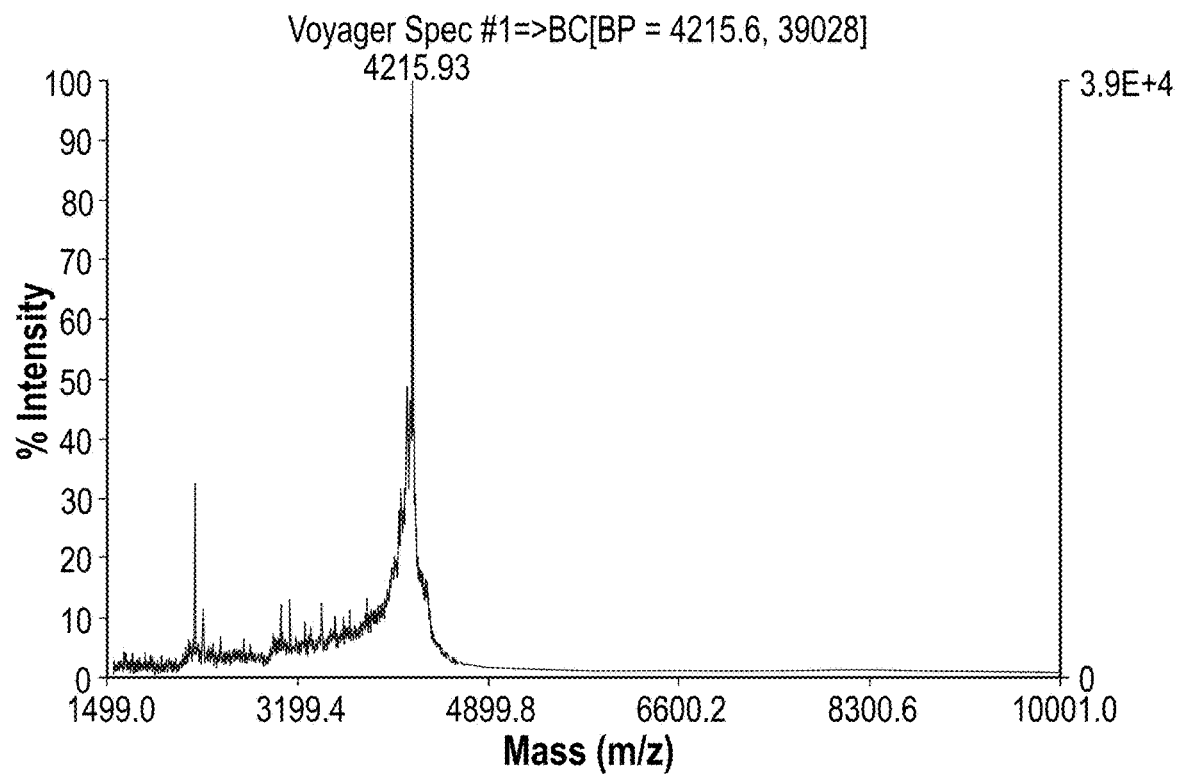
FIG. 6 is a line graph showing MALDI-TOF analysis of a 33-mer target fragment. Sequence: Biotin-MSDVAIVKEGWLKKRGKY[Pra]KTWRPRYFLLKNDG (SEQ ID NO: 1). Expected m/z: 4214.9, observed M+H: 4215.93
Figure 7:
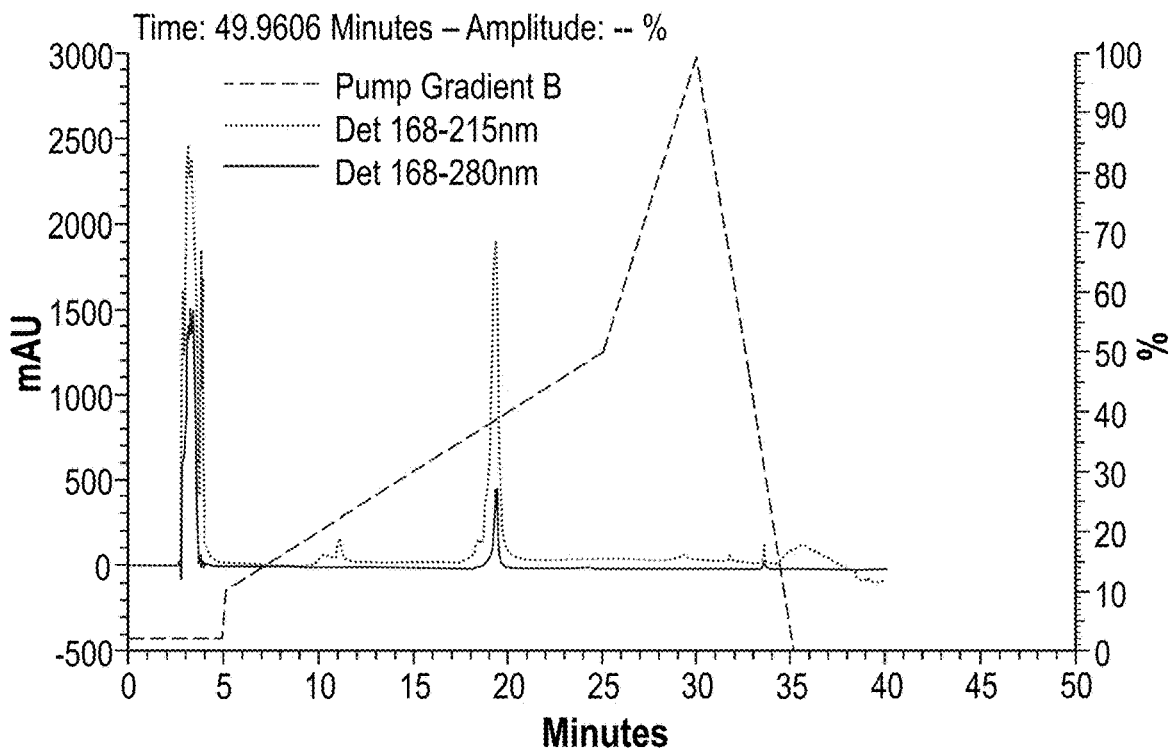
FIG. 7 is an HPLC trace demonstrating purity of 33-mer E17K Fragment. The 33-mer fragment dissolved in buffer was run on an analytical HPLC to demonstrate the purity of the peptide that was analyzed by MALDI in FIG. 6. The peak below 5 minutes is the salt from the buffer.

Example 1. In Situ Click Epitope-Targeted Screening Strategy for E17K PH Domain-Specific Ligand Using FMOC SPPS peptide synthesis techniques[18] a peptide epitope representing residues 1-32 of the E17K PH Domain of Akt1 was synthesized. From the crystal structure (2UZR) (FIG. 1), these residues form a β-sheet around the E17K mutation. The epitope fragment was appended with an N-terminal PEG$_5$-biotin to serve as a detection handle when screening. This manual synthesis of the epitope allowed for an I19Pra substitution (Pra=propargylglycine) to provide an alkyne click handle on the most proximal side-chain residue to the E17K mutation. Following chromatographic purification, and characterization via mass spectrometry (FIG. 6), HPLC (FIG. 7) and circular dichroism (FIG. 8), the modified epitope was ready for screening.

A single generation in situ click screen can yield ligands with a high selectivity for the target. Hits from such a screen are those library elements that are covalently coupled to the synthetic epitope through a triazole linkage. The in situ click reaction itself is low yielding[14], but the biotin handle on the synthetic epitope permits enzymatic amplification of those hit beads using a colorimetric streptavidin-linked alkaline phosphatase assay. The basic screening strategy is shown in FIG. 9. Out of the 1.5 million library members that were screened against the alkyne-containing 33-mer E17K PH Domain fragment, only 21 beads (0.0014%) showed the presence of the covalently coupled epitope. These beads were sequenced using Edman degradation (Tables 1 and 2).

TABLE 1

Hit sequences from Anchor Screen Against 33-mer Epitope (5hr)

| Az2 | G | v | e | k | f | SEQ ID NO: 48 |
|---|---|---|---|---|---|---|
| Az8 | y | h | e | w | f | SEQ ID NO: 45 |
| Az4 | i | s | e | y | e | SEQ ID NO: 22 |
| Az2 | p | h | w | l/k | f | SEQ ID NO: 79 |
| Az8 | d | l | l | t | f | SEQ ID NO: 42 |

TABLE 1-continued

Hit sequences from Anchor Screen Against 33-mer Epitope (5hr)

| Az4 | a | r | s | d | f | SEQ ID NO: 49 |
|---|---|---|---|---|---|---|
| Az8 | f | k/l |   | G | t | SEQ ID NO: 80 |
| Az8 | f | e | i | q |   | SEQ ID NO: 81 |
| Az8 | e | e | p | d/n | f | SEQ ID NO: 82 |

TABLE 2

Hit Sequences from Anchor Screen Against 33-mer Fragment (overnight)

| Az4 | e | e | f | e | f | SEQ ID NO: 77 |
|---|---|---|---|---|---|---|
| Az8 | f | e | e | a | i | SEQ ID NO: 83 |
| Az2 | e | l | n | h | y | SEQ ID NO: 41 |
| Az2 | h | a | r | h | q | SEQ ID NO: 32 |
| Az2 | h | e | w | v | t | SEQ ID NO: 34 |
| Az4 | n | w | y | a | w | SEQ ID NO: 84 |
| Az4 | n | l | v | p | n | SEQ ID NO: 85 |
| Az2 |   | r | r | r | f | SEQ ID NO: 86 |
| Az4 | a | l | n | s | k | SEQ ID NO: 24 |
| Az8 | p |   | a | y | h | SEQ ID NO: 87 |
| Az2 | n | r | y | v | r | SEQ ID NO: 25 |
| Az8 | y | l | e | a | f | SEQ ID NO: 43 |

Figure 14:
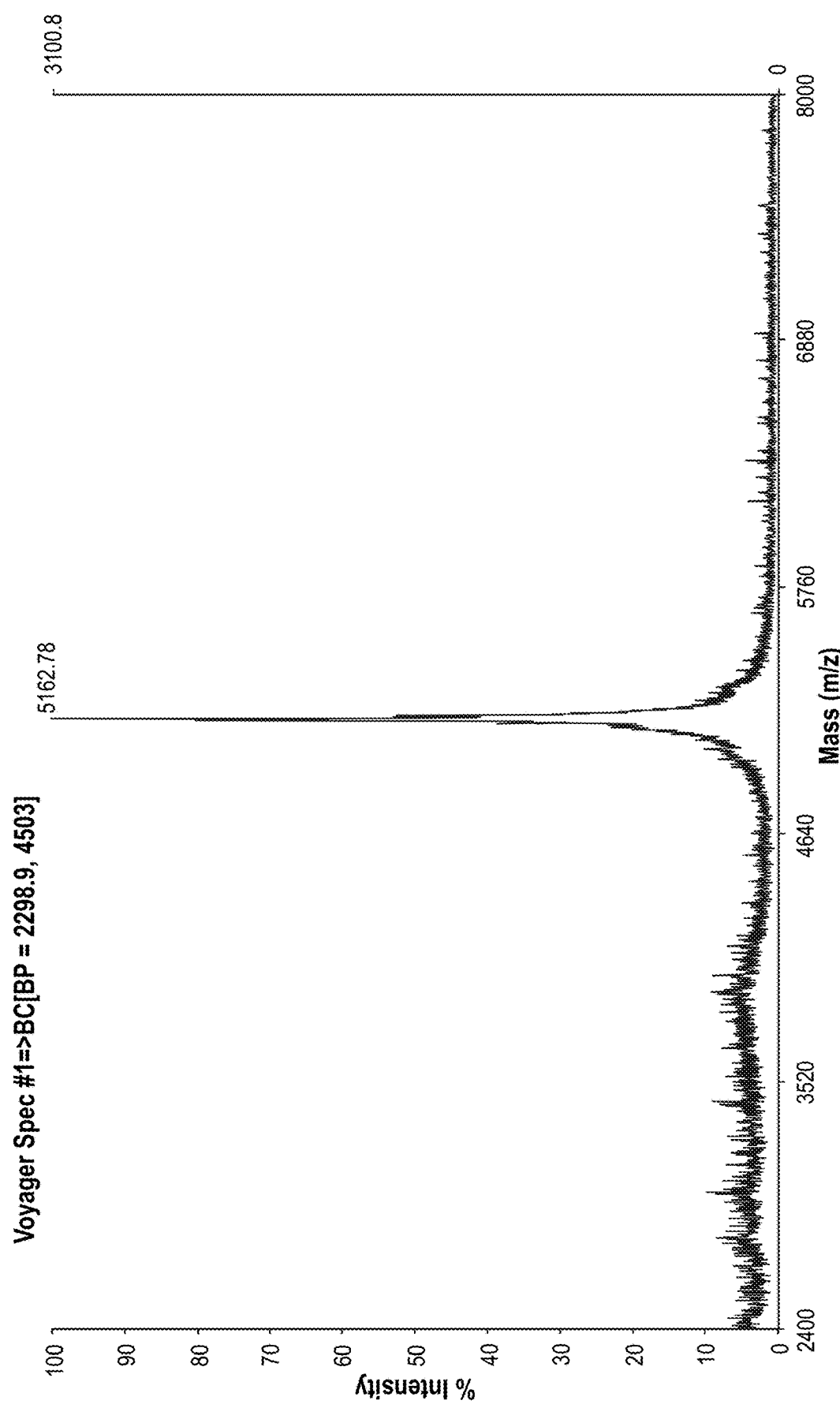
FIG. 14 is a chart showing MALDI-TOF of 6His (SEQ ID NO: 4)-PEG5-WT 33mer Fragment ("6 His" disclosed as SEQ ID NO: 4): Sequence: HHHHHH-PEG5-MSDVAIVKEGWLKKRGKY[Pra]KTWRPRYFLLKNDG (SEQ ID NOS 4 and 1, respectively, in order of appearance). Expected: 5161.72, observed: 5162.78.
Figure 15:
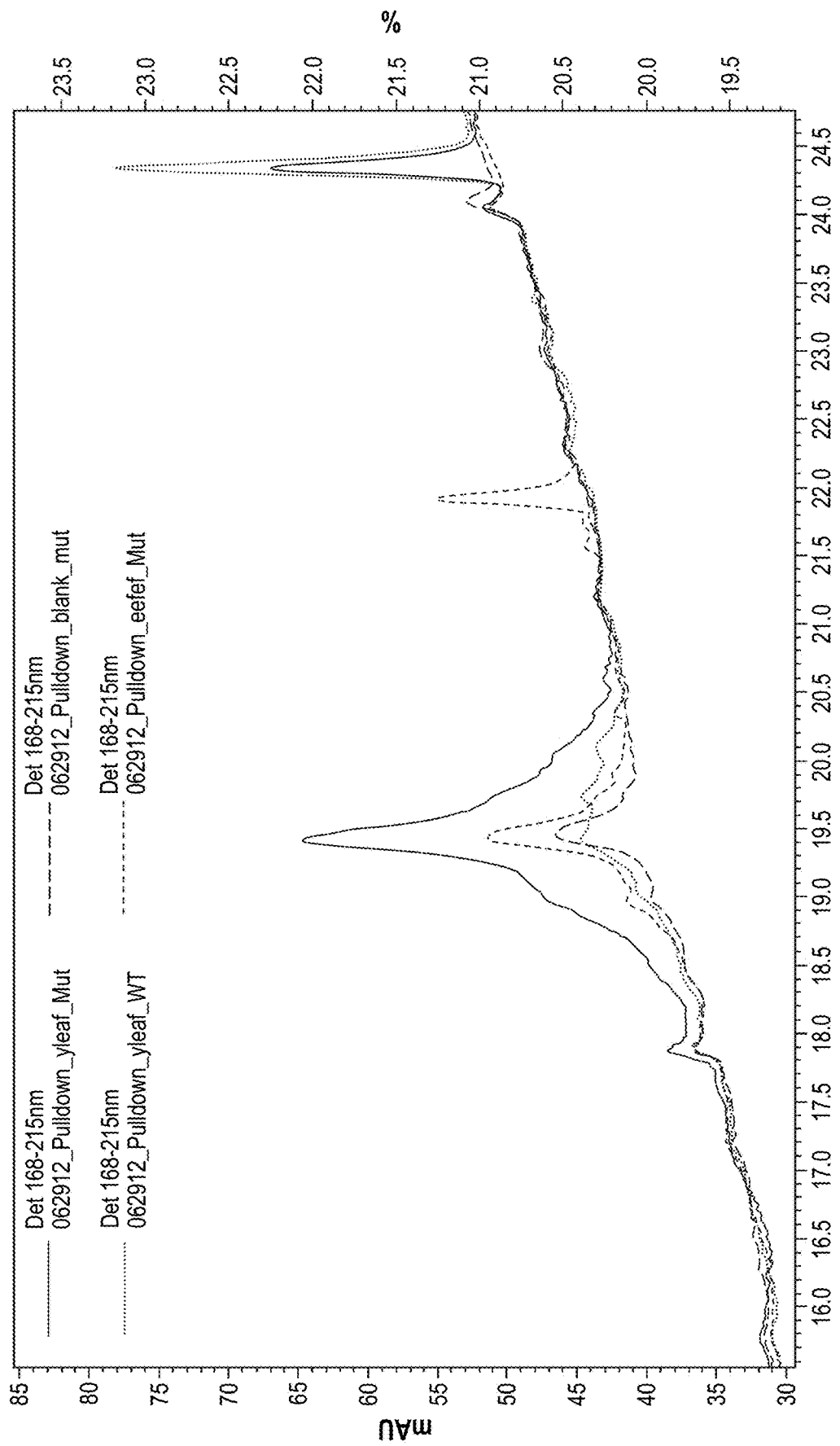
FIG. 15 is a line graph showing HPLC-detected Immunoprecipitation (Pulldown) Assays for Epitope Targeting Verification: The major peak indicated by "33-mer" demonstrates the amount of 33-mer fragment that was pulled down by either the "yleaf" (SEQ ID NO: 43) anchor ligand or an off-target ligand "eefef" (SEQ ID NO: 77), both of which can be seen in the HPLC due to the Guanadine elution stripping them from the resin with the fragment. In this assay, the yleaf (SEQ ID NO: 43) anchor ligand clearly pulls down the most of the E17K 33mer fragment (pink), and the least of the WT fragment (cyan). The eefef (SEQ ID NO: 77) off-target fragment should not have much binding to the E17K fragment, as seen in lane 4 and shows much less pull down than the yleaf (SEQ ID NO: 43) anchor protein in this assay, as well.

The hits were segregated based on their hydrophobicity and sequence homology using principal component analysis (FIG. 10). Five ligands that represented the diversity of hits (circled in FIG. 10) were scaled-up and tested for binding to both E17K and WT full-length PHD. Immunoprecipitation assays (FIG. 11) were used to probe for differential binding to the proteins in buffer. One ligand candidate showed a distinctively stronger binding to the E17K protein relative to the WT. This peptide, sequence "yleaf" (SEQ ID NO: 43), (FIG. 1b) was carried forward for additional investigations. Here the lower case sequence letters indicate that the amino acids that comprise the peptide are non-natural D-stereoisomers. Verification of epitope targeting strategy The label-modified yleaf (SEQ ID NO: 43) peptide (FIG. 2a and FIG. 12) was subjected to a variety of binding assays against the synthesized WT and E17K 33-mer PHD fragments prepared without the biotin label and alkyne click handle. First, the yleaf (SEQ ID NO: 43) peptide was used in immunoprecipitation assays to pull-down either the WT or E17K mutant 6His-tagged (SEQ ID NO: 4) 33-mer peptide fragments (FIGS. 13 and 14), as opposed to the full-length proteins that were used to initially validate the candidates. Typical immunoprecipitation assays involve western blotting to estimate the amount of protein binding, but 33-mer peptide fragments are not easily quantified on a blot. Because of this, the amount of peptide epitope precipitated in these assays was quantified via injection on an analytical HPLC. These assays further confirmed preferential yleaf (SEQ ID NO: 43) ligand binding to the E17K 33-mer epitope relative to the WT epitope (FIG. 15). As an assay control, another candidate ligand that, in initial testing, did not exhibit preferential E17K binding to the full protein, was tested, and yielded consistent results.

The selectivity of the yleaf (SEQ ID NO: 43) peptide for the E17K 33-mer epitope was also tested in an ELISA assay format. For these assays, the WT or E17K 33-mer peptide fragments were captured using the PEG-biotin-modified yleaf (SEQ ID NO: 43) ligand immobilized on a neutravidin-coated plate. The yleaf (SEQ ID NO: 43) ligand exhibited significant selectivity for the E17K fragment over the WT across a 100 nM-1 µM concentration range (FIG. 2b This selectivity was quantified by measuring the $K_D$ values for the binding of the yleaf (SEQ ID NO: 43) peptide 4 to both epitope fragments (FIG. 2d), as well as full length Akt1 and Akt1E17K (FIG. 2c) via fluorescence polarization (FP). The yleaf (SEQ ID NO: 43) peptide exhibited $K_D$ values of 328±96 nM and 54±7.0 nM for the mutant epitope and for full length Akt1E17K, respectively. These compare to $K_D$ values of 2.8±0.84 µM and >1 µM shown for the WT epitopes and Akt1, respectively. These results confirm the highly selective nature of the epitope targeting strategy, and demonstrate that high selectivity achieved through that strategy is retained for the full length protein.

Ligand-Directed Labeling Experiment to Confirm Selectivity and Epitope Targeting The selectivity of the yleaf ligand was further verified using the directed labeling technique reported by Tsukiji et al[19]. The approach yields information relative to the binding location of the ligand on the protein target. For this method, a payload is attached to the N-terminus of the targeting yleaf ligand through an electrophilic tosylate linker. Upon ligand binding to the protein target, the payload is transferred onto the protein through a nucleophilic $S_N2$ reaction with proximal nucleophilic amino acid side chains (FIG. 3a). The protein can then be trypsin digested and the identity of the fragments containing the payload can be mapped on the protein surface using mass spectrometry (MS). Thus, the site of ligand binding can be estimated. The assay also serves as an independent validation of the immunoprecipitation and ELISA binding assays discussed above.

Figure 2A:
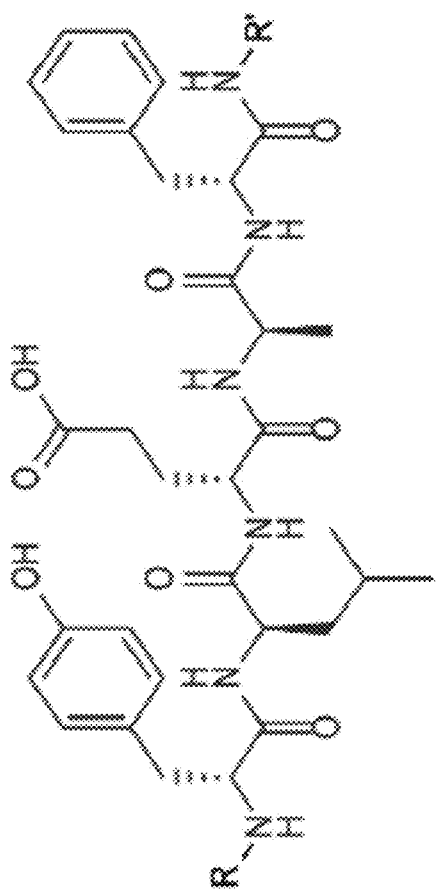
(FIG. 2A) The peptide anchor ligand, yleaf (SEQ ID NO: 43), which was discovered using the epitope-targeting technique. The different sets of R groups indicate the modifications that were made to perform the various experiments described.
Figure 2B:
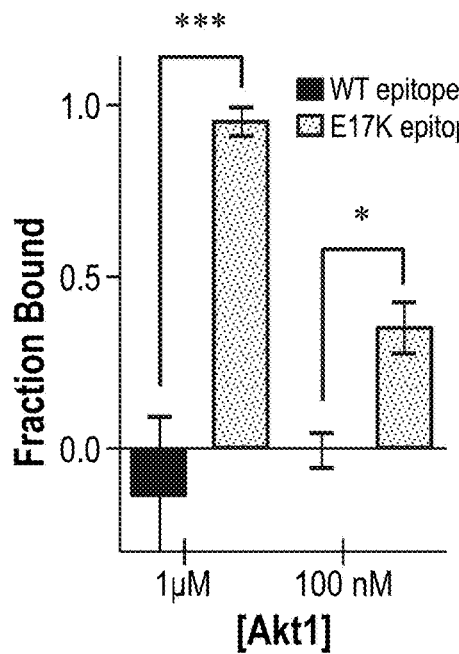
(FIG. 2B) Point ELISA for specificity obtained by immobilizing biotinylated yleaf (SEQ ID NO: 43) anchor ligand 2 onto a Neutravidin plate, then incubating with a 6 His-tagged epitope ("6 His" disclosed as SEQ ID NO: 4) 3. This assay demonstrates the preference of the biotinylated yleaf (SEQ ID NO: 43) anchor ligand for the E17K mutant epitope while immobilized on a surface.
Figure 2C:
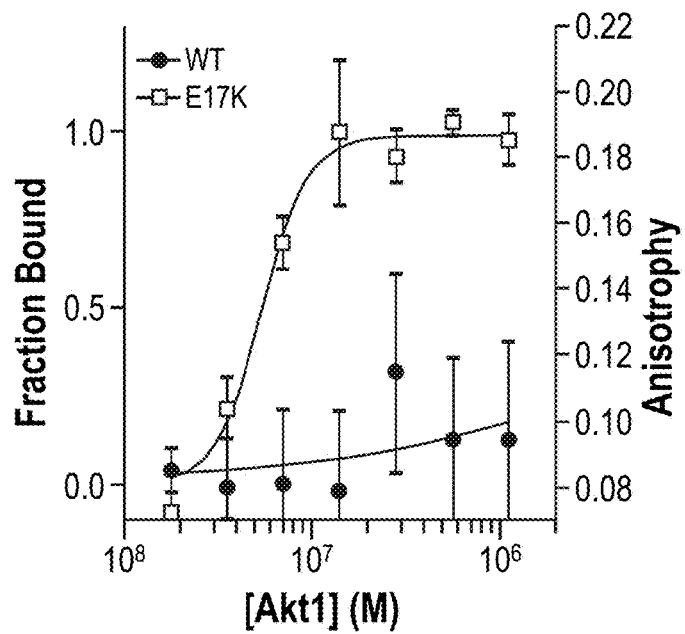
(FIG. 2C) Binding curves of yleaf (SEQ ID NO: 43) anchor ligand 4 to the full-length WT or E17K mutant Akt1 proteins obtained in solution by fluorescence polarization. A saturation point for the WT ligand was not reached due to the prohibitively high protein concentration required.
Figure 2D:
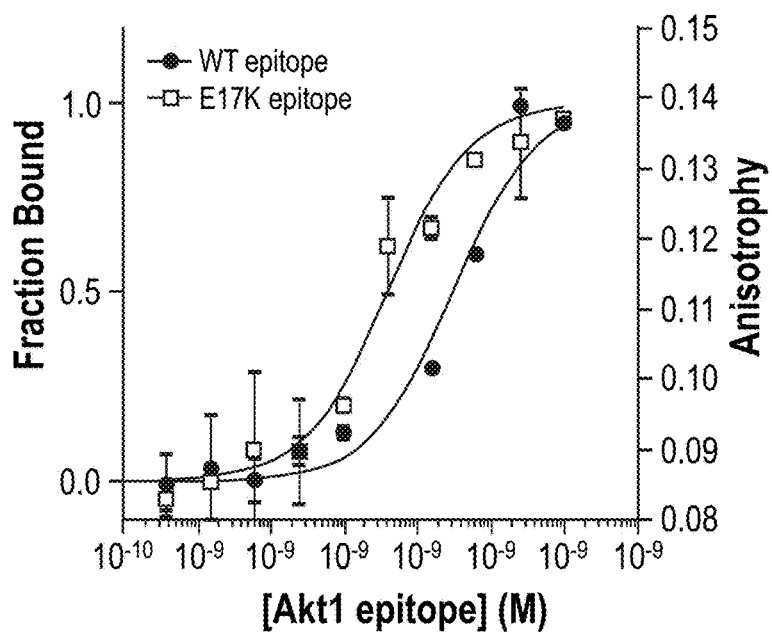
(FIG. 2D) Full binding curves of yleaf (SEQ ID NO: 43) anchor ligand 4 to the WT or E17K mutant epitopes. These fluorescence polarization curves demonstrate the significant preference of the yleaf (SEQ ID NO: 43) ligand for the E17K mutation in both the full protein assay (FIG. 2C) and the epitope peptide assay (FIG. 2D). All assays were performed in triplicate and averaged. Error bars indicate standard deviation.
Figure 16:
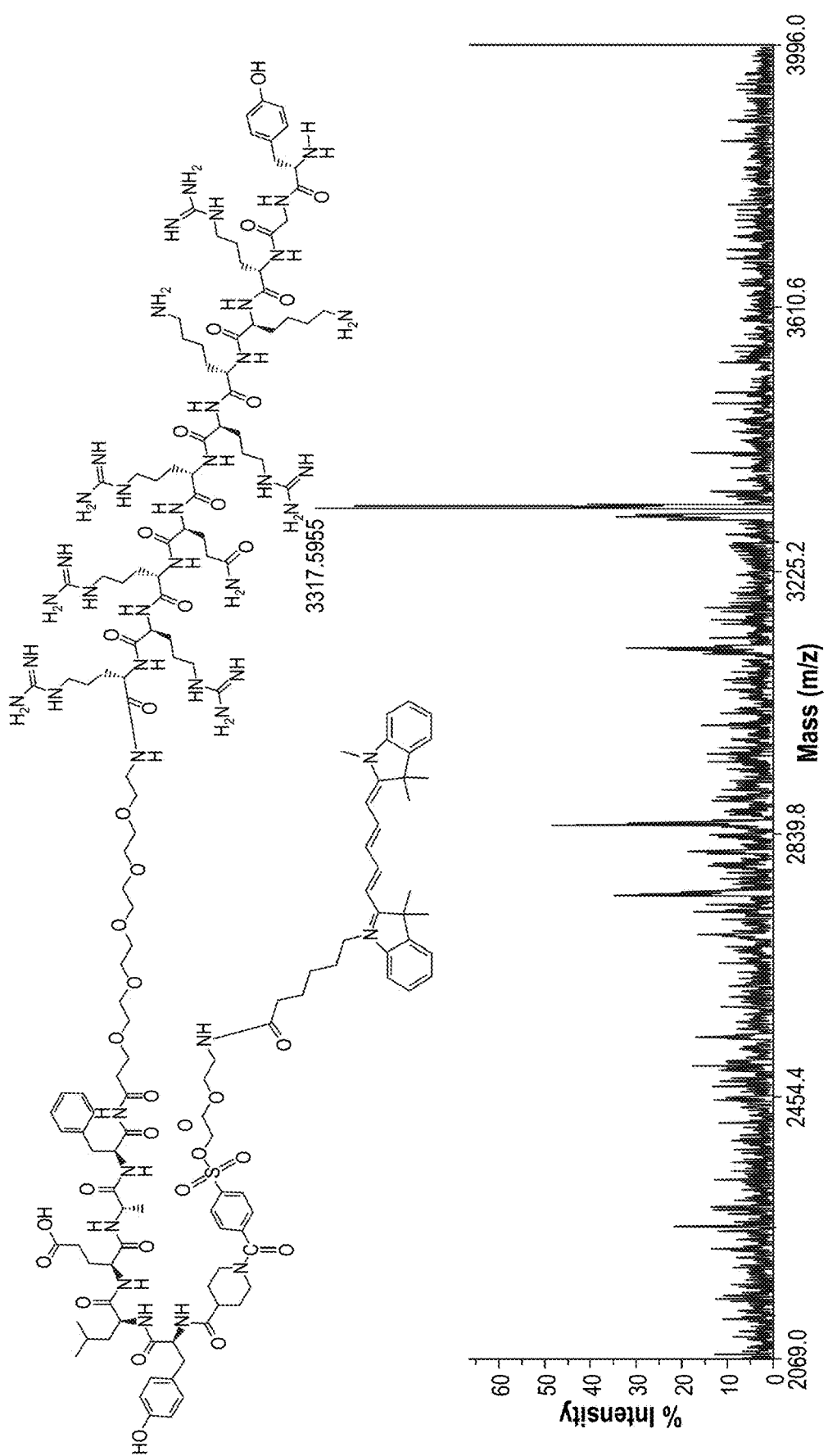
FIG. 16 is a chart showing MALDI-TOF of CPP-yleaf (SEQ ID NO: 43)-piperidine-tosyl-EG-Cy5 for labeling studies: The anchor is built onto a TAT peptide, then appended with the piperidine linker and tosyl labeling arm with a Cy5, as described above. Note, the Cy5 anchor flies very poorly on the MALDI and so background and slight impurities appear amplified. Expected: 3316, observed: 3317.50.
Figure 18:
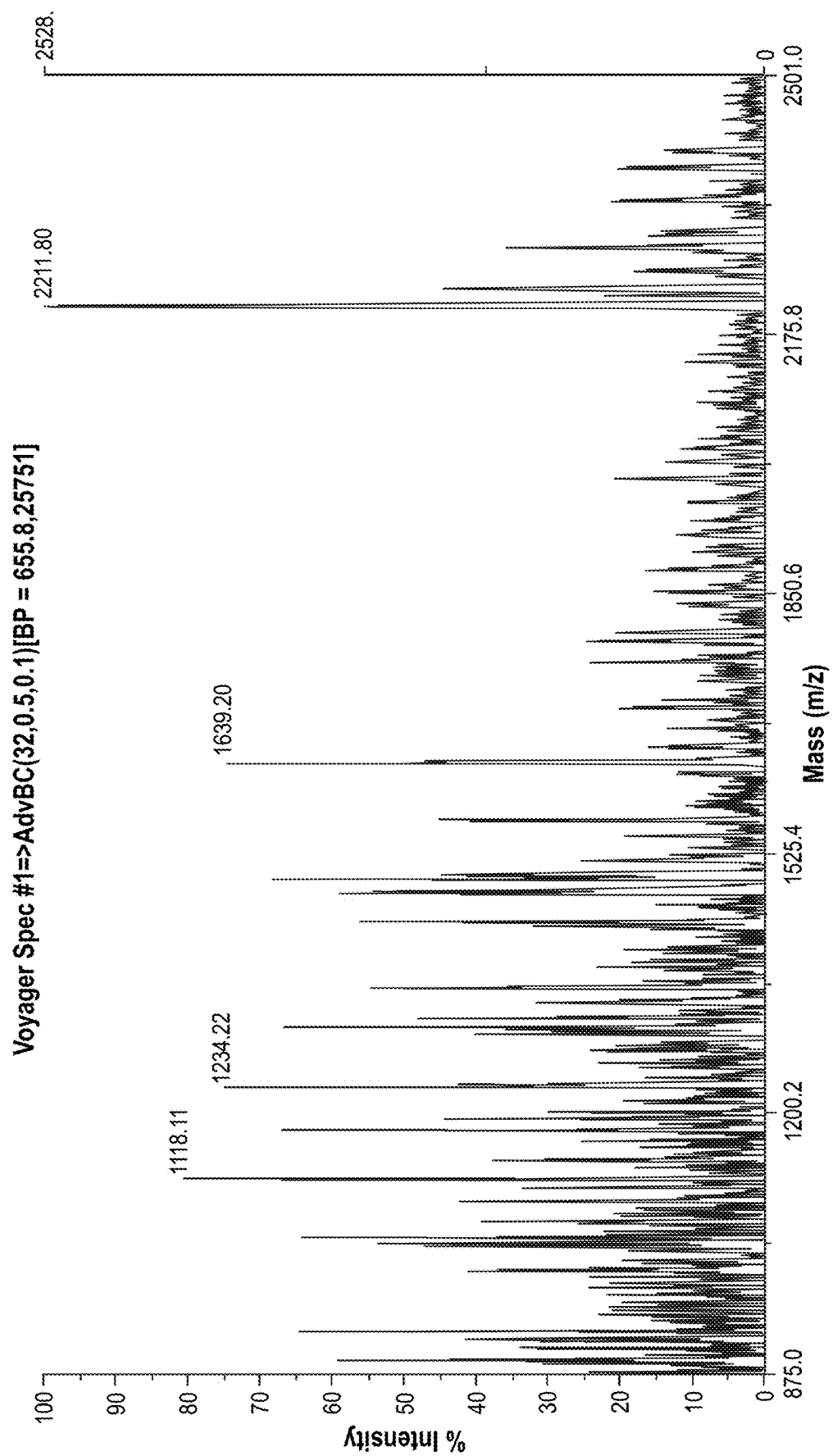
FIG. 18 is a chart showing MALDI-TOF of Cy5 dye-labeled trypsin digests from tosyl labeling experiments. The GST-E17K PHD-Akt1 protein that had been labeled by the anchor-tosyl-Cy5 was trypsin digested and the fragments were analyzed by MALDI-TOF MS.
Figure 19:
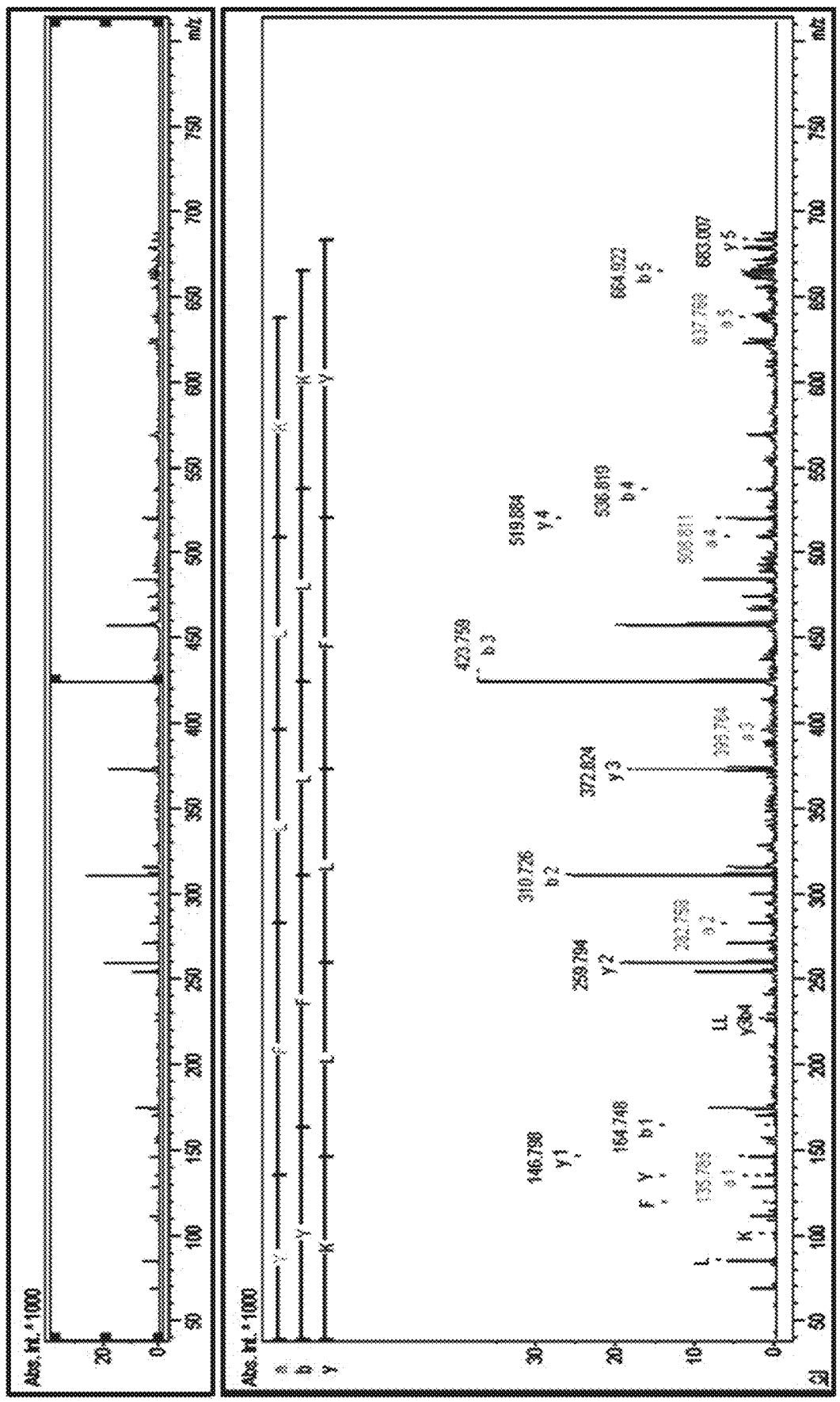
FIG. 19 is a chart showing MALDI-TOF/TOF unlabeled YFLLK (SEQ ID NO: 5) fragmentation. The unlabeled YFLLK (SEQ ID NO: 5) trypsin fragment analyzed by MALDI-TOF/TOF MS. The fragments shown demonstrate that we are able to use MALDI-TOF/TOF to readily fragment the trypsin-digested proteins in order to determine the location of the dye label.

For the assay, yleaf was modified at the N-terminus to contain a tosylate linker attached to a Cy5 dye molecule to enable easy identification of the labeled and digested protein fragments (FIG. 2a and FIG. 16). A Glutathione S-Transferase (GST)-Akt1(E17K) protein (SignalChem) was incubated with the Cy5-appended yleaf peptide. The labeling of protein target was initially confirmed by visualization on a fluorescent gel reader (FIG. 3b) as well as a Western blotting visualization of an experiment in which a biotin-label was substituted for the fluorescent tag. The labeled protein and an unlabeled control were then trypsin digested from the gel and were analyzed by matrix-assisted laser desorption/ionization time-of-flight (MALDI-TOF) MS (FIGS. 18 and 19). Five peaks appeared in the MS of the labeled protein that were not present in the unlabeled protein digests. Those peaks all corresponded to an expected trypsin fragment plus the weight of the linker and dye. These peaks were then analyzed by MALDI TOF/TOF MS to extract sequence information for the labeled regions of the protein. All but one of the dye labeled peptides were difficult to fragment, as is characteristic of cationic peptide labels[20]. The labeled digest YFLLK (SEQ ID NO: 5) could be fragmented and indicated the presence of the dye on the Y amino acid (FIG. 19). This is consistent with the original literature on the labeling technique[19] which showed that Y, E and H amino acids are the nucleophiles that can be labeled. The other labeled Akt1 fragments that were identified contain at least one of these amino acids. One fragment contains two such amino acids and, in fact, there were MALDI peaks corresponding to the masses of both the singly and doubly labeled fragment. FIG. 2d shows the location of the labeled fragments in the PH Domain sequence, as well as the amino acids that should contain the label.

The labeling sites were then mapped on a composite crystal structure of GST (PDB: 1UA5) and Akt(E17K) (Akt PDB: 3O96, E17K PDB: 2UZR) (FIG. 3c). All labeled sites surround the anticipated binding site of the yleaf ligand. A thorough search of the entire MALDI spectra was conducted to identify any other labeled fragments anywhere on the large protein, but none were found. Thus, this labeling experiment demonstrates that only sites around the expected N-terminal binding site of the yleaf ligand are labeled, confirming the very specific binding of the peptide ligand at the site directed by the epitope-targeted in situ click screening process.

Cell Imaging

Cell based assays can provide a demanding environment for demonstrating the selectivity of the yleaf PCC agent to $Akt1^{E17K}$. To demonstrate target binding in a complex cellular milieu, HEK-293T cells were transfected to express GFP-tagged E17K or GFP-tagged WT PH Domain proteins. The yleaf ligand was then labeled with both a Tat cell-penetrating peptide[22] and a Cy5 dye (FIG. 2a). The combination of the GFP label on the protein and the Cy5 label on the dye permitted the use of multi-color fluorescence microscopy for interrogating any spatial registry between the two fluorescent labels, as well as tracking the efficiency of the protein expression in the cells. Live HEK-293T cells expressing these GFP-tagged proteins were exposed to varying concentrations of the modified yleaf anchor ligand 6 for one hour. The cells were then incubated in fresh media for one hour before being thoroughly washed in PBS to remove weakly and nonspecifically bound PCC and fixed for fluorescence microscopy measurements.

Figure 4A:
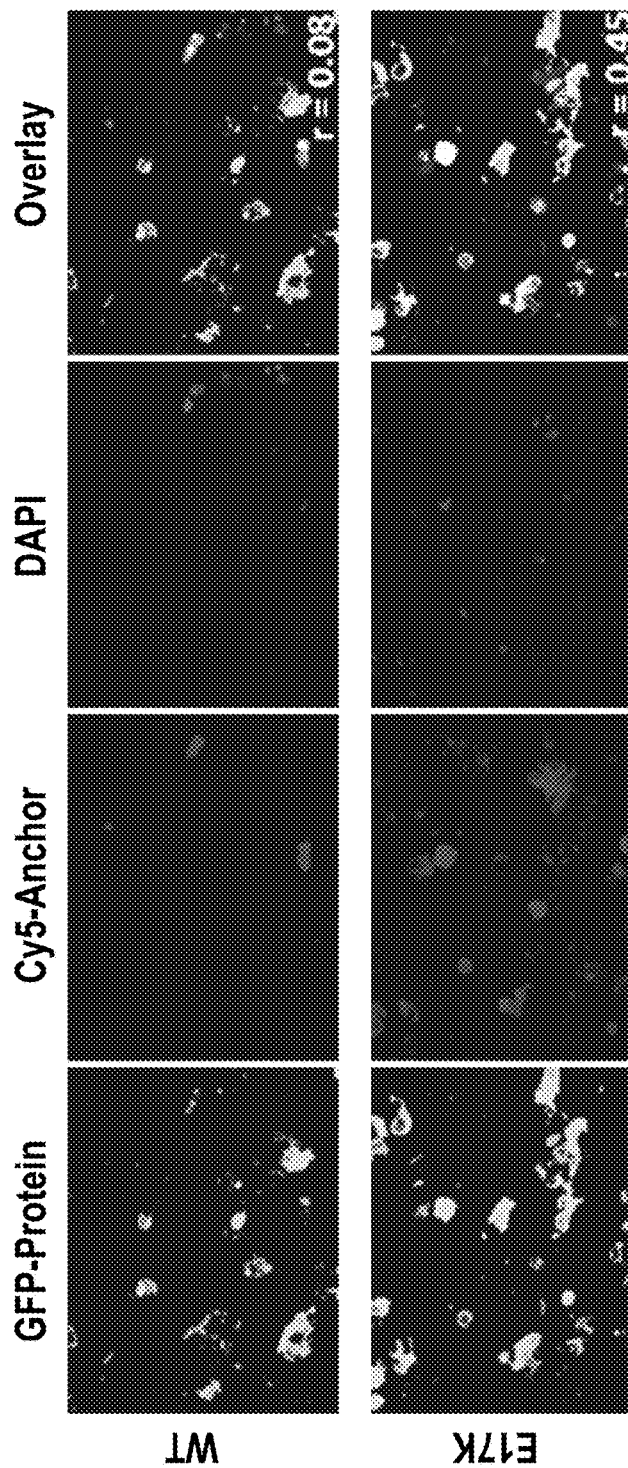
(FIG. 4A) The PH Domain was fused to green fluorescent protein (GFP) in order to visualize expression. The Cy5-yleaf (SEQ ID NO: 43)-PEG5-TAT 6 was added to live cells expressing the protein, washed extensively, and imaged. The panel shows the spatial map of GFP expression in green. The second panel shows the spatial map of the dye-labeled yleaf (SEQ ID NO: 43) ligand, and the third panel shows DAPI-stained nuclei. The r values indicate the Pearson correlation coefficient between the GFP protein and the Cy5 anchor. As demonstrated by the difference in both the Cy5 signal and the Pearson correlation coefficients, the anchor ligand is retained in E17K mutant-expressing cells to a significant degree more than in the wildtype cells, indicating ligand binding and selectivity even in a complex cellular environment.
Figure 4C:
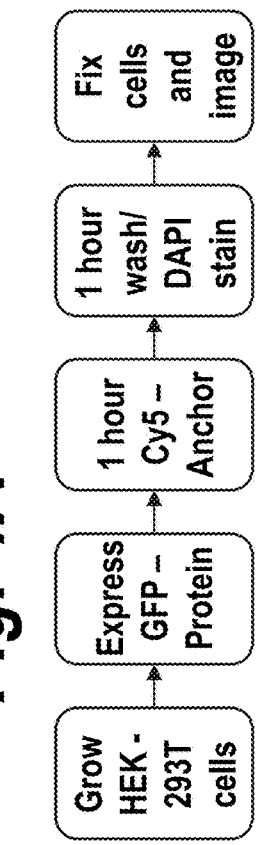
(FIG. 4C) Schematic of the experimental design for the imaging experiments. The HEK-293T cells were transfected to express GST-tagged WT or E17K mutant protein, then incubated with the CPP-anchor-Cy5 peptide 6. These cells were then incubated for one hour in media, then fixed and imaged.

Confocal microscopy images of the two differentially expressing Akt1 PHD cells showed a consistent level of expression between the GFP-WT PH Domain and GFP-E17K PHD. However, the level of the PCC agent retained by the cells was substantially different (FIG. 4). Nearly all of the cells expressing the mutant protein show some level of capture agent retention and demonstrate co-localization of capture agent and GFP-PHD protein. Pearson's correlation coefficient was used to quantify the co-localization of the two different dyes[23] by calculating over four representative images for each of the WT or E17K mutant cells and averaging the results. In a perfect correlation event the Pearson coefficient would be equal to 1, while no correlation equals 0, and a perfect negative correlation would produce a value of −1. The cells expressing GFP-PH Domain WT protein have an average correlation coefficient of r=0.14±0.06, implying little correlation, whereas the cells expressing the GFP-PH Domain E17K mutant protein have an average coefficient of r=0.47±0.13. These Pearson coefficients show a statistically significant difference between the two sets of images (p=0.0045). The Cy5 fluorescence intensity on a per cell basis has also been calculated for the cells expressing the WT and E17K proteins, and this difference is again statistically significant (p=0.00018). These assays demonstrate the selectivity of the E17K PCC agent for its target within live cells.

Example 2. Biligand and Triligand Development

Figure 5A:
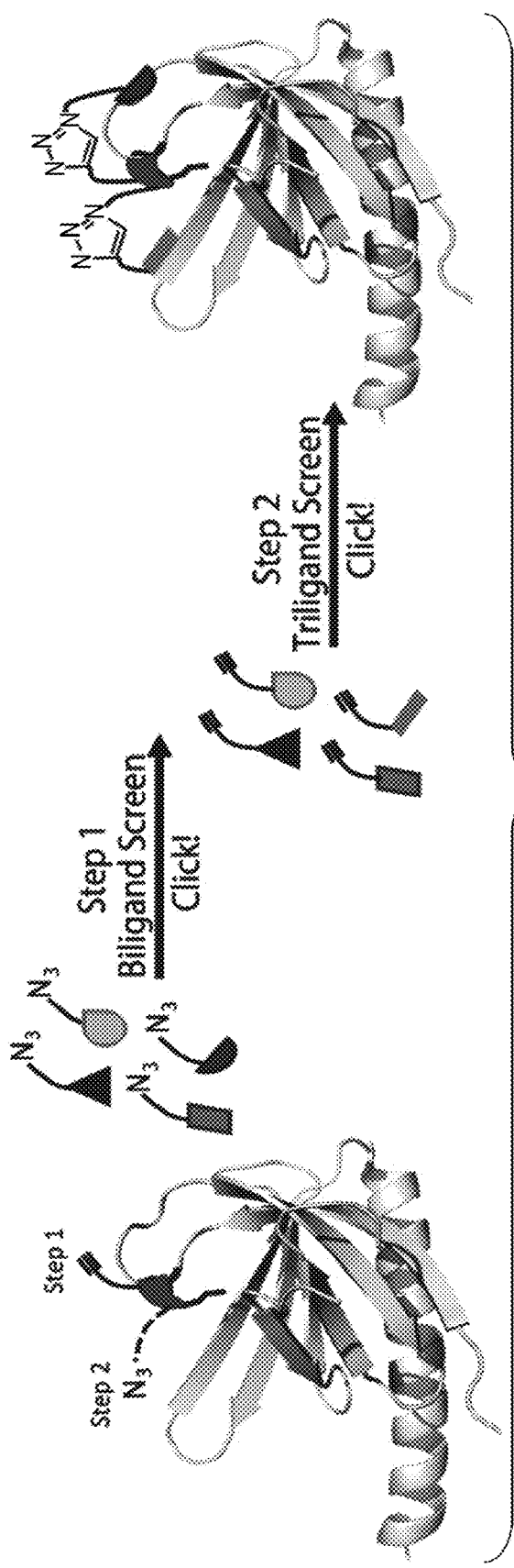
(FIG. 5A) The yleaf (SEQ ID NO: 43) anchor ligand with a C-terminal alkyne 2 was screened against an azide-terminated library in the presence of the full-length PH Domain to identify a biligand. The biligand 7 was then appended with an N-terminal azide and screened against an alkyne library to identify a triligand.
Figure 5B:
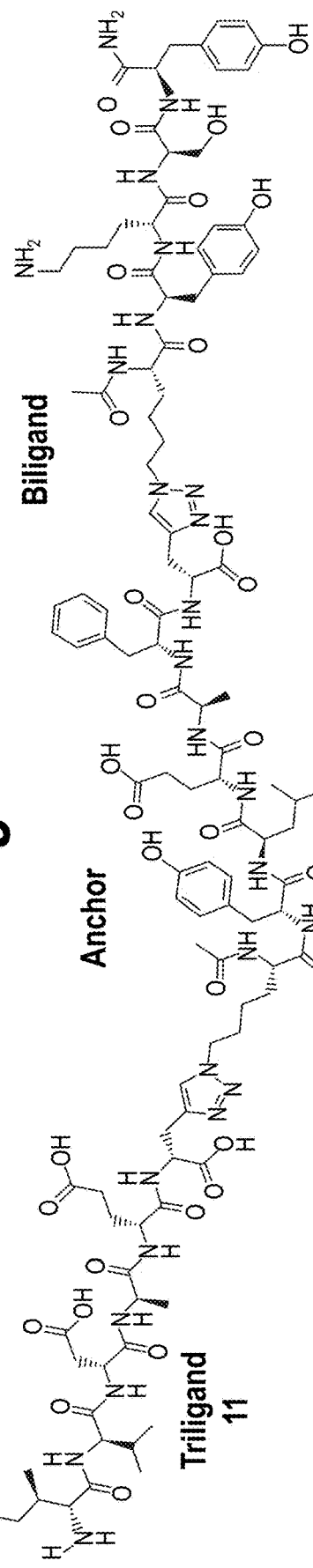
(FIG. 5B) The final triligand structure 10, which is color-coded to highlight each segment.
Figure 5C:
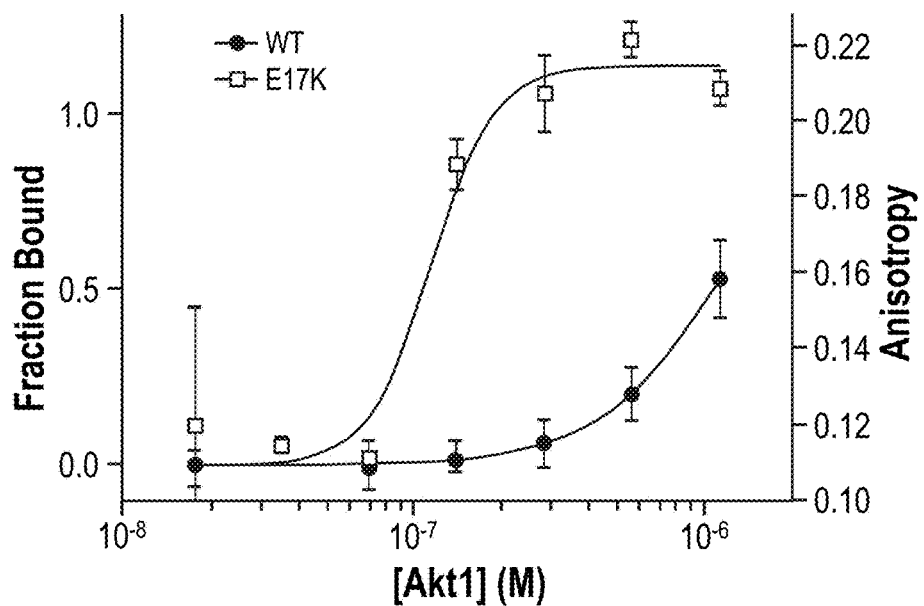
(FIG. 5C) Fluorescence polarization assays demonstrating triligand 9 affinity for the WT (blue) and E17K (red) full-length proteins, indicating that the E17K mutant selectivity is retained by the triligand. All conditions were performed in triplicate and averaged. Error bars indicate standard deviation.
Figure 5D:
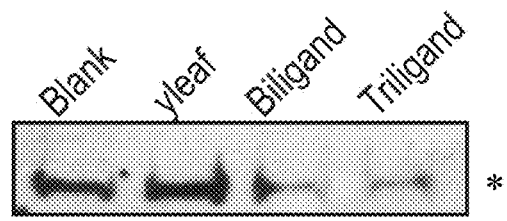
(FIG. 5D) Inhibition assays were performed with PIP3-coated resin that was incubated with constant concentrations of E17K mutant protein and each ligand. The blank measures the binding of the E17K PH Domain to PIP3 with no ligand present. The decreased binding of the protein in the presence of the biligand 7 and triligand 8 indicates inhibition.

As described above, there is increased interest in compounds that can selectively inhibit a disease-associated mutated protein target while sparing the WT variant[2]. PHD inhibiting compounds[21,22] with selectivity for the E17K variant of Akt have not been reported. The specificity of the yleaf ligand for the E17K Akt1 in live cells, coupled with the proximity of the E17K mutation to the PIP3 binding site, prompted us to consider further developing this PCC Agent into a compound capable of blocking the E17K PH Domain interaction with its PIP3 substrate. The yleaf peptide itself did not exhibit evidence of inhibition (FIG. 5D). We reasoned that a similarly targeted, but bulkier PCC Agent might serve as a steric blocker of the PHD-PIP3 interaction. To this end, we executed two cycles of iterative in situ click chemistry screens (FIG. 5a) designed to develop the yleaf ligand into a biligand, and then a triligand. To identify the biligand (the first cycle), the yleaf ligand was modified to present an alkyne at the C-terminus and a $PEG_5$-biotin group at the N-terminus. This modified ligand (called an anchor ligand) was then co-incubated with an alkyne-presenting OBOC library and the (unmodified) E17K PH Domain. Successful hits are those in which the E17K PHD promotes the click coupling of the anchor ligand onto a library peptide, and those hits are detected by screening for the formation of this clicked product. Those hits are candidate 2° ligands. For testing, the 2° ligand candidates are appended to the yleaf anchor ligand via a Cu catalyzed 1,4 triazole, to mimic the triazole formed by the protein target during the screen, to form a biligand. The biligand candidates are then subjected to affinity and specificity assays to identify a candidate biligand in a manner that is similar to what was done to identify the original yleaf ligand. Similarly, once a candidate biligand has been identified, it is then similarly modified to form a new anchor ligand, which is then similarly screened to identify a triligand. Screening details, including candidate hit sequences that were tested at both the biligand and triligand stage, are provided (FIG. 24, FIG. 28 and Tables 3 and 4). Several examples of PCC agent biligands or triligands and related screening techniques have been reported[16]. The triligand structure is shown in FIG. 5b

TABLE 3

Hit Sequences from Biligand Screen

| Az4 | h | w | p | r | SEQ ID NO: 61 |
|---|---|---|---|---|---|
| Az4 | n | v | y | l | SEQ ID NO: 59 |
| Az4 | h | y | r | w | SEQ ID NO: 55 |
| Az4 | r | d | y | r | SEQ ID NO: 75 |
| Az4 | y | n | y | k | SEQ ID NO: 74 |
| Az4 | y | k | t | w | SEQ ID NO: 88 |
| Az4 | s | r | f | y | SEQ ID NO: 73 |
| Az4 | y | k | s | y | SEQ ID NO: 76 |
| Az4 | y | y | s | r | SEQ ID NO: 71 |
| Az4 | r | h | w | s | SEQ ID NO: 66 |
| Az4 | p | w | w | r | SEQ ID NO: 89 |
| Az4 | n | f | r | y | SEQ ID NO: 90 |
| Az4 | y | w | r | l | SEQ ID NO: 57 |
| Az4 | y | w | k | G | SEQ ID NO: 56 |
| Az4 | a | y | l | y | SEQ ID NO: 63 |

TABLE 3-continued

Hit Sequences from Biligand Screen

| Az4 | h | w | r | w | SEQ ID NO: 91 |
|---|---|---|---|---|---|
| Az4 | n | w | r | l | SEQ ID NO: 53 |
| Az4 | a | a | r | w | SEQ ID NO: 60 |
| Az4 | G | r | w | y | SEQ ID NO: 72 |
| Az4 | w | f | r | i | SEQ ID NO: 58 |
| Az4 | r | p | y | y | SEQ ID NO: 65 |
| Az4 | v | w | f | r | SEQ ID NO: 70 |

TABLE 4

Hit Sequences from Triligand Screen

| G | l | — | — | m | — |
|---|---|---|---|---|---|
| i | r | y | r | n | Pra | SEQ ID NO: 92 |
| i | v | d | a | e | Pra | SEQ ID NO: 78 |

Figure 4B:
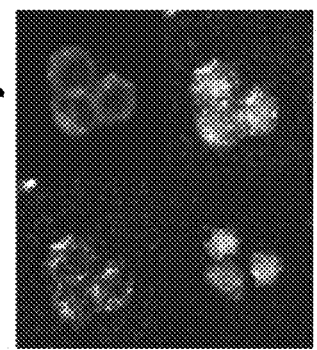
(FIG. 4B) Zoomed in image of cells expressing E17K mutant protein with anchor ligand showing significant Cy5 signal in the areas of the cells containing GFP-tagged protein.

PCC agents are shown in FIG. 4B. Likely because the expanded binding site for these larger PCC agents extends away from the location of the E17K point mutation, increasing the affinity while maintaining the selectivity of the final PCC agent upon the addition of these secondary and tertiary arms proved challenging. For example, the biligand exhibited an increase in affinity for the E17K mutant protein, but this is offset by an even larger increase in affinity for the WT protein implying a binding interaction with a conserved region of the mutant and WT proteins. However, at the triligand stage, the selectivity for E17K Akt1 relative to WT Akt1 is largely recovered, presumably due to further interaction with a mutant-specific epitope. Additionally, there is a slight preference for E17K Akt1 relative to E17K Akt2. The homology of the PH Domain between these isoforms is 79%, as calculated by a pairwise sequence analysis using Blast2Seq between the Akt1 E17K structure (2UZR) and the Akt2 PHD structure (1P6S). The binding curves of 4B yield $EC_{50}$ values for the E17K Akt1 of 61 nM, 19 nM, and 45 nM for the yleaf ligand the biligand and the triligand, respectively.

Inhibition Assays

Figure 5E:
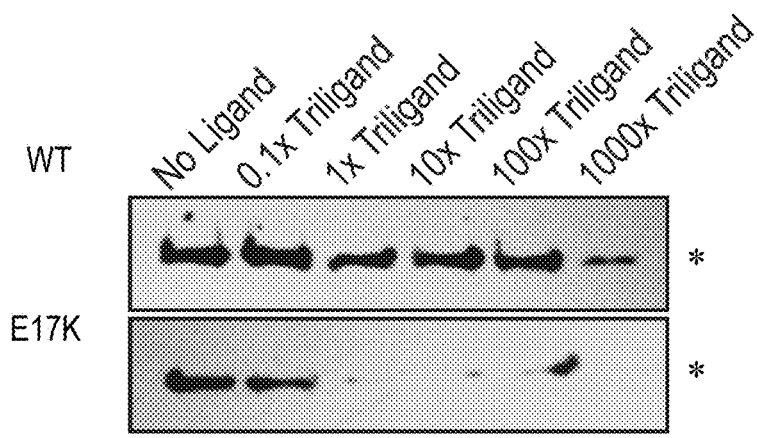
(FIG. 5E) Expanded inhibition assay with varying concentrations of triligand 8 (indicated here as the molar ratio with respect to the protein) incubated with WT or E17K proteins. The only slight drop-off in WT binding indicates little inhibition of this protein, while significant inhibition is shown against the E17K variant.

The yleaf ligand, the biligand, and the triligand were all tested for their ability to block the E17K PHD binding with PIP3. For this test, PIP3-coated resin (Echelon Biosciences) was used to mimic the PHD interaction with the cell membrane, and could be used to bind the protein as in an immunoprecipitation assay[22]. The presence of an effective blocking compound would reduce the ability of the resin to capture the protein, and would thus appear as a diminished signal in the corresponding western blot assay. A control lane containing no capture agent was used to show baseline binding of the protein to the PIP3 resin. As mentioned above, the yleaf ligand produced no change in E17K binding ability, but both the biligand and triligand exhibited the ability to block the PHD-PIP3 interaction, with the triligand being the most effective (FIG. 5d). In an expanded study, we compared the amount of E17K and WT PH domain binding relative to the amount of added triligand (FIG. 5e). This assay shows significant selective inhibition of the E17K mutant relative to the WT.

Discussion

The all-synthetic epitope targeting strategy described here provided an approach for developing a PCC agent peptide ligand that could be used to specifically detect an oncoprotein possessing a single transforming point mutation. The approach is conceptually simple and may be broadly applicable: a fragment of the target protein that contains the point mutation is chemically synthesized so that it presents a click handle near that mutation. That fragment (the epitope) is then subjected to an in situ click screen against a large library of peptides that present the complementary click chemistry handle. Viable hit candidates are those library elements that are covalently coupled to the fragment via a triazole linkage catalyzed by the strong and specific binding of the candidate ligand to the epitope. In this work, a polypeptide fragment that represented residues 1-32 of the PH Domain of Akt1E17K was prepared with an 119Pra substitution that displayed an alkyne functionality near the E17K mutation. A single generation in situ click screen yielded a 0.0015% hit rate and a peptide sequence that exhibited an approximately 10:1 selectivity for the E17K PH Domain relative to WT, with binding constant (KD) of 54±7.0 nM.

PCC agents are peptides, which allows for the straight-forward incorporation of strategic chemical modifications so as to permit several experimental illustrations of the in vitro binding specificity of the peptide ligand to the E17K PH Domain of Akt1 as well as full-length Akt1E17K. In particular, ligand-directed labeling was used to confirm that the approximate location of the ligand binding on the target protein was consistent with the epitope-targeting strategy. The yleaf (SEQ ID NO: 43) ligand, when modified with a cell-penetrating peptide and a dye label, could also be used to deliver the E17K PH domain into live cells. Upon fixing and washing the cells, those cells containing the E17K PH domain preferentially retained the ligand relative to WT, and that retained ligand exhibited statistically significant spatial correlation with the GFP-labeled E17K PH domain.

The epitope-targeting approach was demonstrated through the very demanding application of identifying a ligand specific for a single amino acid point mutation. With the synthetically-included alkyne amino acid residue to focus the library screening, there are no apparent protein structural requirements such as the need for binding pockets or other naturally addressable residues. Extending this approach towards the development of ligands specific to traditionally undruggable proteins, to post-translational modifications (e.g. phosphorylated or glycosylated epitopes), or to macrocyclic library architectures known to increase cell permeability 27 should be possible, and we are currently pursuing such routes. A working concept here is that the initial PCC agent ligand (the yleaf (SEQ ID NO: 43) peptide in this current example) provides for the ability to bring different chemical interactions to a specific region of a specific protein. In this paper, we used the yleaf (SEQ ID NO: 43) ligand to direct the covalent attachment of a payload to proximal amino acid side chains, or to bring a dye label to the protein target, or to bring a larger peptide framework that could disrupt the PH Domain-PIP3 interaction. The implication is that this epitope targeting strategy may permit the exploration of non-traditional drugging approaches that can open up interesting targets, such as AktE17K, for selective inhibition.

Standard Materials:

All amino acids were purchased from Aapptec as the FMOC carboxylic acid with the standard TFA protecting group. HATU (2-(7-Aza-1H-benzotriazole-1-yl)-1,1,3,3-tetramethyluronium hexafluorophosphate) and $PEG_5$ (Fmoc-NH-$PEG_5$-$CH_2CH_2COOH$, Fmoc-18-amino-4,7,10,13,16-pentaoxaoctadecanoic acid) were purchased from ChemPep. DIEA (diisoproylethylamine) and TFA (Trifluoroacetic acid) were purchased from Sigma. TentaGel beads were purchased as 90 μm S—$NH_2$ beads, 0.29 mmol/g, 2.86×10$^6$ beads/g from Rapp Polymere, Germany, and Rink Amide resin was purchased from Anaspec.

Bulk Peptide Synthesis:

Bulk synthesis of peptide sequences was performed using standard FMOC SPPS peptide chemistry on either the Titan 357 automated peptide synthesizer (AAPPTEC) or a Liberty 1 microwave peptide synthesizer (CEM Corporation). The typical scale was 300 mg on Rink Amide Resin, unless otherwise noted. Peptides were cleaved from the beads with side-chains deprotected using a 95:5:5 ratio of TFA:$H_2O$:TES. The peptides were purified on a prep-scale Dionex U3000 HPLC with a reverse-phase C18 column (Phenomenex). All peptides are checked for correct mass and impurities using MALDI-TOF MS and are lyophilized to a powder for long-term storage at room temperature. Concentrated peptide stocks for assays are made by dissolving powder in small amounts of DMSO and measuring the A280 absorbance via nanodrop to determine the stock concentration.

Akt1 Wildtype and E17K Mutant Pleckstrin Homology Domain Expression:

Akt1 Pleckstrin Homology Domain DNA was purchased from DNA2.0. The first 124 N-terminal amino acids from full length Akt1 were used as the PH Domain DNA (FIG. 1A), and a 6-his tag (SEQ ID NO: 4) separated by a thrombin cleavage site were added at the C-terminus of the protein for purification. In order to make the E17K mutant of the PH Domain, the glutamic acid in position 17 was mutated to a lysine via QuikChange. The DNA was synthesized in a pJexpress 414 vector containing an amp resistant gene to be expressed in E coli cells. Protein expression was performed by the Protein Expression Center at Caltech using their standard bacterial expression protocol and purified via Ni-NTA column. The proteins expressed in this manner were used for the pulldown assays confirming the anchor binding via immunoprecipitation assays and for the biligand screens. These PHD proteins were unsuitable for long-term storage under a large variety of tested conditions, so a GST tag was added to hopefully improve the long term stability.

For that reason, the DNA from DNA 2.0 was PCR'd out of the pJExpress vector to insert the restriction enzyme sites EcoRI and NotI for insertion into a pGEX-4T-1 vector containing a GST tag. The primers used were 5'-AGAGAATCCATGTCCGACGTCGC-GATCGTAAAGGAAGGG-3' (SEQ ID NO: 10) and 5'-TCTGCGGCCGCTTAGTGGTGATGATG-3' (SEQ ID NO: 11). Both the wildtype and E17K mutant DNA were cloned out of the pJExpress vector, restriction enzyme digested, and ligated into the pGEX-4T-1 vector. The confirmed correct sequences were transformed into BL21-DE3-pLys cells. An overnight starter colony from each of these plates was grown in 5 mL LB+Amp overnight. 4 mL of this starter culture was used to inoculate 500 mL of LB+Amp and grown to mid-log phase. The cultures were inoculated with 1 mM IPTG and grown 5 hours at 28° C. The cells were spun down for 10 minutes at 8,000 RPM and lysed with lysis buffer (1×TBS, 1 mM DTT, 1 mg/mL Lysozyme, 1% Triton-X), and left for 30 minutes on ice before flash freezing in liquid nitrogen. Upon thawing on ice, the lysate was sonicated for 5 minutes, then spun down for 30 minutes at 10,000 RPM. The supernatant was then purified on a HisPur Co column (Pierce) using the recommended protocol. These GST-tagged proteins were used to confirm the biligand binding via immunoprecipitation assays and for the triligand screens. They were also used to obtain the full ELISA curves of all three ligands. These proteins, however, were also not suitable for long term storage and needed to be re-expressed for all assays.

The imaging experiments required that the PHD protein be expressed in mammalian cells and have a GFP tag for visualization. Because of this, Akt1 DNA with codons optimized for use in mammalian cells was obtained from InvivoGen as a pUNO-hAKT1 plasmid. The DNA was mutated so both a wildtype and E17K version were on hand. The primers used to clone the DNA from this vector into a TOPO C-terminal GFP mammalian vector were: 5'-AA-GATGGGGATGAGCGACGTGGCT-3' (SEQ ID NO: 12) AND 5'-TCCCCGACCGGAAGTCCATCTCCTC-3' (SEQ ID NO: 13), and cloning was done as per the TOPO vector manual. Because the GST-PHD proteins expressed in E coli were still not stable for long term storage, this DNA was used to express the PHD in mammalian cells. The expressions were done by transfecting HEK-293-6E cells with XtremeGene HD by the Protein Expression Center at Caltech following their standard protocols. These proteins were not purified, and were used as-is out of cell lysates. This protein was used in triligand pulldown and inhibition assays, and was still not stable for long term storage.

CD Spectroscopy of 33-Mer Peptide Epitope

Lyophilized powder of the 33-mer biotin-tagged target fragment that was used for screening was dissolved in 500 μL of 1×PBS to a concentration of 0.5 mg/mL. Concentrations were estimated by weight and confirmed by A280 measurement. Experiments were performed on a Aviv 62 CD Spectrometer. The machine was purged for 20 minutes with $N_2$, then the 1×PBS blank in a 500 μL 1 cm cuvette was added and the machine was purged with $N_2$ for another 5 minutes. The spectra was acquired by 3 measurements/minute from wavelengths 199-250 nM. The 33mer fragment sample was then added, purged for 5 minutes, and was measured exactly as the blank. The 33mer cuvette was then removed, and 500 μL of 7.0M pH=2.0 Guanadine-HCl was added to denature the sample. This spectra was acquired as above.

Figure 8:
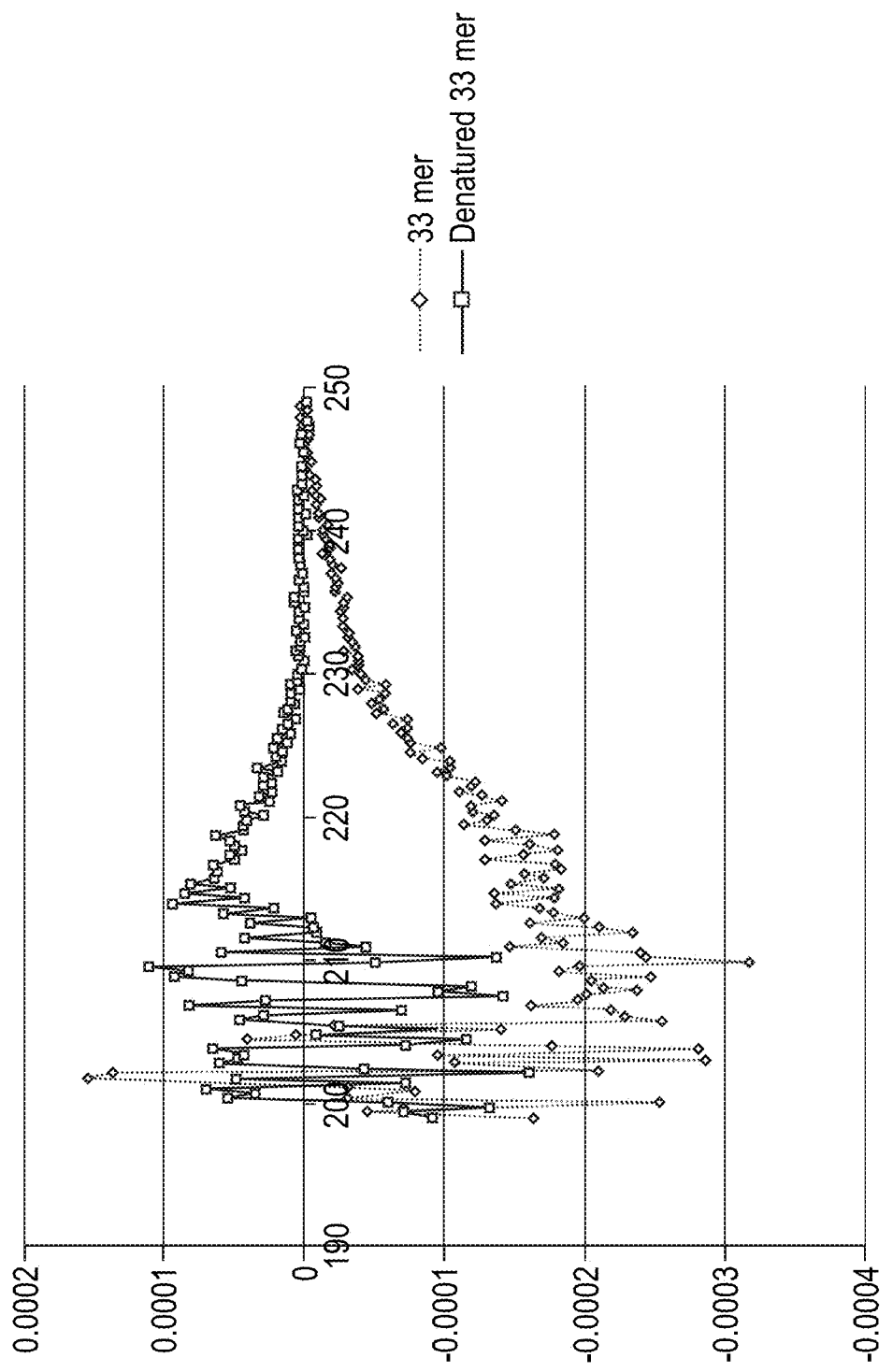
FIG. 8 is a CD Spectra of 33mer fragment, folded and denatured. The bottom spectra indicated the 33mer target fragment that was used in screening. The dip at 217 nm indicates β-sheet formation, as to be expected from the protein structure. The messy spectra from 200-210 nm are probably due to the biotin tags attached to the fragment.

To work up the data, the signal in AA from the sample was subtracted from the blank at each wavelength. Then the mean residue molar circular dichroism AEMR was calculated from this readout using the number of residues in the fragment (33) and the concentration in mg/mL (0.5 for the folded sample, 0.25 for the denatured sample since it was diluted with Guanadine-HCl) using the equation: $\Delta\varepsilon_{MR}=\Delta A/((\text{residue \#}\times\text{concentration mg/mL})\times I)$. The spectra were graphed by plotting this number against the wavelength. As can be seen in FIG. 8, the CD signature for the 33mer peptide resembles that of a β-sheet, which was the expected structure based on the full protein crystal structure. This binding disappeared upon the addition of the denaturing buffer, demonstrating that this is a real structure in the 33mer fragment.

Screen for Initial Anchor Peptide (FIG. 9):

Screens were performed using a library with 100% Met coupled at the C-terminus for potential MALDI TOF/TOF sequencing[2]. The library was a comprehensive 5-mer containing 18 unnatural D-amino acids, excluding Met and Cys due to stability reasons. The N-terminus contained an azide click handle with varying carbon chain lengths—2 carbon, 4 carbon and 8 carbon—for in vivo click with the Pra on the target 33-mer. Screens were done with 300 mg of dried library beads swelled at least six hours in 1×TBS (25 mM Tris-Cl, 150 mM NaCl, 10 mM $MgCl_2$, pH=7.5) buffer.

Preclear (FIG. 9A):

Swelled library beads were blocked overnight in 5% w/v dried non-fat milk in 1×TBS, then washed with 1×TBS three times. Five milliliters of a 1:10,000 dilution of Streptavidin-Alkaline Phosphatase Conjugate in 0.5% milk in TBS was added to the beads and incubated shaking at room temperature for one hour. The beads were washed with a high-salt TBS buffer (1×TBS with 750 mM NaCl) three times, then let shake in high salt buffer for one hour. The beads were then washed three times with BCIP buffer (100 mM Tris-Cl, 150 mM NaCl, 1 mM $MgCl_2$, pH=9.0) and developed by adding 15 mL BCIP buffer plus 13 μL BCIP and 26 μL NBT (two part system, Promega) After one hour, the purple beads were removed by pipette and discarded. The remaining beads were incubated in NMP 4 hours to remove trace purple precipitate from the BCIP/NBT reaction, then were washed 5× with methanol, 5× with water, 5× with TBS and reblocked overnight in 5% milk.

Product Screen (FIG. 9B):

Beads remaining from the preclear were washed three times with 1×TBS, then incubated with 5 mL of a 100 nM dilution of the 33-mer target in 0.5% milk for either 5 hours or 12 hours to allow for an in situ click reaction to occur. The beads were then washed three times with 1×TBS and incubated for one hour with a 7M Guanadine-HCl buffer, pH=2.0 to remove all 33-mer target not attached covalently to the beads. These beads were then washed ten times with 1×TBS, reblocked for two hours in 5% milk, then incubated for one hour with a 1:10,000 dilution of Streptavidin-Alkaline Phosphatase conjugate in 0.5% milk in TBS to detect for the presence of the 33-mer target clicked to a bead. The beads were washed three times with a high-salt TBS buffer, then let shake in high salt buffer for one hour. Afterwards, the beads were again washed three times in BCIP buffer and developed as per the preclear. Purple beads are removed from the screen via pipette as hit beads. These hits were incubated in the guanidine-HCl buffer to remove attached streptavidin, washed ten times with water and sequenced via edman degradation on a Procise CLC system from Applied Biosystems. See Table 1 for sequences from 5 hour screen, Table 2 for sequences from 16 hour screen.

Sequence Analysis:

Hit sequences were analyzed via a peptide analysis algorithm that organized hits based on their hydrophobicity and sequence homology using principal component analysis. The algorithm analyzes a series of peptides and graphs them on a 2D sequence map. Clusters of hits were circled (FIG. 3), and one peptide from each cluster was scaled-up and tested for binding to both wildtype and mutant PH domain. The ligands chosen for scale up were: dqntr (SEQ ID NO: 36), ypwve (SEQ ID NO: 20), eefef (SEQ ID NO: 77), yleaf (SEQ ID NO: 43), and elnhy (SEQ ID NO: 41). Any ligand candidates that were difficult to call on the sequencing were not chosen for scale-up and testing.

Details on Tryptic Fragment Workup for Labeling Experiment:

All of the peaks from the MALDI-TOF spectra of the labeled tryptic digests were analyzed for their potential to contain a dye label. The MALDI spectra was manually calibrated to ensure the least possible error. Each peak was then analyzed by zooming in on the spectra on the computer and obtaining the exact mass for the monoisotopic peak, which is recorded as "MALDI peak" in Table 5 below.

TABLE 5

Tryptic fragment data workup for labeling experiment.

| MALDI Peak | Peak - dye | | Expected | Digest | Peak Area | P/M 1 | Corresponding Fragment |
|---|---|---|---|---|---|---|---|
| 1053.15 | 500.78 | | 1051.6349 | 499.265 | 4296.69 | 1.5151 | |
| 1090.15 | 537.78 | | 1114.6007 | 562.2307 | 5813.86 | 24.4507 | |
| 1118.11 | 565.74 | | 1114.6007 | 562.2307 | 12649.91 | 3.5093 | |
| 1142.16 | 589.79 | | 1132.6993 | 580.329 | 4217.63 | 9.4607 | |
| 1179.14 | 626.77 | | 1173.6565 | 621.287 | 4393.2 | 5.4835 | |
| 1194.14 | 641.77 | | 1201.732 | 649.362 | 5139.51 | 7.592 | |
| 1202.16 | 649.79 | | 1201.732 | 649.362 | 4103.69 | 0.428 | |
| 1234.66 | 682.29 | * | 1234.7826 | 682.4126 | 8193.47 | 0.1226 | YFLLK (SEQ ID NO: 5) |
| 1300.08 | 747.71 | | 1303.7273 | 751.3573 | 6445.8 | 3.6473 | |
| 1302.09 | 749.72 | | 1303.7273 | 751.357 | 4496.81 | 1.6373 | |
| 1308.09 | 755.72 | | 1303.7525 | 751.3825 | 5926.62 | 4.3375 | |
| 1320.57 | 768.2 | * | 1320.7691 | 768.3991 | 7886.31 | 0.1991 | EGWLHK (SEQ ID NO: 14) |
| 1440.11 | 887.74 | | 1447.8246 | 895.4546 | 6406.74 | 7.7146 | |
| 1475.16 | 922.79 | | 1477.9158 | 925.5458 | 10131.17 | 2.7558 | |
| 1493.13 | 940.76 | | 1477.9158 | 925.5458 | 9276.21 | 15.2142 | |
| 1499.13 | 946.76 | | 1507.814 | 955.444 | 4112.05 | 8.684 | |
| 1515.1 | 962.73 | | 1507.814 | 955.444 | 4687.71 | 7.286 | |
| 1567.65 | 1015.28 | | 1565.8591 | 1013.489 | 7907.73 | 1.7909 | |
| 1639.2 | 1086.83 | | 1645.9403 | 1093.57 | 21961.13 | 6.7403 | |
| 1707.53 | 1155.16 | | 1701.0101 | 1148.64 | 12923.9 | 6.5199 | |
| 1791.09 | 1238.72 | | 1795.9606 | 1243.591 | 5200.25 | 4.8706 | |
| 1802.79 | 1250.42 | | 1800.0105 | 1247.641 | 8149.76 | 2.7795 | |
| 1851.79 | 1299.42 | | 1841.9813 | 1289.61 | 4331.77 | 9.8087 | |
| 1995.47 | 1443.1 | | 1957.1459 | 1404.78 | 4368.22 | 38.3241 | EEWTTAIQTVADGLK (SEQ ID NO: 15) |
| 2212.04 | 1659.67 | * | 2213.208 | 1660.838 | 95735.94 | 1.168 | |
| 2225.51 | 1673.14 | | 2213.208 | 1660.838 | 17712.89 | 12.302 | |
| 2233.95 | 1681.58 | | 2213.208 | 1660.838 | 12256.12 | 20.742 | |
| 2284.12 | 1731.75 | | 2344.242 | 1791.872 | 5711.7 | 60.122 | |
| 2306.92 | 1754.55 | | 2344.242 | 1791.872 | 6553.24 | 37.322 | |
| 2344.23 | 1791.86 | * | 2344.242 | 1791.872 | 4506.1 | 0.012 | EAPLNNFSVAQCQLMK (SEQ ID NO: 16) |
| 2383.46 | 1831.09 | | 2362.2571 | 1809.887 | 8608.79 | 21.2029 | |
| 2406.7 | 1854.33 | | 2362.2571 | 1809.89 | 4338.6 | 44.4429 | |

The mass of the dye, 552.37 g/mol, was subtracted from this peak, and it was compared to the closest possible theoretical tryptic digest fragment ("Digest"). The "expected" mass of the digest plus the dye was calculated and subtracted from the observed mass, "MALDI peak", and the absolute value of this difference was recorded in "P/M 1". The peak area was obtained from the MALDI data and added to the spreadsheet as "Peak Area" to allow for a cutoff (4500) of any peaks that looked to be within the noise. Any peak below this value is shown in red italics, and was not considered for this study. Any peak that was within 0.1% of the mass of the expected digest mass was considered to be within error of the instrument and was considered a hit dye-labeled fragment. There were no new peaks seen using this method than were discovered by looking for peaks that grew in from the unlabeled MALDI to the labeled MALDI. The labeled sites seen in this MALDI-TOF experiment were all seen previously in at least 2 LC/ESI-MS experiments attempting to identify the labeled region.

The peak at ~2212 was not seen on the unlabeled mass spec, but is seen on the labeled fragment and was considered a hit. 2211 is also, however, a common mass seen for trypsin. We do see this particular unlabeled fragment fly in the MALDI-TOF MS (1659), and know from the ESI-MS experiments that this is a site that can be labeled. In attempting to zoom in for the monoisotopic mass, we see a broad peak with no clearly identifiable mass peak—unlike all of the other peaks in the spectrum which showed the distribution of masses very clearly. This lead us to believe that we are, in fact, seeing this peak labeled in the MALDI, especially as this site was seen as labeled by the ESI. The ESI labeling experiments were also done using a labeling arm containing biotin and not Cy5, so this mass did not overlap with trypsin in these experiments. We just cannot exactly call this mass in the MALDI due to the similarity of this peak to that of trypsin.

Figure 12:
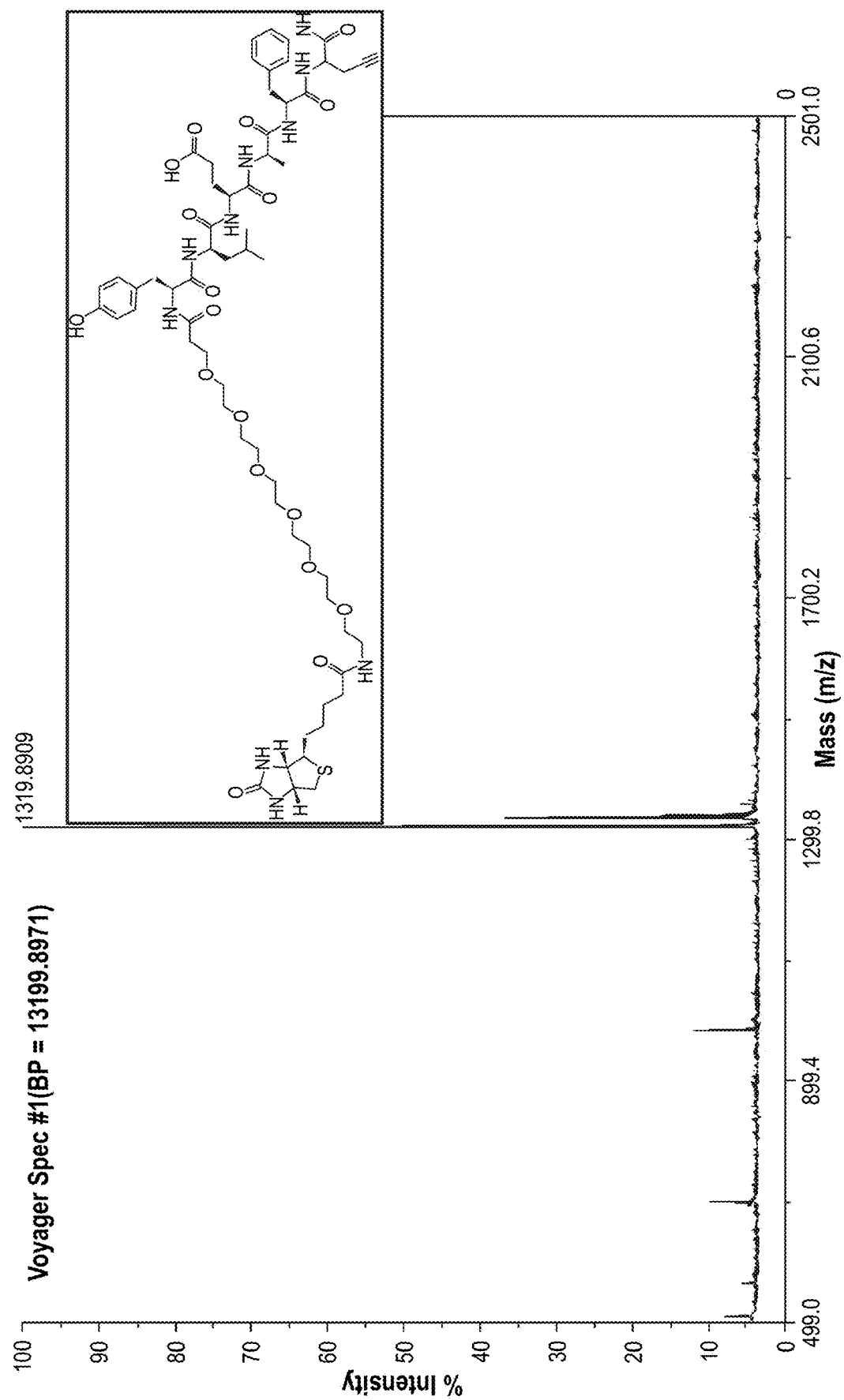
FIG. 12 is a chart showing the structure and maldi-tof of biotin-peg$_5$-yleaf (SEQ ID NO: 43)-pra anchor ligand. The anchor ligand is appended with a PEG5-biotin then a propargylglycine alkyne amino acid for the click reaction during the screen. Expected M+Na: 1319.62, observed: 1319.89.

Screen for Biligand Peptide (FIG. 24):

The anchor determined above—yleaf (SEQ ID NO: 43)—was scaled up with a biotin on the N-terminus for detection, a PEG$_5$ linker between the biotin and the peptide, and a d-propargylglycine (Pra) on the C-terminus as the in situ click handle (Biotin-PEG$_5$-yleaf (SEQ ID NO: 43)-Pra, FIG. 12). Screens were done using a library with 100% Met coupled at the C-terminus for potential MALDI TOF/TOF sequencing. The library consisted of a comprehensive 5-mer containing 18 unnatural D-amino acids, excluding Met and Cys due to stability reasons. The N-terminus contained an azide click handle with a 4 carbon chain (Lys(N$_3$))— for in vivo click with the Pra on the anchor peptide. Screens used 300 mg of dried library beads swelled at least six hours in 1×TBS (25 mM Tris-Cl, 150 mM NaCl, 10 mM MgCl$_2$, pH=7.5) buffer.

Preclear (FIG. 24A):

Swelled library beads were blocked overnight in 5% w/v dried non-fat milk in 1×TBS, then washed with 1×TBS three times. The beads were incubated with a 7.15 µM solution of the anchor peptide-Biot-PEG$_5$-yleaf (SEQ ID NO: 43)-Pra for one hour then washed 3× with 1×TBS. Five milliliters of a 1:10,000 dilution of Streptavidin-Alkaline Phosphatase Conjugate in 0.5% milk in TBS was added to the beads and incubated with shaking at room temperature for one hour. The beads were washed with a high-salt TBS buffer (1×TBS with 750 mM NaCl) three times, then let shake in high salt buffer for one hour. The beads were then washed three times with BCIP buffer (100 mM Tris-Cl, 150 mM NaCl, 1 mM MgCl$_2$, pH=9.0) and developed by adding 15 mL BCIP buffer plus 13 µL BCIP and 26 µL NBT. After one hour, the purple beads were removed by pipette and discarded. The remaining beads were incubated in NMP 4 hours to remove trace purple precipitate from the BCIP/NBT reaction, then were washed 5× with methanol, 5× with water, 5× with TBS and reblocked overnight in 5% milk.

Target Screen (FIG. 24B):

The clear beads remaining from the preclear were reblocked in 5% milk in 1×TBS for two hours. They were then washed three times with 1×TBS. A pre-incubated solution of E17K mutant protein (715 nM) and anchor ligand (7.15 µM) in 3 mL of 0.5% milk was added to the blocked library beads and incubated for either 5 hours or overnight to allow an in situ click reaction to occur. In the morning, the beads were washed three times with 1×TBS, then incubated with a 1:4,000 dilution of an anti-His Alkaline Phosphatase conjugated antibody (Abcam) in 0.5% milk for one hour. The beads were then washed three times with a high salt TBS, then incubated on the shaking arm for one hour with the high salt buffer. They were then washed three times with BCIP buffer and developed as previously. Hit beads turned purple and were removed and washed in NMP for four hours to decolorize, then guanidine-HCl to denature and remove and remaining protein. The beads were then washed ten times with water and reblocked in 5% milk overnight.

Off-Target Anti-Screen (FIG. 24C):

The beads from the target screen were washed three times with 1×TBS, then incubated with the off-target, wildtype PHD protein in 0.5% milk for one hour on the shaking arm at room temperature. The beads were washed three times with 1×TBS, then incubated with a 1:4,000 dilution of Anti-His Alkaline Phosphatase conjugated antibody in 0.5% milk for one hour at room temperature. They were then washed three times with high salt buffer and let shake for one hour in high salt at room temperature before being washed three times with BCIP buffer and developed as previously. The beads that turned purple bind to both mutant and wildtype protein or to the anti-his antibody and were set aside. The beads that remained clear were picked and washed with guanidine-HCl to remove any bound proteins and reblocked in 5% milk overnight.

Product Screen (FIG. 24D):

The beads specific for the mutant PH domain were washed three times with 1×TBS. They were then incubated with a 1:10,000 dilution of Streptavidin-Alkaline Phosphatase conjugate in 0.5% milk for one hour. The beads were washed three times with high salt TBS then let shake for one hour with high salt buffer before being washed three times with BCIP buffer and developed as previously. The beads that turned purple contained the anchor peptide covalently bound to the bead and had formed a protein-catalyzed in situ click reaction. These beads were collected and stripped with guanidine-HCl for one hour, washed ten times with water, and sequenced via edman degradation as per the anchor candidate hits. There were 22 total hit beads (Table 3). Upon sequencing, the selected hits ended up containing only four amino acids instead of five. One of the random amino acids must have not coupled upon library synthesis, but the sequences were used anyways.

Figure 25:
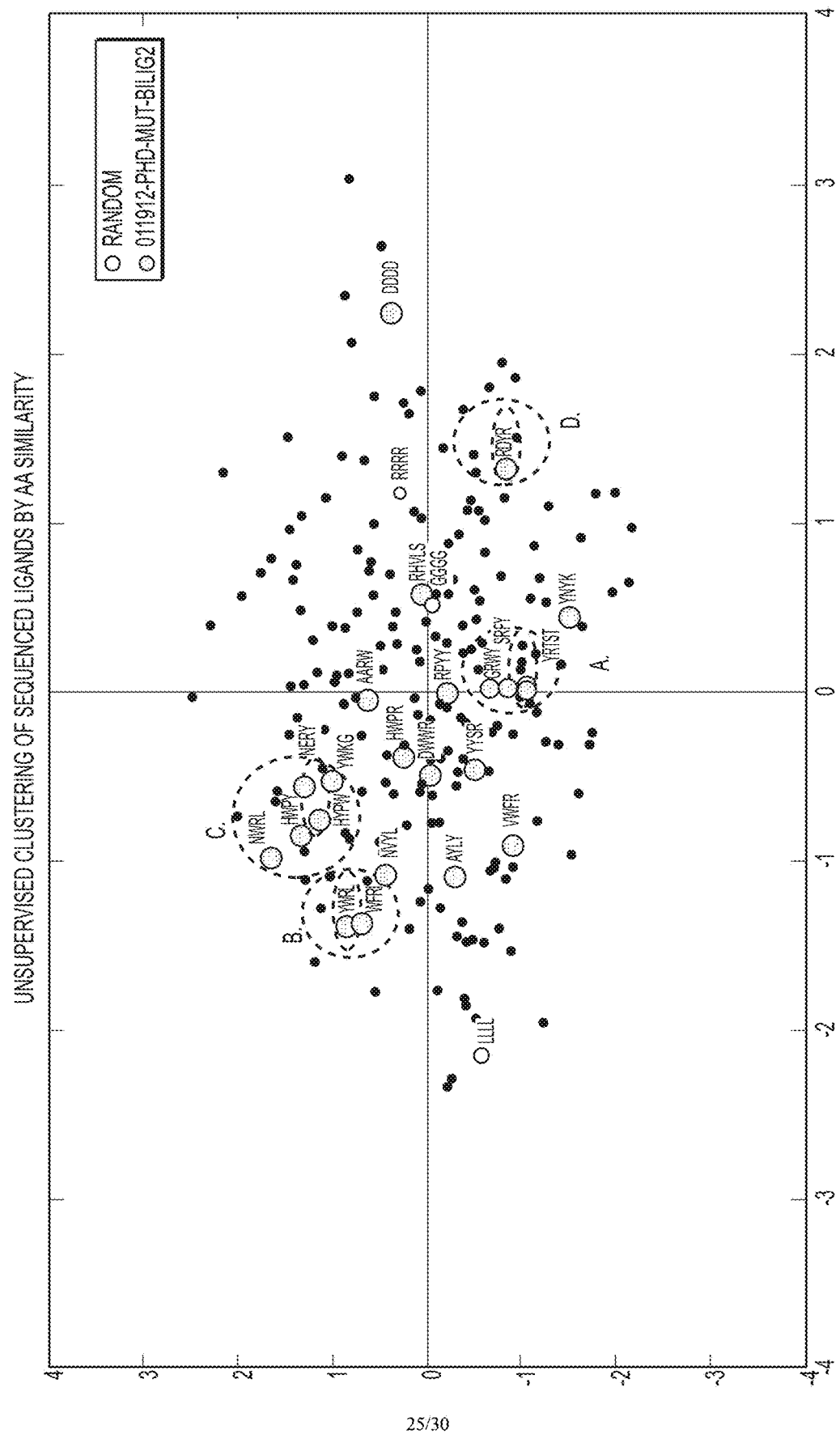
FIG. 25 is a chart showing unsupervised clustering of biligand sequence ligands by AA similarity. Hit sequences from the biligand screen were analyzed by their hydrophobicity and sequence homology using principal component analysis. Clusters circled in green indicate clustered regions and the cyan circles indicate the peptide that was selected and scaled-up as a possible biligand sequence. The potential biligand sequences that were tested are: yleaf (SEQ ID NO: 43)-ywrl (SEQ ID NO: 57), yleaf (SEQ ID NO: 43)-yksy (SEQ ID NO: 76), yleaf (SEQ ID NO: 43)-rdyr (SEQ ID NO: 75), and yleaf (SEQ ID NO: 43)-hyrw (SEQ ID NO: 55), where "yleaf" (SEQ ID NO: 43) is the anchor ligand and the "-" indicates the location of the triazole linkage.
Figure 26:
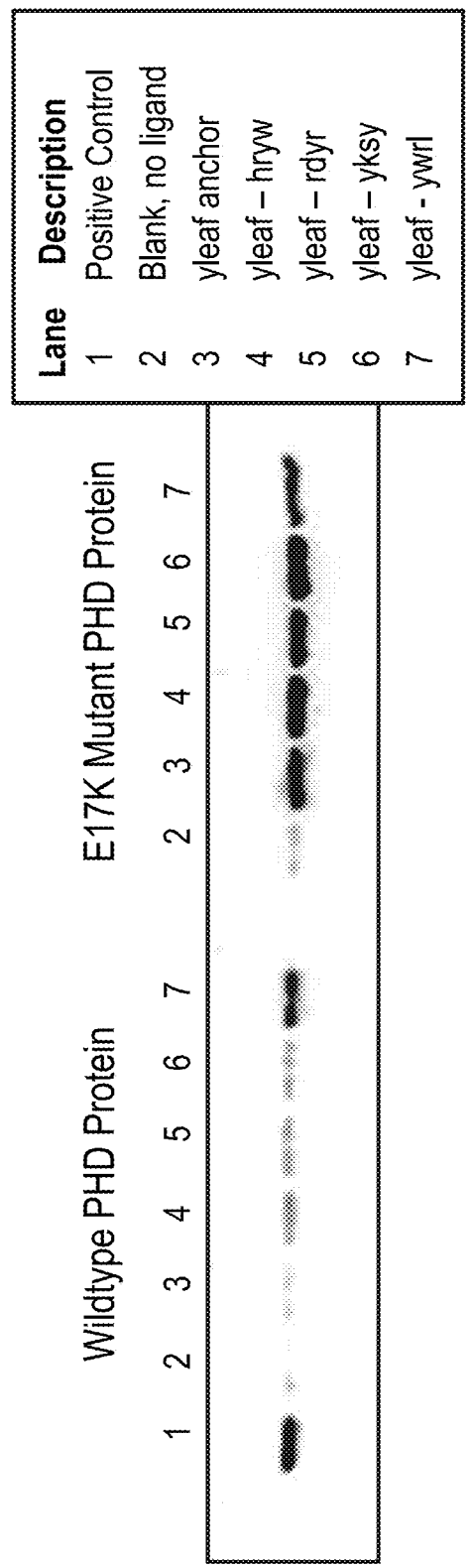
FIG. 26 shows a pulldown assay results for biligand candidates. Lane 1: positive protein blot control; lane 2: WT GST-PHD, no ligand; lane 3: WT GST-PHD, yleaf (SEQ ID NO: 43) anchor; lane 4: WT GST-PHD yleaf (SEQ ID NO: 43)-hryw (SEQ ID NO: 55) biligand; lane 5: WT GST-PHD, yleaf (SEQ ID NO: 43)-rdyr (SEQ ID NO: 75) biligand; lane 6: WT GST-PHD, yleaf (SEQ ID NO: 43)-yksy (SEQ ID NO: 76) biligand; lane 7: WT GST-PHD, yleaf (SEQ ID NO: 43)-ywrl (SEQ ID NO: 43) biligand. Lanes 8-13 are the same as 2-7, but with the E17K GST-PHD protein. Note that all of the biligand candidates improve upon the binding of the anchor ligand, but yleaf (SEQ ID NO: 43)-yksy (SEQ ID NO: 76) shows the greatest signal in binding the E17K protein and the lowest in binding the WT protein. This biligand was chosen as the candidate biligand and carried on to triligand screening.

Streptavidin-Agarose Immunoprecipitation (Pulldown) Assays to Test Biligand Candidates Four biligand candidates were chosen based on their hydrophobicity and sequence homology using principal component analysis (FIG. 25). Biligands were synthesized by coupling the 2° ligand onto Rink Amide Resin on the Titan peptide synthesizer. The amide group on the end of the Lys(N$_3$) was capped by shaking the resin with 2 mL acetic anhydride, 2 mL NMP and 0.5 mL DIEA for 3×10 minutes, then washed with NMP. FMOC-Propargylglycine-Otbu (Pra) was clicked onto the Lys(N$_3$) on the 2° ligand by incubating 2 eq of the Pra amino acid with 2 eq CuI and 2 eq ascorbic acid with 1 eq azide on resin in 20% piperidine/NMP for 3 hours. The resin was washed 5×4 mL with a chelating solution of 1 g sodium diethyldithiocarbamate in 20 mL NMP and 1 mL DIEA. The anchor was then built onto the 2° ligand on bead, and an N-terminal PEG$_5$-biotin tag were added. Assays were performed exactly as for the anchor ligands, except for two key differences. The biligand assays were done with 6 ug of GST-tagged PHD protein, instead of the untagged PHD that was used in the anchor pulldowns. The pull-downs were also conducted out of 1% serum in 1×TBS, as opposed to just 1×TBS. As can be seen from the pulldown, all of the biligands improved upon the anchor binding to the E17K PHD protein, but yleaf (SEQ ID NO: 43)-yksy (SEQ ID NO: 76) showed the highest signal for the E17K protein while still demonstrating the lowest off-target signal to the WT protein.

Figure 27:
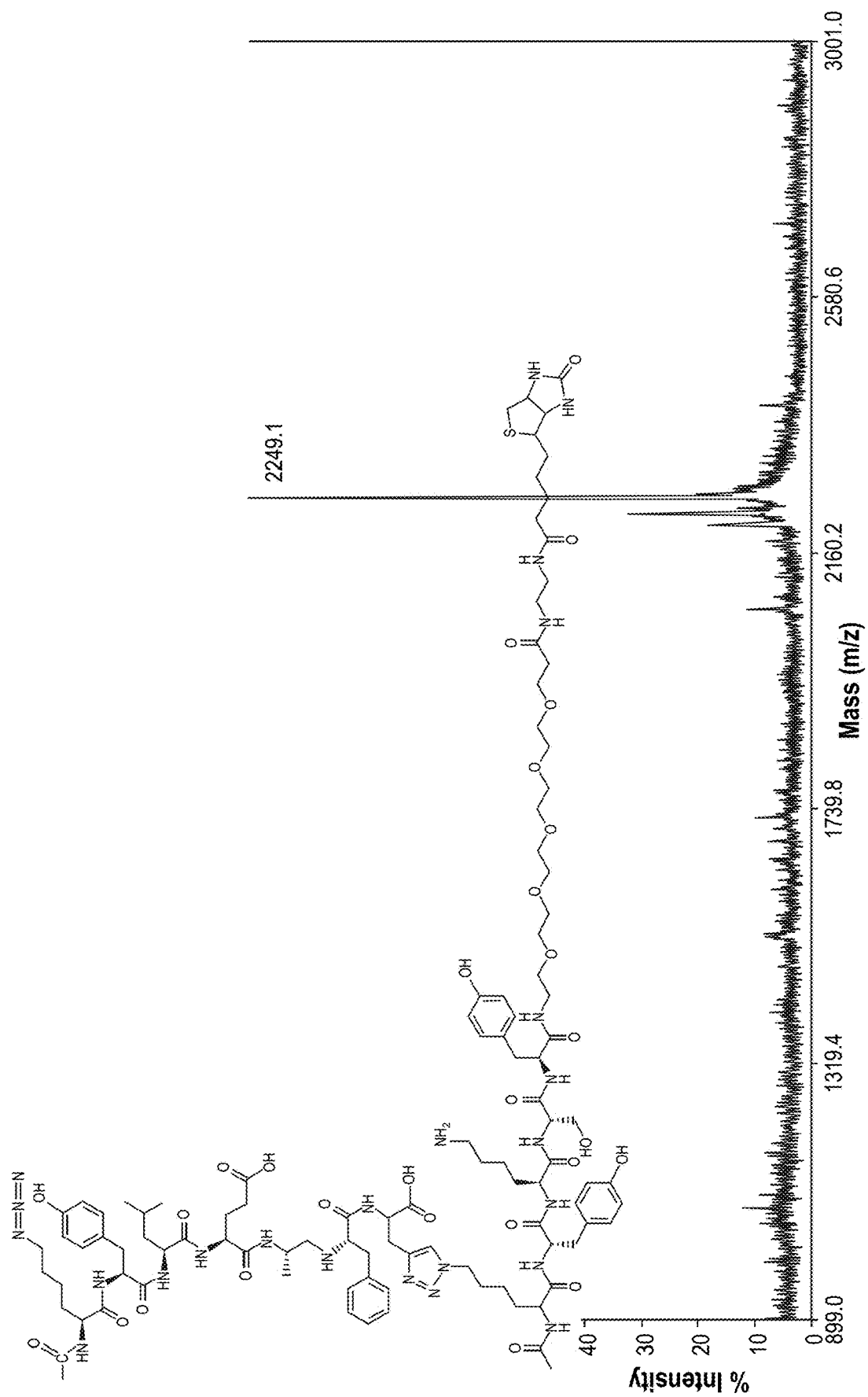
FIG. 27 is a chart showing MALDI of Lys(N$_3$)-yleaf (SEQ ID NO: 43)-yksy (SEQ ID NO: 76)-PEG5-Biotin Biligand. The biligand is appended with a C-terminal PEG5-Biotin for detection in the screen and an N-terminal Lys(N$_3$) for use in the in situ click screen. Expected: 2248.1, observed: 2249.1.

Screen for Triligand Peptide (FIG. 28):

The best biligand candidate as determined in immunoproecipitation assays—yleaf (SEQ ID NO: 43)-Tz-yksy (SEQ ID NO: 76)—was scaled up with a C-terminal PEG$_5$-biotin for detection during the assay by coupling PEG$_5$ onto NovaTag Biotin resin (EMD). Then Lys(N$_3$)-yksy (SEQ ID NO: 76) was coupled onto the resin on the Titan peptide synthesizer, and FMOC-Pra-Otbu was clicked on as above. The resin was then placed back on the Titan to synthesize the remaining "Lys(N$_3$)-yleaf (SEQ ID NO: 43)" portion—the Lys(N$_3$) serving as the click handle for the triligand screen. The biligand was then TFA cleaved from the resin and purified (FIG. 27). The screens were completed using a random 5 D-amino acid library with a C-terminal D-propargylglycine alkyne click handle, and were otherwise performed exactly as for the biligand, including all concentrations. Only 3 hit beads were discovered in this screen, and the first hit had a nonsensical sequence so could not be used. See Table 4 for hits. Both of the hits were scaled up and tested for binding using ELISA assays using the protocol for the full ELISA curves for the ligands.

Peptide Library Construction:

Peptide libraries were synthesized on a Titan 357 split-and-mix automated peptide synthesizer (Aapptec) via standard FMOC SPPS coupling chemistry[18] using 90 µm Tenta-Gel S—NH$_2$ beads. Libraries contain 18 D-stereoisomers of the natural amino acids, minus Cysteine and Methionine, at each of five randomized positions and an azide or alkyne in situ click handle. At least a five-fold excess of beads is used when synthesizing libraries to ensure oversampling of each sequence. Amino acid side-chains are protected by TFA labile protecting groups that are removed all at once following library synthesis.

Bulk Peptide Synthesis:

Bulk synthesis of peptide sequences was performed using standard FMOC SPPS peptide chemistry and purified via reverse-phase HPLC. All peptides are checked for correct mass and impurities using MALDI-TOF MS.

Design of Epitope-Targeting Anchor/Target Peptide:

Epitope targeting for the point mutation of the PH Domain of Akt1 was accomplished by screening against a 33-mer peptide fragment derived from the N-terminus of the PH Domain, highlighted in FIG. 1A, that contained the E17K point mutation as well as a propargylglycine (Pra) click-handle substitution (119[Pra]) for directing the in-situ click reaction near the mutated site. The fragment sequence used in these studies is MSDVAIVKEGWLKKRGKY[Pra]KTWRPRYFLLKNDG (SEQ ID NO: 1). This 33-mer fragment was capped with an N-terminal biotin label for detection in the screen, and was purified on a prep-scale Dionex U3000 HPLC with a reverse-phase C4 column (Phenomenex).

Screen for Initial Anchor Peptide (FIG. 9):

Screens were performed using a library[2] with 100% Met coupled at the C-terminus for potential MALDI TOF/TOF sequencing. The library was a comprehensive 5-mer containing 18 unnatural D-amino acids, excluding Met and Cys due to stability reasons. The N-terminus contained an azide click handle with varying carbon chain lengths—2 carbon, 4 carbon and 8 carbon—for in vivo click with the Pra on the target 33-mer. Two screens were done using 250 mg of dried library beads each, approximately equivalent to 1.5 million sequences total. The resin was first "precleared" by incubating it with the streptavidin-alkaline phosphatase and BCIP developer in order to remove any beads that bound to the these reagents. It was then incubated with the 33-mer epitope for either 5 hours or overnight for the click reaction to occur, washed extensively, and developed using streptavidin-alkaline phosphatase and BCIP. Beads that turned purple were considered hits, picked, and sequenced via Edman degradation.

Streptavidin-Agarose Immunoprecipitation (Pulldown) Assays for Binding Affinity:

Pulldown assays were done on Streptavidin Agarose resin from Invitrogen. The resin was incubated with N-terminal biotinylated anchor peptide candidates identified via the ClusterLigand sequence analysis. The anchor candidate coated beads were then incubated with either the wildtype or mutant protein to compare the selectivity of the ligands, as well as the binding ability. The bound protein was eluted and western blotted to compare the amount of protein present for each sample.

Figure 11:
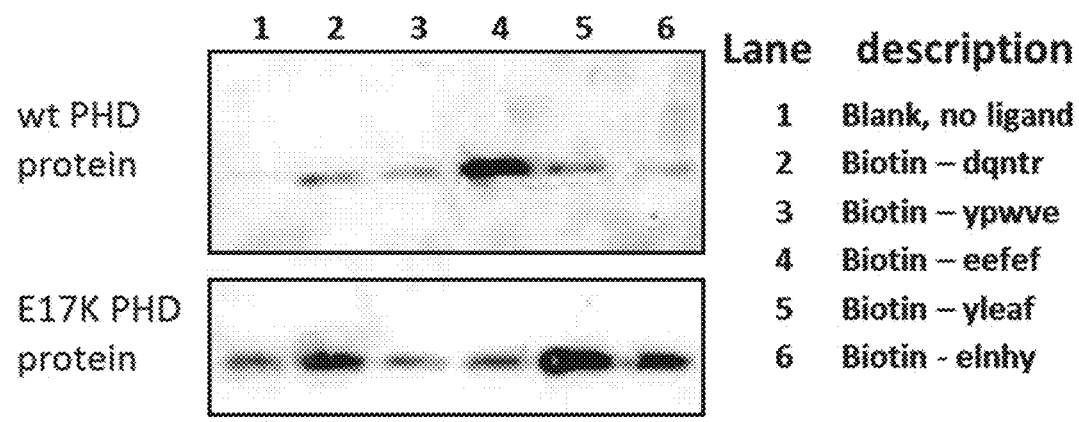
FIG. 11 shows a streptavidin-agarose pulldown assays for anchor ligand binding affinity. Streptavidin-agarose was incubated with a panel of potential anchor sequences that were synthesized with biotin tags. These resins were then incubated with either wildtype or E17K Mutant PHD to measure the amount of pulldown for each potential anchor ligand.

Relative protein band sizes were analyzed to compare binding between the anchor candidates and were used to determine selectivity for either wildtype or mutant PH Domain (FIG. 11). From these assays, eefef (SEQ ID NO: 77) was chosen as an anchor ligand for wildtype PH Domain, as it showed the only pulldown of the wildtype protein as well as the least pulldown for the mutant protein. For the mutant protein, yleaf (SEQ ID NO: 43) was chosen, as it showed the greatest binding to the mutant with the least binding to the wildtype. Both of these ligands look fairly selective for their respective PH Domain.

Figure 13:
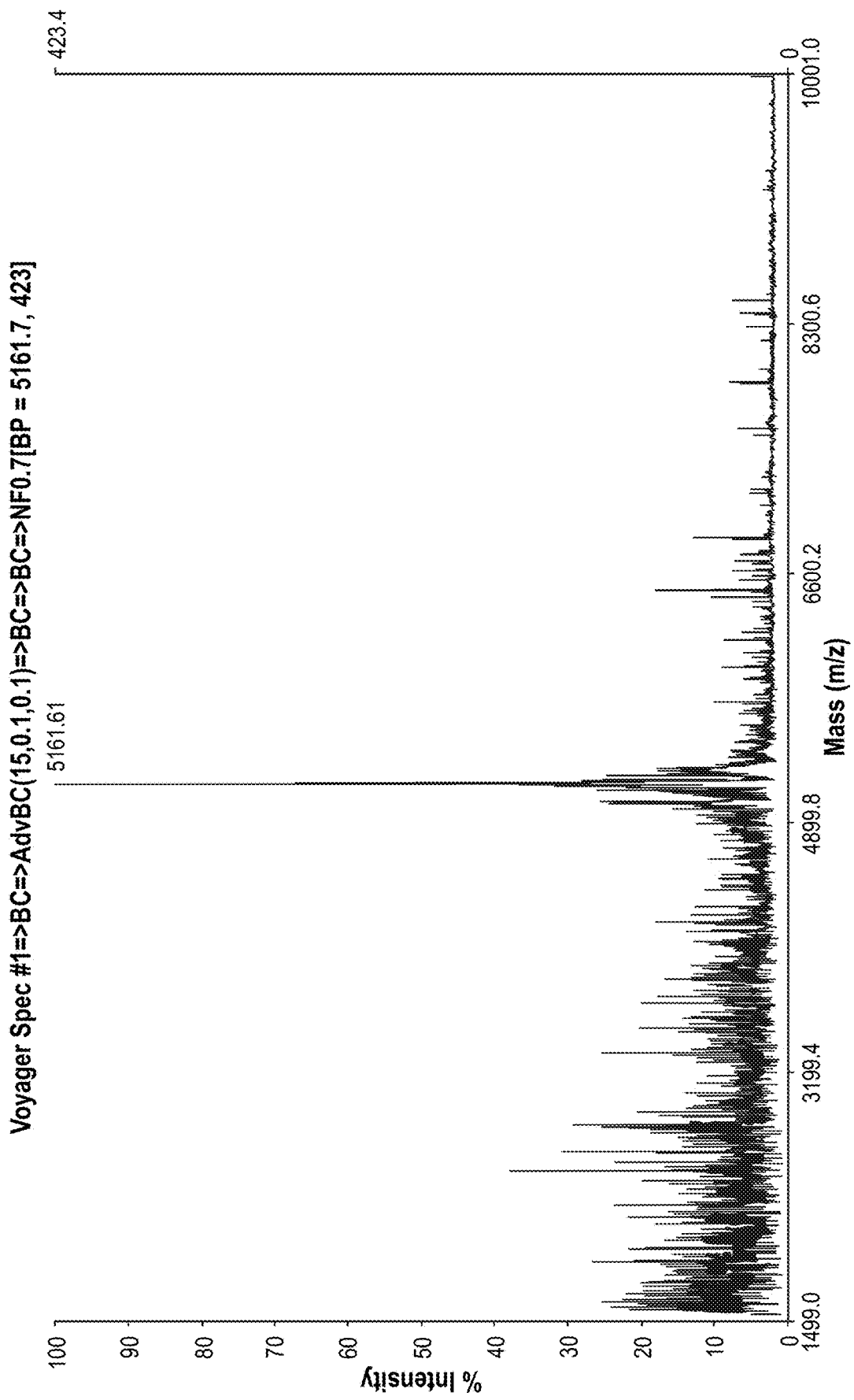
FIG. 13 is a chart showing MALDI-TOF of 6His (SEQ ID NO: 4)-PEG5-Mut 33mer Fragment ("6 His" disclosed as SEQ ID NO: 4): Sequence: HHHHHH-PEG5-MSDVAIVKEGWLKKRGKY[Pra]KTWRPRYFLLKNDG (SEQ ID NOS 4 and and 1, respectively, in order of appearance). Expected: 5160.72, observed: 5161.61.

Point ELISAs with Anchor Ligand and 33-Mer Epitope-Epitope Targeting Verification The 33-mer epitope used in screening was resynthesized without the alkyne click handle and with a 6-His tag (SEQ ID NO: 4) as an orthogonal tag to the biotin on the anchor ligand. This tag was added after a $PEG_5$ on the N-terminus of the peptide, and was made and purified as was previously described (FIGS. 13 and 14).

For these assays, 100 nM Biotin-$PEG_5$-yleaf (SEQ ID NO: 43) (FIG. 12) was immobilized for one hour on a neutravidin-coated ELISA plate (Pierce). The plate was blocked in 5% BSA in 1×TBS for one hour, then again overnight at room temperature. The immobilized anchor was then incubated with either 1 µM or 100 nM wildtype 33-mer epitope or 1 µM or 100 nM E17K mutant 33-mer epitope for one hour. The plate was washed three times with 1×TBS+0.1% Tween-20 and tapped dry. The epitope was then detected by a 1:1,000 dilution of an anti-his mouse mAb (ab18184, Abcam) for one hour, washed as above, and then detected with 1:10,000 dilution of an anti-mouse HRP-conjugated goat pAb (Abcam) for one hour. The plate was once again washed and developed with a 1:1 TMB substrate (KMB) for 15 minutes. To graph the data, the blank (epitope and antibodies binding to plate with no anchor ligand present) was subtracted from the triplicate sample values. The fraction bound was found by setting the highest value to 100% and normalizing the rest accordingly. The triplicate values were then graphed (FIG. 1C) with their error bars and the p-values were calculated by GraphPad.

HPLC-Detected Immunoprecipitation (Pulldown) Assays—Epitope Targeting Verification Pulldown assays with the biotinylated anchor and his-tagged 33-mer epitope were performed to verify epitope targeting. As with the full-protein assays, the biotinylated anchor ligand was incubated for one hour with 50 µL of streptavidin agarose slurry that had been washed three times with 1×TBS. The anchor ligand was washed out, and the resin was blocked for an hour in 5% BSA in 1×TBS. 200 µL of a 50 µM solution of the his-tagged 33-mer epitope in 1×TBS was added to the blocked resin and this was incubated overnight (~16 hours) at 4° C. Because small peptide fragments like the 33-mer epitope are difficult to transfer to and detect on the nitrocellulose membrane as for a traditional Western blot, the amount of binding in these assays was detected via HPLC. In order to do this, the bound 33-mer peptide fragments were washed three times with 1×TBS+0.5% BSA and one time with 1×TBS. The resin was then incubated with 200 µL of the 7M pH=2.0 Guanadine-HCl buffer used to strip beads in the screen. The Guanidine buffer was spun out of the beads in Spin-X tubes and injected onto a Beckman Coulter semi-prep HPLC with a reverse phase C18 analytical column. The peak seen on the HPLC (FIG. 15) illustrated how much of the 33-mer epitope bound to either the yleaf (SEQ ID NO: 43) anchor or to blank beads.

These assays in conjunction with the point ELISAs described above demonstrate the binding of the anchor ligand to the epitope that was used for screening in a variety of different conditions. The results conclusively demonstrate that the yleaf (SEQ ID NO: 43) anchor not only binds to the epitope fragment, but is selective for the single amino acid E17K mutation on both the full protein and fragment.

Ligand-Directed Tosylate Labeling Experiments

For these assays, the yleaf (SEQ ID NO: 43) anchor was appended with an N-terminal FMOC-piperidine-4-carboxylic acid as a linker on 300 mg of rink amide resin in NMP using standard FMOC amino acid coupling techniques. The resin was equilibrated in anhydrous DCM and 250 µL of 3-(chlorosulfonyl)benzylchloride was added with 450 µL of DIEA and shook for 30 minutes at room temperature. Then 250 µL of 2-(2-(2-aminoethoxy)ethoxy)ethanol, 450 µL of DIEA and 19 mg DMAP in anhydrous DMC were added and shook overnight. The resin was washed and equilibrated in NMP and 2 eq Cy5 carboxylic acid (Lumiprobe) was coupled at 37° C. overnight using standard FMOC coupling techniques. The resin was washed, TFA cleaved and HPLC purified as usual.

Figure 17:
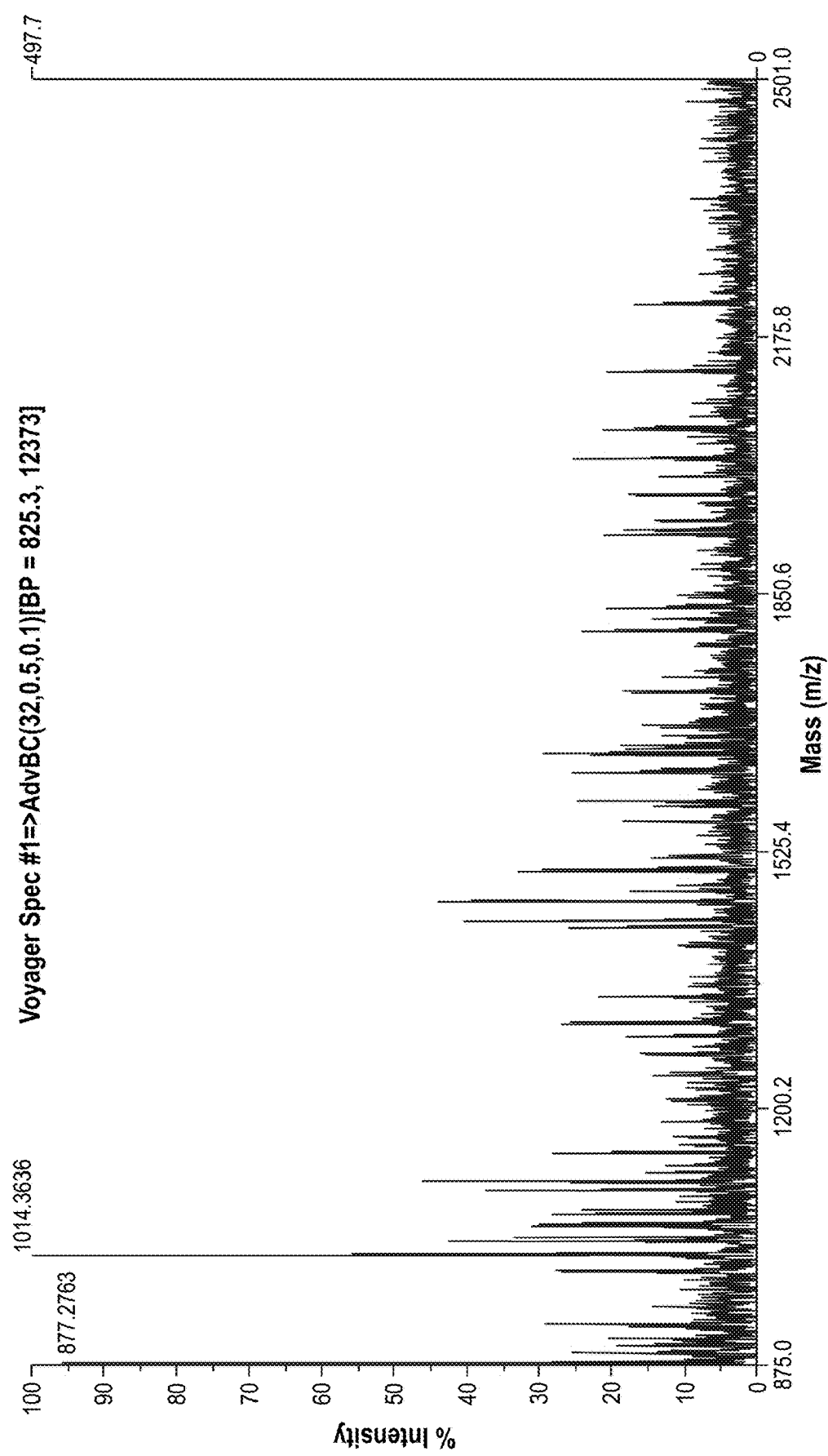
FIG. 17 is a chart showing MALDI-TOF of Cy5 unlabeled trypsin digests from tosyl labeling experiments. The unlabeled GST-E17K PHD-Akt1 protein was trypsin digested and the fragments were analyzed by MALDI-TOF MS.

In order to label the protein, 50 μL of full-length GST-E17K Akt1 from SignalChem was treated with 10× molar excess of the anchor ligand with the tosylate dye label and incubated for two days at room temperature. The mixture was lyophilized after two days and then denatured by boiling in SDS-PAGE loading buffer. The labeled protein was run alongside an unlabeled control on an Any-$K_D$ gel from Biorad, then imaged on an Odyssey fluorescent gel reader at 700 nm emission (FIG. 2B). After confirming that labeling had occurred, the gel was stained with BioSafe Coomassie blue stain (BioRad) and the blue protein bands were cut out. The gel pieces were trypsin digested using the Pierce In-gel Digest Kit. The tryptic fragments from both the unlabeled and labeled protein digests were lyophilized to concentrate them, taken up in 2 μL of 50% $H_2O$/50% Acetonitrile and were analyzed by MALDI TOF MS (FIGS. 17 and 18).

Initially, analyses were performed by taking any peak that was present in the labeled protein sample that was not present in the unlabeled sample. The weight of the dye labeling arm—552.37 g/mol—was subtracted from these peaks and the corresponding tryptic fragment was located. This provided four potential fragment candidates that were all located near the 33-mer epitope in the PH domain of the protein. Next, every MALDI peak in the labeled sample was analyzed by subtracting the weight of the dye label and comparing it to a potential tryptic fragment (Table 3). One other fragment was identified using this method, and corresponded to the doubly labeled peak of one of the previously identified labeled fragments. These results confirmed multiple previous experiments done using LC/MS techniques that proved not strong enough to fragment the tryptic peptides into individual amino acids.

Figure 20:
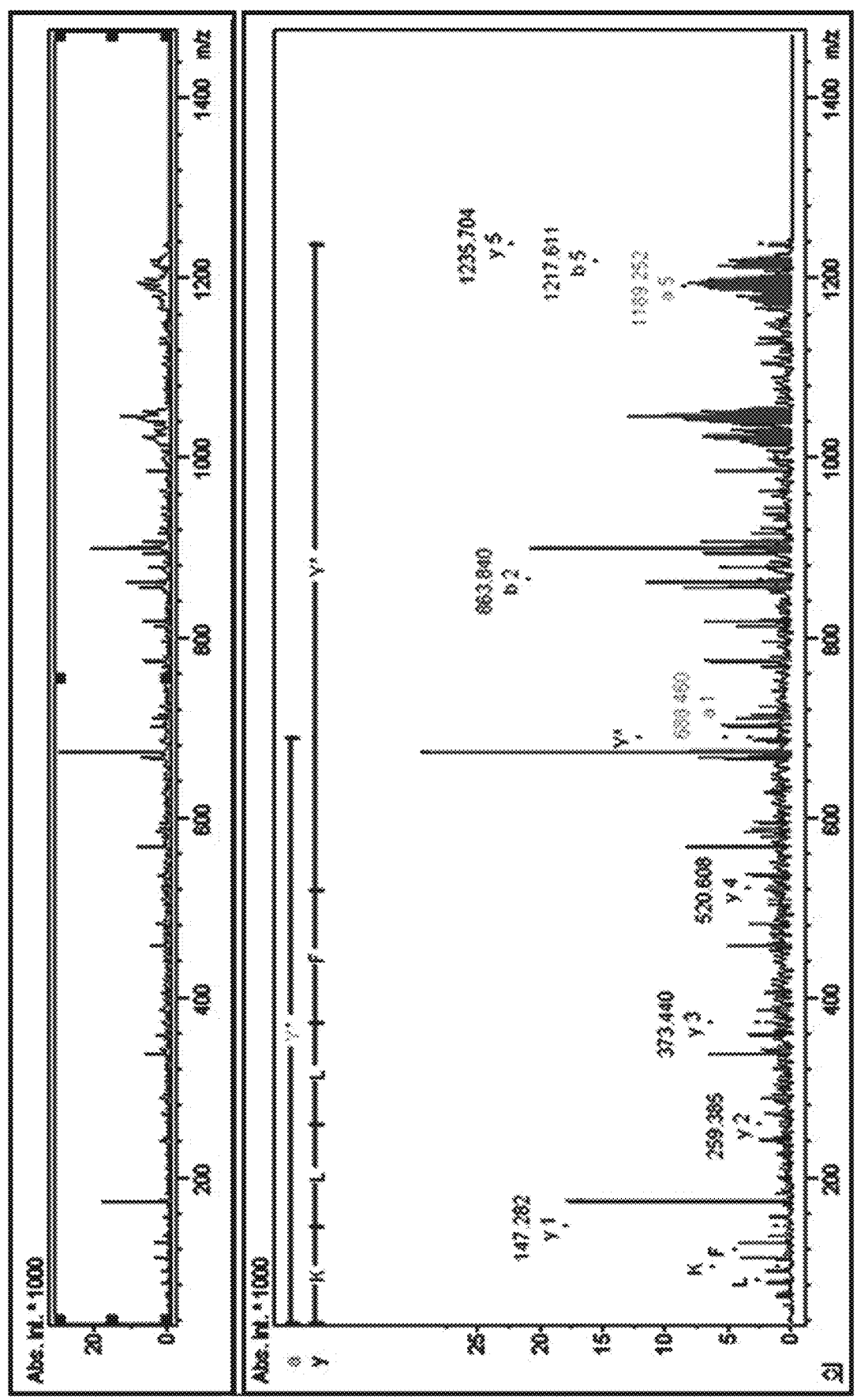
FIG. 20 is a chart showing MALDI-TOF/TOF Cy5 dye-labeled YFLLK (SEQ ID NO: 5) fragmentation. The YFLLK (SEQ ID NO: 5)-Cy5 Labeled trypsin fragment analyzed by MALDI-TOF/TOF MS. The fragments shown above demonstrate that the Cy5-dye is on the Y amino acid, which corresponds to the results found by authors of the original technique.

These tryptic peptide samples were then analyzed by MALDI TOF/TOF MS to identify the exact amino acid that contained the dye label. Only YFLLK (SEQ ID NO: 5) was able to be successfully fragmented (FIG. 20), and these the TOF/TOF confirmed that the tyrosine was the label-containing amino acid. This confirms the results seen in the original publication[19] that only Y, H, and E nucleophilic amino acids are labeled using this technique. The remaining trypic fragments all contain at least one of these amino acids, with the double labeled fragment containing two.

Figure 21:
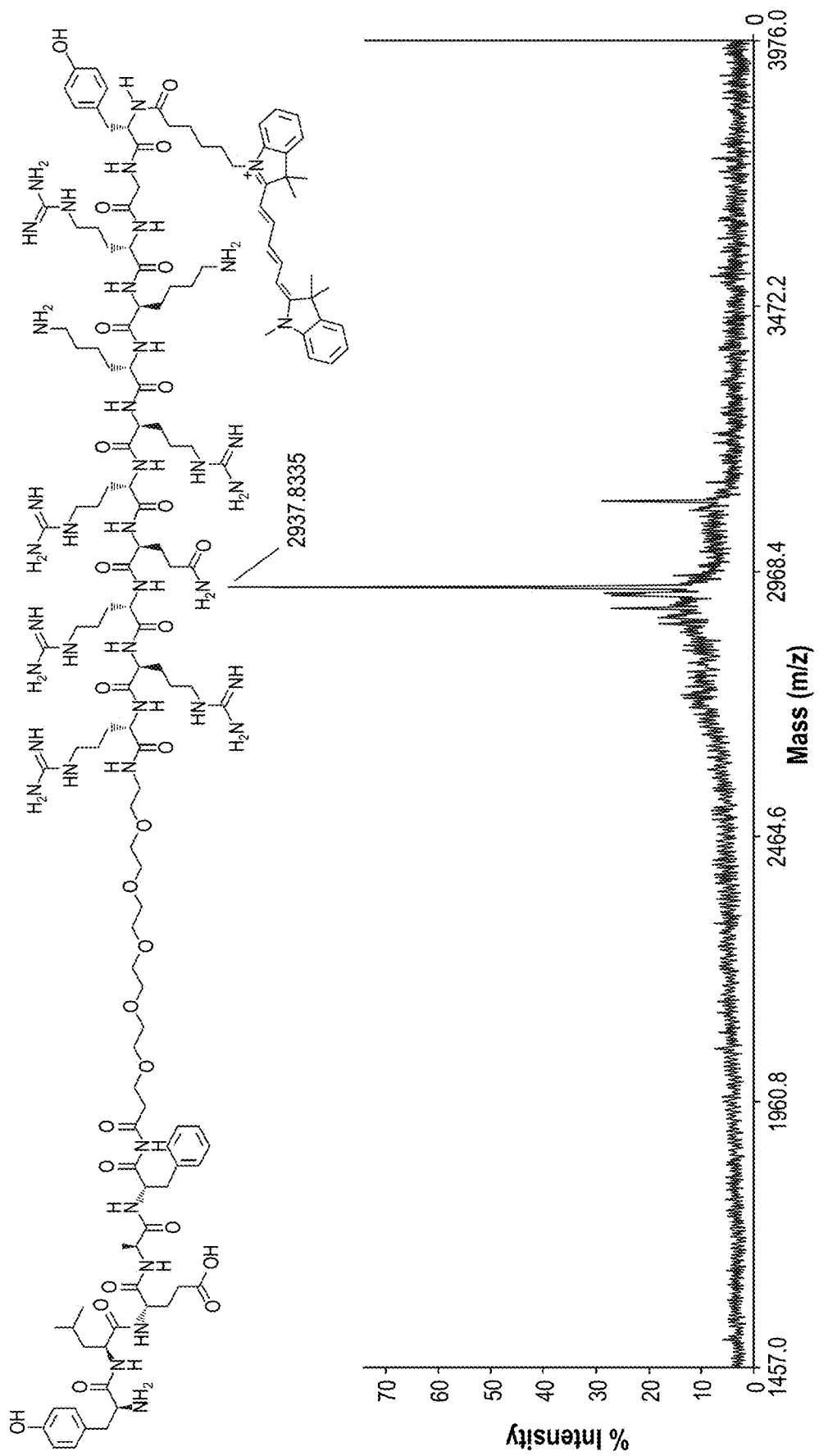
FIG. 21 is a chart showing structure and MALDI-TOF of yleaf (SEQ ID NO: 43)-PEG5-TAT-Cy5 for imaging studies. The anchor ligand is appended with a PEG5-TAT, to ensure cell penetration, then a Cy5 dye is added for visualization. Expected: 2937.72, observed: 2937.83.
Figure 22:
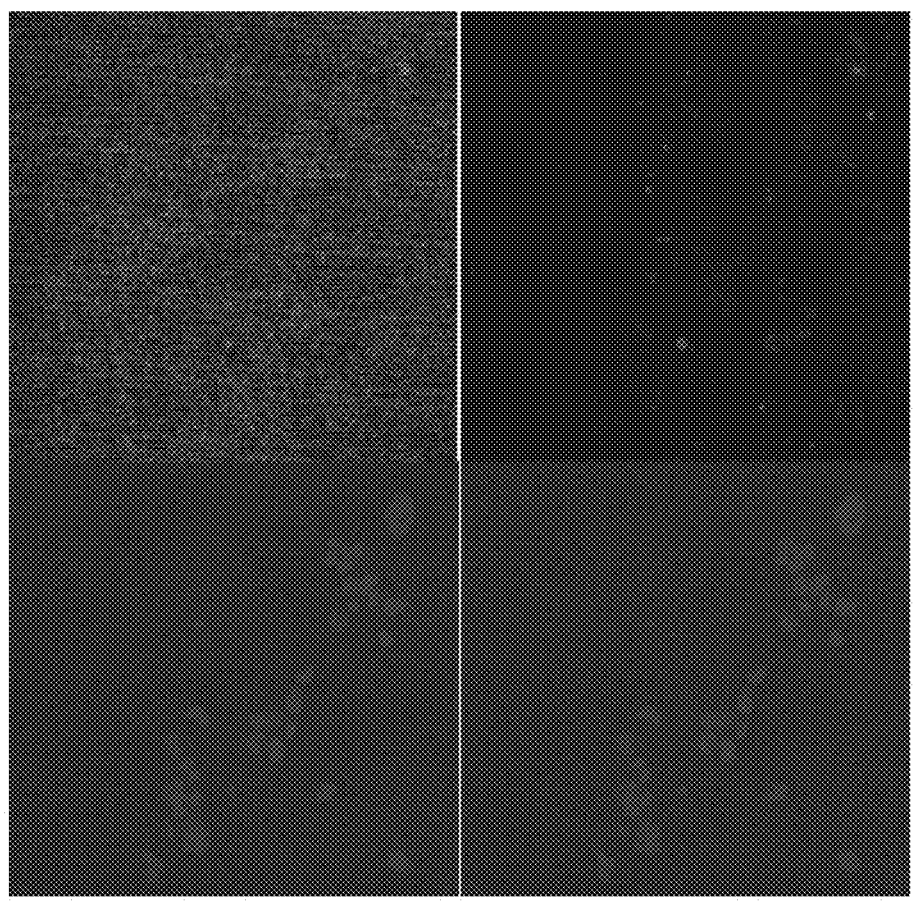
FIG. 22 shows in cell imaging no GFP-PH domain transfection control. This control was designed to prove that the ligand binding is due to the presence of the E17K GFP-PH Domain in the cells. These cells were not transfected to express the GFP PH Domain protein, then were treated with 50 nM concentration of yleaf (SEQ ID NO: 43)-PEG5-TAT-Cy5. There is no GFP signal and no Cy5 present in the cells. This indicates that the retention of the ligand with the Cy5 dye is due to the presence of the transfected protein. It is also to be noted that the GFP-PH Domain protein caused cell death, so there were very few dead cells in the non-transfected controls relative to the transfected ones.
Figure 23:
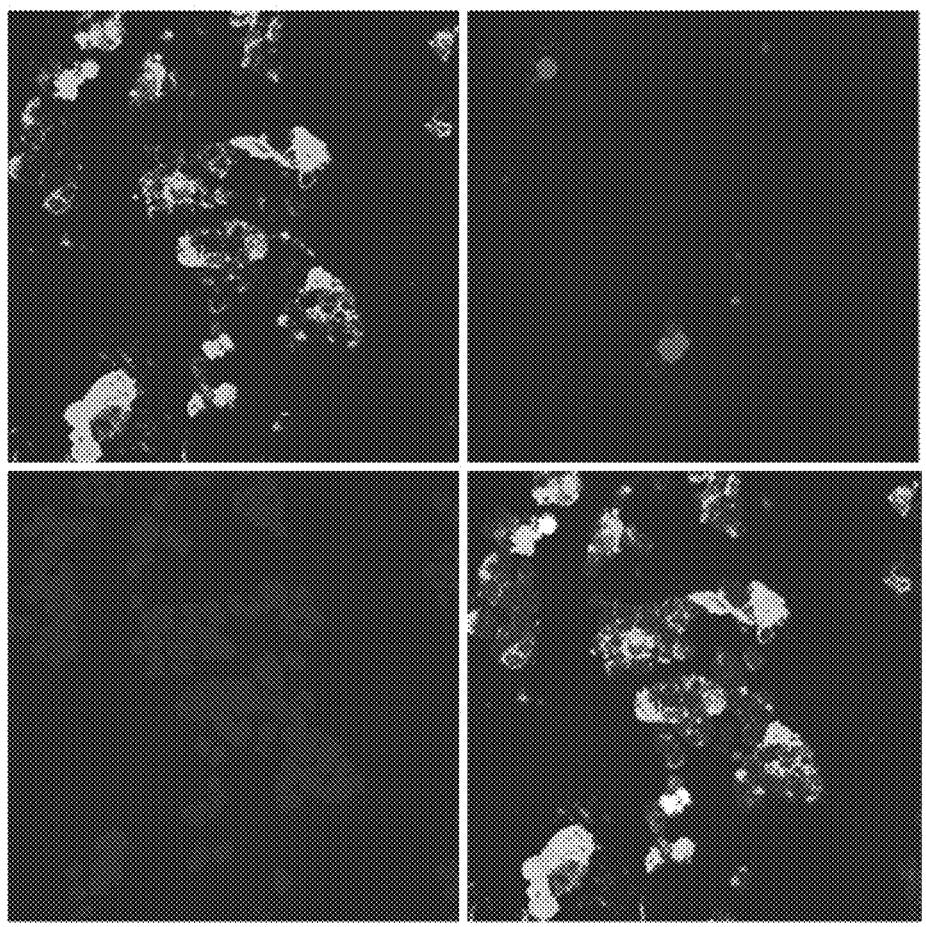
FIG. 23 shows in cell imaging PEG5-TAT-Cy5 control. Cells were incubated with 50 nM PEG5-TAT-Cy5 with no anchor ligand peptide to ensure binding is due to the yleaf (SEQ ID NO: 43) anchor ligand. The binding looks the same as the WT PH Domain images. The only cells that appear to have Cy5 are the few dead ones. The binding seen in the E17K mutant cells is due to the presence of the anchor ligand.

The labeling sites were then plotted onto a Pymol image (FIG. 2C) that combined the Akt1 protein (PDB: 3O96) and the E17K PH Domain (PDB: 2UZR) with the N-terminal GST tag (PDB: 1UA5) that was present on the full-length protein from SignalChem that was used in these labeling assays. This Pymol-made fusion protein was used to approximate what the commercial protein looked like in solution and give an idea of the extent of the selectivity of this assay. The concentration of labeling sites only surrounding the epitope demonstrate the exclusive binding of this ligand in solution. Images of anchor ligand in HEK-293T cells expressing PH Domains These experiments were designed to visualize the dye-labeled anchor ligand in cells overlapping with the GFP-labeled PH Domain proteins. For this reason, the yleaf (SEQ ID NO: 43) anchor ligand was synthesized with an N-terminal $PEG_5$, TAT (YGRKKRRQRR) (SEQ ID NO: 17), and Cy5 dye (FIG. 1B R3). GFP-tagged protein DNA was also cloned as described above. HEK-293T cells were grown in DMEM media supplemented with 10% FBS (both Invitrogen), 100× non-essential amino acid solution (Sigma), and PenStrep antibiotic (Invitrogen). Once the cells reached ~80% confluency, they were treated with trypsin to remove from the plate and split into small wells with a D-poly-lysine (BD) coverslip at approximately a 50% confluency in 1 mL total volume. The cells were allowed to attach to the coverslips for approximately 24 hours, then were transfected to express either wildtype GFP-PH domain or E17K mutant GFP-PH domain proteins using XtremeGene HD transfection agent at a ratio of 3:1 transfection agent to DNA. Several wells were left untreated as no protein blanks (FIG. 22). The cells were given 24 hours to express protein. They were then serum starved for one hour in DMEM media prepared as above, but without the FBS. After one hour, the Cy5-labeled anchor was added to the wells to a final concentration of 50 nM. As the HEK-293T cells are expressing endogenous Akt1 protein, this level was adjusted to give the lowest background signal possible. The protein blank cells were also incubated with 50 nM of the yleaf (SEQ ID NO: 43) anchor to ensure that binding was due to the presence of the E17K mutant protein (FIG. 23). A blank of PEG5-TAT-Cy5 was also added to wells expressing either wildtype or E17K mutant to ensure that ligand binding was due to the presence of the yleaf (SEQ ID NO: 43) anchor. After a one hour incubation with the peptide, the cells were washed once in serum starved media, then incubated thirty minutes in serum starved media to wash out any excess peptide. During this time, the cells were also treated with 10 μg of Hoescht 33342 dye to stain the nuclei. After the thirty minute period, one well of each wildtype or mutant protein with peptide were activated with PDGF for 10 minutes. The cells were then washed twice with cold PBS buffer, fixed with 10% Neutral Buffered Formalin Solution (Sigma) and glued onto microscope slides. Images were taken on a Zeiss LSM 510 Meta NLO with Coherent Chameleon confocal microscope. A 40× Plan-apochromat lens was used. The laser intensity and gain were fixed for all pairs of images between wildtype and mutant samples to ensure that the differences seen were not artificially created. Screen for Biligand Peptide (FIG. 21):

The anchor determined above—yleaf (SEQ ID NO: 43)—was scaled up with a biotin on the N-terminus for detection, a PEG5 linker between the biotin and the peptide, and a d-propargylglycine (Pra) on the C-terminus as the in situ click handle (Biotin-$PEG_5$-yleaf (SEQ ID NO: 43)-Pra) (FIG. 12). Screens were done using a library with 100% Met coupled at the C-terminus for potential MALDI TOF/TOF sequencing. The library consisted of a comprehensive 5-mer containing 18 unnatural D-amino acids, excluding Met and Cys due to stability reasons. The N-terminus contained an azide click handle with a 4 carbon chain ($Lys(N_3)$)— for in vivo click with the Pra on the anchor peptide. Screens were done with 300 mg of dried library beads.

Figure 29:
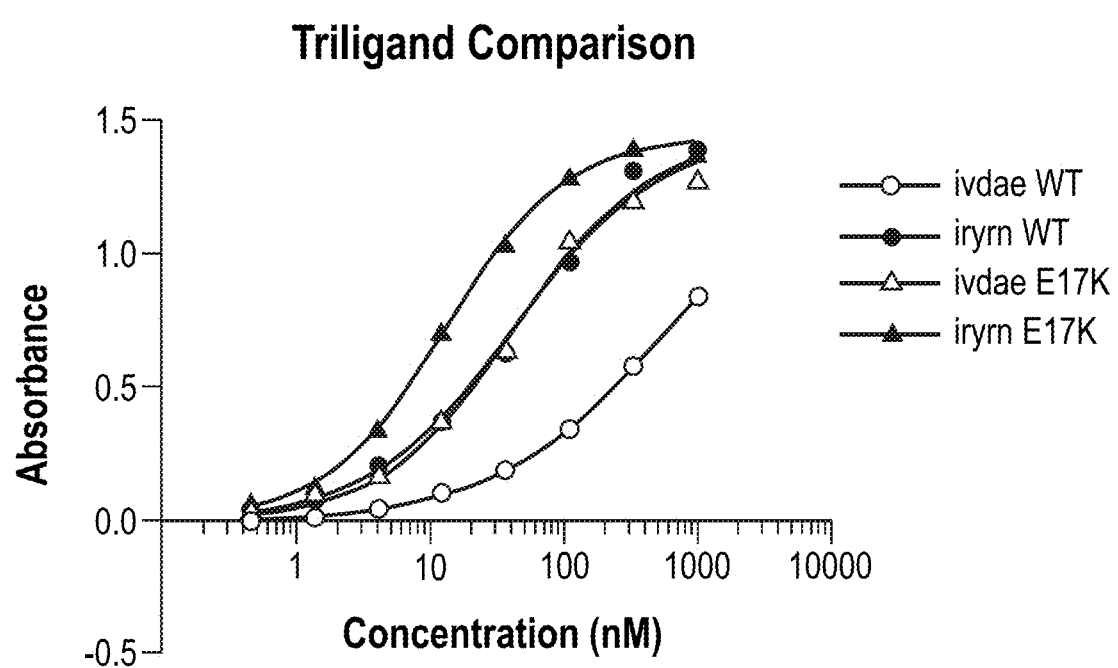
FIG. 29 is a graph showing results from an ELISA assay of two triligand candidates. The triligand candidate irym (SEQ ID NO:92) shows a significant improvement on the binding affinity for the E17K protein, but an even bigger increase for the WT protein. The ivdae (SEQ ID NO: 78) candidate does not show an affinity increase for the E17K protein, but maintains the selectivity over the WT protein. The ivdae (SEQ ID NO: 78) candidate was carried forward as the final triligand.
Figure 30:
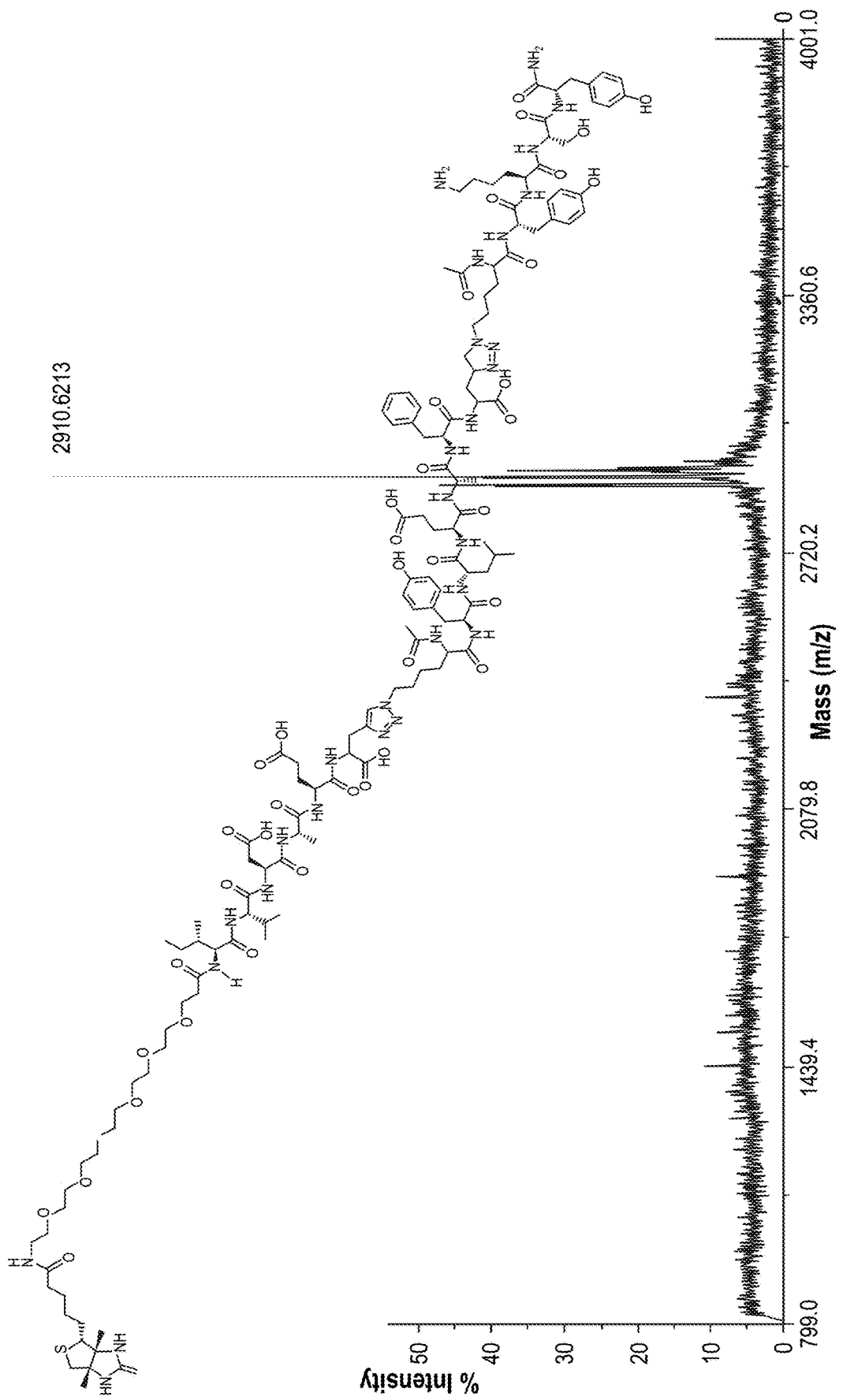
FIG. 30 is a chart showing structure and MALDI-TOF of Biotin-PEG5-ivdae (SEQ ID NO: 78)-yleaf (SEQ ID NO: 43)-yksy (SEQ ID NO: 76) triligand. The triligand was appended with a biotin tag for detection. Expected: 2888.39, Observed: 2888.68 (M+H), 2910.62 (M+Na).

The first screening step, the preclear, was performed as per the anchor ligand screens, except that the biligand was included in order to remove sequences with an affinity for this ligand. A target screen was then conducted in which the biligand and the E17K PH Domain protein were incubated with the library overnight in order for a click reaction to occur. The screen was developed for the presence of target on bead by detecting with an anti-6His-alkaline phosphatase antibody ("6His" disclosed as SEQ ID NO: 4) that would detect the his-tagged protein. These hit beads were then incubated with the WT PH Domain protein in order to detect which ones exhibit off-target binding, and these hits (detected via anti-6 his antibody ("6 his" disclosed as SEQ ID NO: 4)) were removed from the pool. The final screening stage involved detection of the in situ click product via streptavidin-alkaline phosphatase. Screen for Triligand Peptide (FIG. 28):

The best biligand candidate as determined in immunoproecipitation assays—yleaf (SEQ ID NO: 43)-Tz-yksy (SEQ ID NO: 76)—was scaled up with a C-terminal PEG$_5$-biotin for detection during the assay by coupling PEG$_5$ onto NovaTag Biotin resin (EMD). The screens were completed using a random 5 D-amino acid library with a C-terminal D-propargylglycine alkyne click handle, and were otherwise performed exactly as for the biligand, including all concentrations. Only 3 hit beads were discovered in this screen, and the first hit had a nonsensical sequence so could not be used. See Table 5 for hits. Both of the hits were scaled up and tested for binding using ELISA assays using the protocol for the full ELISA curves for the ligands (FIG. 29).

Full ELISA Curves for Ligands

The full curve ELISAs were obtained using streptavidin coated ELISA plates (Pierce). The ligands—anchor, biligand, triligand and "eflya" scrambled anchor peptide blank—were laid down at a concentration of 1 µM for one hour. Two lanes of each ligand were used on the plate for both proteins—WT and E17K GST-PH Domain. The plates were blocked with 5% BSA for two hours. Dilutions of both WT and E17K GST-PH Domain proteins were made in 0.5% BSA in 1×TBS starting from 1 µM-0.5 nM by serially diluting 1:2 down a series of 8 samples. For each ligand, a no protein blank was also used. The proteins were incubated with the blocked plate for one hour, washed 3× with 1×TBST+0.5% BSA and tapped dry, then detected with a 1:10,000 dilution of an HRP conjugated anti-GST pAb. The plate was again washed 3× with 1×TBST and tapped dry. It was developed with a 1:1 solution of TMB substrate and development was stopped with 1M H$_2$SO$_4$ and read on a plate reader. The curves in FIG. 4B were plotted by normalizing the signal by the blank wells, and were fitted to a Hill function in GraphPad using a common saturation and slope (Bmax=1.466+/−0.03, h=0.7383+/−0.025).

Point ELISA assays for Triligand Binding to Akt1 and Akt2 Wildtype and E17K Mutant These assays were conducted to test the binding of the triligand to the off-target Akt2 wildtype and mutant proteins. For this assay, all samples were taken in triplicate for statistical purposes. Triligand peptide was first immobilized onto neutravdin ELISA plates (Pierce) for one hour. A scrambled anchor peptide, eflya, was used as the no-ligand blank, as the GST proteins has significant background binding to a blank neutravidin plate. The plates were then blocked with 5% BSA overnight. Protein was laid down at a concentration of 100 nM for samples wells and the blank, scrambled peptide wells. GST protein alone (Abcam) was also incubated with the triligand and scrambled peptide as a control. The proteins were incubated for one hour, then washed three times with 1×TBST. The protein was then detected with 1:10,000 anti-GST mouse mAb (Fisher, #MA4-004) for one hour, washed three times with 1×TBST and developed with a 1:1 mixture of TMB substrate for ten minutes. The samples were plotted by subtracting the blanks and averaging the sample wells. The highest signal was considered 100% binding, and the other samples were normalized accordingly.

PIP$_3$ Agarose Inhibition Assays:

PIP3 Agarose beads (Echelon) were used to detect for the inhibition of PH Domain binding to its substrate, PIP3, upon incubation with the anchor candidate peptide ligands. To test the inhibition of each of the ligands, anchor biligand and triligand, 20 µL of resin slurry was added to each of four tubes and washed three times with 1×TBS. Protein, 2 µg (234 nM) of E17K mutant, was preincubated for one hour at room temperature with either DMSO (no protein blank), anchor, biligand or triligand at 2.38 µM (10× in relation to protein) in 200 µL of 1×TBS. For the control, mutant PH Domain was incubated with 1×TBS and 1 µL MSO to mimic the ligand conditions. These protein samples were then added to PIP3 agarose in a Spin-X tube and incubated at room temperature for two hours. The resin was washed three times with 1×TBS with 0.25% IGEPAL CA-630, spun out to dry completely, then denatured with 50 µL 3×SDS gel loading buffer for 10 min at 95° C. The gel loading buffer was spun out of the resin and detected via western blot as per the Streptavidin-Agarose Pulldowns. Inhibition was indicated by a decrease in the amount of PH Domain that was pulled down by the resin. See FIG. 4D.

Expanded inhibition blots with either WT of E17K mutant protein were performed in a similar fashion. Twelve tubes of 20 µL of PIP3 agarose were washed three times with 1×TBS. 2 µg of either wildtype or mutant PH Domain-GFP protein (234 nM) in 200 uL 1×TBS were preincubated for 30 minutes with differing concentrations of triligand: 0.1 eq (23.4 nM), 1 eq (234 nM), 10 eq (2.34 µM), 100 eq (23.4 µM), and 1000 eq (234 µM). The protein and triligand solutions were then incubated with the PIP3 resin for 2 hours at room temperature. The resins were washed, eluted, and blotted as per all PH Domain western blots. See FIG. 4D.

REFERENCES

1 Rusling, J. F., Kumar, C. V., Gutkind, J. S. & Patel, V. Measurement of biomarker proteins for point-of-care early detection and monitoring of cancer. Analyst 135, 2496-2511, doi:10.1039/C0AN00204F (2010).
2 Chong, C. R. & Janne, P. A. The quest to overcome resistance to EGFR-targeted therapies in cancer. Nat Med 19, 1389-1400, doi:10.1038/nm.3388 http://www.nature.com/nm/journal/v19/n11/abs/nm.3388.html#supplementary-information (2013).
3 Tjin Tham Sjin, R. et al. In vitro and In vivo Characterization of Irreversible Mutant-Selective EGFR Inhibitors that are Wild-type Sparing. Molecular Cancer Therapeutics, doi:10.1158/1535-7163.mct-13-0966 (2014).
4 Capper, D., Zentgraf, H., Balss, J., Hartmann, C. & von Deimling, A. Monoclonal antibody specific for IDH1 R132H mutation. Acta neuropathologica 118, 599-601, doi:10.1007/s00401-009-0595-z (2009).
5 Yu, J. et al. Mutation-Specific Antibodies for the Detection of EGFR Mutations in Non-Small-Cell Lung Cancer. Clinical Cancer Research 15, 3023-3028, doi:10.1158/1078-0432.ccr-08-2739 (2009).
6 Capper, D. et al. Assessment of BRAF V600E mutation status by immunohistochemistry with a mutation-specific monoclonal antibody. Acta neuropathologica 122, 11-19, doi:10.1007/s00401-011-0841-z (2011).
7 Marschall, A. L. J., Frenzel, A., Schirrmann, T., Schungel, M. & Dubel, S. Targeting antibodies to the cytoplasm. mAbs 3, 3-16 (2011).
8 Rondon, I. J., Marasco & A., W. INTRACELLULAR ANTIBODIES (INTRABODIES) FOR GENE THERAPY OF INFECTIOUS DISEASES. Annual Review of Microbiology 51, 257-283, doi:doi:10.1146/annurev.micro.51.1.257 (1997).
9 Kodadek, T., Reddy, M. M., Olivos, H. J., Bachhawat-Sikder, K. & Alluri, P. G. Synthetic molecules as antibody replacements. Accounts of chemical research 37, 711-718, doi:10.1021/ar0301451 (2004).
10 Testa, J. R. & Tsichlis, P. N. AKT signaling in normal and malignant cells. Oncogene 24, 7391-7393, doi:10.1038/sj.onc.1209100 (2005).

11 Vivanco, I. & Sawyers, C. L. The phosphatidylinositol 3-Kinase-AKT pathway in human cancer. Nat Rev Cancer 2, 489-501 (2002).

12 Carpten, J. D. et al. A transforming mutation in the pleckstrin homology domain of AKT1 in cancer. Nature 448, 439-444, doi: http://www.nature.com/nature/journal/v448/n7152/suppinfo/nature05933_S$_1$.html (2007).

13 Nag, A. et al. A Chemical Epitope-Targeting Strategy for Protein Capture Agents: The Serine 474 Epitope of the Kinase Akt2. Angewandte Chemie International Edition 52, 13975-13979, doi:10.1002/anie.201305882 (2013).

14 Agnew, H. D. et al. Iterative In Situ Click Chemistry Creates Antibody-like Protein-Capture Agents. Angewandte Chemie International Edition 48, 4944-4948, doi:10.1002/anie.200900488 (2009).

15 Farrow, B. et al. A Chemically Synthesized Capture Agent Enables the Selective, Sensitive, and Robust Electrochemical Detection of Anthrax Protective Antigen. ACS Nano 7, 9452-9460, doi:10.1021/nn404296k (2013).

16 Millward, S. W. et al. Iterative in situ click chemistry assembles a branched capture agent and allosteric inhibitor for Akt1. Journal of the American Chemical Society 133, 18280-18288, doi:10.1021/ja2064389 (2011).

17 Pfeilsticker, J. A. et al. A Cocktail of Thermally Stable, Chemically Synthesized Capture Agents for the Efficient Detection of Anti-Gp41 Antibodies from Human Sera. PLoS ONE 8, e76224, doi:10.1371/journal.pone.0076224 (2013).

18 Coin, I., Beyermann, M. & Bienert, M. Solid-phase peptide synthesis: from standard procedures to the synthesis of difficult sequences. Nature protocols 2, 3247-3256, doi:10.1038/nprot.2007.454 (2007).

19 Tsukiji, S., Miyagawa, M., Takaoka, Y., Tamura, T. & Hamachi, I. Ligand-directed tosyl chemistry for protein labeling in vivo. Nat Chem Biol 5, 341-343, doi: http://www.nature.com/nchembio/journal/v5/n5/suppinfo/nchembio.157_S1.html (2009).

20 Pashkova, A., Moskovets, E. & Karger, B. L. Coumarin Tags for Improved Analysis of Peptides by MALDI-TOF MS and MS/MS. 1. Enhancement in MALDI MS Signal Intensities. Analytical Chemistry 76, 4550-4557, doi: 10.1021/ac049638+(2004).

21 Mahadevan, D. et al. Discovery of a novel class of AKT pleckstrin homology domain inhibitors. Molecular Cancer Therapeutics 7, 2621-2632, doi:10.1158/1535-7163.mct-07-2276 (2008).

22 Hiromura, M. et al. Inhibition of Akt kinase activity by a peptide spanning the betaA strand of the proto-oncogene TCL1. The Journal of biological chemistry 279, 53407-53418, doi:10.1074/jbc.M403775200 (2004).

23 Lee, S. S. et al. Accurate MALDI-TOF/TOF sequencing of one-bead-one-compound peptide libraries with application to the identification of multiligand protein affinity agents using in situ click chemistry screening. Anal Chem 82, 672-679, doi:10.1021/ac902195y (2010).

---

What is claimed is:

1. A capture agent that binds a variant Akt1 protein, wherein the variant Akt1 protein has been mutated from a glutamate to a lysine at position 17, wherein the capture agent comprises an anchor ligand, a secondary ligand, and optionally, a tertiary ligand, wherein the anchor ligand specifically binds the variant Akt1,
wherein the anchor ligand comprises an amino acid sequence yleaf (SEQ ID NO: 43),
wherein the secondary ligand is identified by contacting an anchor ligand selection block and a plurality of first candidate peptides with the variant Akt1 protein, wherein (a) the anchor ligand selection block comprises the anchor ligand and an azido group and the first candidate peptides each comprise a peptide and an alkynyl group or (b) the anchor ligand selection block comprises the anchor ligand and an alkynyl group and the first candidate peptides each comprise a peptide and an azido group, wherein the candidate peptides comprise five amino acids each randomly selected from 18 D-stereoisomers of the natural amino acids, minus Cysteine and Methionine, whereby a biligand is formed by a disubstituted 1,2,3-triazole linkage being formed between the anchor ligand selection block and one of the first candidate peptides by the azido group or alkynyl group of the anchor ligand selection block and the alkynyl group or azido group of the one of the first candidate peptides being brought in close proximity by binding to the variant Akt1 protein, wherein the candidate peptide with which the triazole linkage is formed with the anchor ligand selection block is identified as the secondary ligand of the capture agent,
wherein the tertiary ligand is identified by contacting a biligand selection block and a plurality of second candidate peptides with the variant Akt1 protein, wherein (a) the biligand selection block comprises the biligand and an azido group and the second candidate peptides each comprise a peptide and an alkynyl group or (b) the biligand selection block comprises the biligand and an alkynyl group and the second candidate peptides each comprise a peptide and an azido group, wherein the candidate peptides comprise five amino acids each randomly selected from 18 D-stereoisomers of the natural amino acids, minus Cysteine and Methionine, whereby a triligand is formed by a disubstituted 1,2,3-triazole linkage being formed between the biligand selection block and one of the second candidate peptides by the azido group or alkynyl group of the biligand selection block and the alkynyl group or azido group of the one of the second candidate peptides being brought in close proximity by binding to the variant Akt1 protein, wherein the candidate peptide with which the triazole linkage is formed with the biligand selection block is identified as the tertiary ligand of the capture agent.

2. The capture agent of claim 1, wherein the secondary ligand comprises the amino acid sequence selected from hwpr (SEQ ID NO: 61), nvyl (SEQ ID NO: 59), hyrw (SEQ ID NO: 55), rdyr (SEQ ID NO: 75), ynyk (SEQ ID NO: 74), yktw (SEQ ID NO: 88), srfy (SEQ ID NO: 73), yksy (SEQ ID NO: 76), yysr (SEQ ID NO: 71), rhws (SEQ ID NO: 66), pwwr (SEQ ID NO: 89), nfry (SEQ ID NO: 90), ywrl (SEQ ID NO: 57), ywkG (SEQ ID NO: 56), ayly (SEQ ID NO: 63), hwrw (SEQ ID NO: 91), nwrl (SEQ ID NO: 53), aarw (SEQ ID NO: 60), Grwy (SEQ ID NO: 72), wfri (SEQ ID NO: 58), rpyy (SEQ ID NO: 65), vwfr (SEQ ID NO: 70).

3. The capture agent of claim 1, wherein the secondary ligand comprises the amino acid sequence yksy (SEQ ID NO: 76).

4. The capture agent of claim 1, wherein the tertiary ligand comprises an amino acid sequence selected from Glm, irym (SEQ ID NO: 92), and ivdae SEQ ID NO: 78.

5. The capture agent of claim 1, wherein the tertiary ligand comprises the amino acid sequence ivdae (SEQ ID NO: 78).

6. The capture agent of claim 1, wherein the anchor ligand and secondary ligand are linked together via a 1,4-substituted-1,2,3-triazole residue (Tz4) or via a 1,5-substituted-1,2,3-triazole residue (Tz5).

7. The capture agent of claim 1, wherein the tertiary ligand is covalently bound to the secondary ligand.

8. The capture agent of claim 1, wherein the capture agent is labeled with a label selected from the group consisting of biotin, copper-DOTA, biotin-PEG$_3$, aminooxyacetate, $^{19}$FB, $^{18}$FB, 5-Carboxyfluorescein, and FITC-PEG3.

9. The capture agent of claim 1, wherein the capture agent is labeled with the detectable moiety consisting of $^{64}$Cu DOTA, $^{68}$Ga DOTA, $^{68}$Ga NOTA, $^{18}$F, Al $^{18}$F NOTA, $^{64}$Cu, $^{68}$Ga, $^{89}$Zr, $^{124}$I, $^{86}$Y, $^{94m}$Tc, $^{110m}$In, C and $^{76}$Br.

10. The capture agent of claim 1, wherein the capture agent further comprises a cell penetrating peptide.

11. The capture agent of claim 10, wherein the cell penetrating peptide is HIV-TAT.

12. The capture agent of claim 1 having the structure:

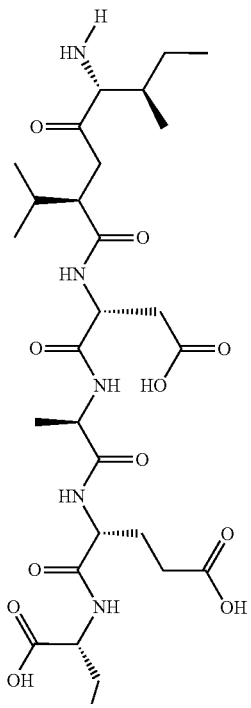

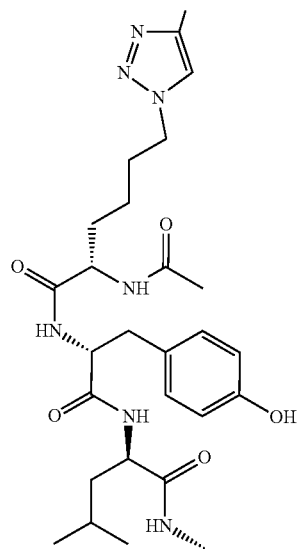

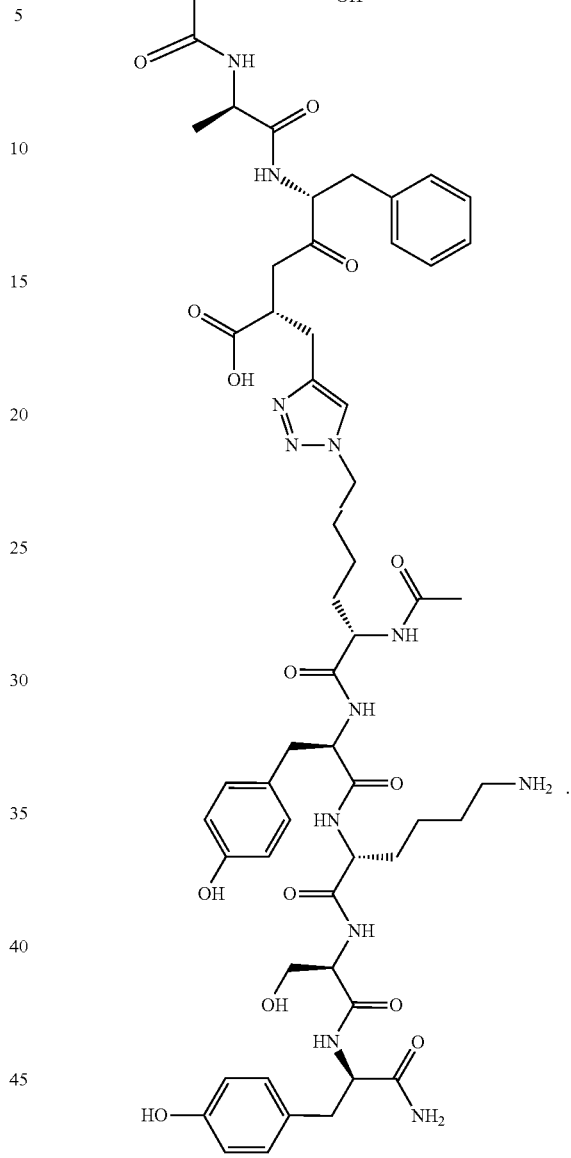

13. A composition comprising two or more capture agents of claim 1.

14. A method of monitoring treatment of a cancer associated with increased E17K Akt1 expression in a subject, comprising the steps of:
 (a) contacting a first biological sample from the subject with one or more capture agents of claim 1, wherein each capture agent is linked to a detectable moiety;
 (b) detecting the moiety linked to the capture agent, wherein the capture agent is bound to E17K Akt1;
 (c) administering a treatment for the cancer associated with increased E17K Akt1 expression to the subject;
 (d) contacting a second biological sample from the subject one or more capture agents of claim 1, wherein each capture agent is linked to a detectable moiety; and
 (e) detecting the moiety linked to the capture agent, wherein the capture agent is bound to E17K Akt1;
 (f) comparing the level of moiety detected in step (b) with the level of moiety detected in step (d);

wherein, if less of the moiety is detected in step (e) than in step (b), the treatment is improving cancer in the subject.

15. A method of detecting E17K Akt1 in a biological sample, comprising the steps of:
   (a) contacting the sample with a capture agent of claim 1, wherein the capture agent is linked to a detectable moiety; and
   (b) detecting the moiety linked to the capture agent, wherein the capture agent is bound to E17K Akt1; and
   wherein detection of the moiety indicates the presence of E17K Akt1 in the subject.

16. A multiplex capture agent comprising two or more capture agents of claim 1, wherein the multiplex capture agent binds E17K Akt1.

17. The capture agent of claim 1, wherein the Akt protein is E17K Akt1.

18. The capture agent of claim 1, wherein the capture agent further comprises a tag that comprises the amino acid sequence ALAPYIP (SEQ ID NO: 93).

19. A method of treating a cancer associated with increased E17K Akt1 expression and/or activity in a subject in need thereof, comprising administering a therapeutically effective amount of a capture agent of claim 1.

20. A method of inhibiting E17K Akt1 activity in a subject comprising administering to the subject a capture agent of claim 1.

21. A method of imaging a cancer associated with increased E17K Akt1 expression and/or activity in a subject in need thereof, comprising administering an effective amount of a capture agent of claim 1.

22. A method of synthesizing a capture agent to a target peptide comprising:
   (a) modifying a target peptide to include an azido group or an alkynyl group;
   (b) preparing a plurality of candidate peptides to select an anchor ligand for the target peptide, the plurality of peptides comprising an azido group, or an alkynyl group, if the target peptide comprises an alkynyl group, or an azido group, respectively;
   (c) contacting the plurality of candidate peptides to select the anchor ligand with the target peptide; and
   (d) selecting the capture agent biligand that has an affinity with the target protein.

* * * * *

UNITED STATES PATENT AND TRADEMARK OFFICE
CERTIFICATE OF CORRECTION

| | |
|---|---|
| PATENT NO. | : 10,975,123 B2 |
| APPLICATION NO. | : 15/680171 |
| DATED | : April 13, 2021 |
| INVENTOR(S) | : Kaycie Deyle, Blake Farrow and James R. Heath |

It is certified that error appears in the above-identified patent and that said Letters Patent is hereby corrected as shown below:

In the Claims

Claim 9, Column 98, Line 60, replace "Al$^{18}$F NOTA" with --Al[$^{18}$F] NOTA--.

Claim 9, Column 98, Line 62, replace "$^{110m}$In, C" with --$^{110m}$In, $^{11}$C--.

Claim 14, Column 100, Lines 61-62, replace "from the subject one or more" with --from the subject with one or more--.

Signed and Sealed this
Twenty-first Day of February, 2023

*Katherine Kelly Vidal*

Katherine Kelly Vidal
*Director of the United States Patent and Trademark Office*

SEQUENCE LISTING

<160> NUMBER OF SEQ ID NOS: 93

<210> SEQ ID NO 1
<211> LENGTH: 33
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (19)..(19)
<223> OTHER INFORMATION: Pra

<400> SEQUENCE: 1

Met Ser Asp Val Ala Ile Val Lys Glu Gly Trp Leu Lys Lys Arg Gly
1               5                   10                  15

Lys Tyr Xaa Lys Thr Trp Arg Pro Arg Tyr Phe Leu Leu Lys Asn Asp
            20                  25                  30

Gly

<210> SEQ ID NO 2
<211> LENGTH: 14
<212> TYPE: PRT
<213> ORGANISM: Artificial Sequence
<220> FEATURE:
<223> OTHER INFORMATION: Synthetic peptide

<400> SEQUENCE: 2

Gly Arg Lys Lys Arg Arg Gln Arg Arg Arg Pro Pro Gln Gln
1               5                   10

<210> SEQ ID NO 3
<211> LENGTH: 9
<212> TYPE: PRT
<213> ORGANISM: Artificial Sequence
<220> FEATURE:

```
<223> OTHER INFORMATION: Synthetic peptide

<400> SEQUENCE: 3

Arg Arg Arg Arg Arg Arg Arg Arg
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic peptide

<400> SEQUENCE: 4

His His His His His His
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic peptide

<400> SEQUENCE: 5

Tyr Phe Leu Leu Lys
1               5

<210> SEQ ID NO 6
<211> LENGTH: 443
<212> TYPE: PRT
<213> ORGANISM: Unknown
<220> FEATURE:
<223> OTHER INFORMATION: Akt E17K variant polypeptide

<400> SEQUENCE: 6

Met Ser Asp Val Ala Ile Val Lys Glu Gly Trp Leu His Lys Arg Gly
1               5                   10                  15

Lys Tyr Ile Lys Thr Trp Arg Pro Arg Tyr Phe Leu Leu Lys Asn Asp
                20                  25                  30

Gly Thr Phe Ile Gly Tyr Lys Glu Arg Pro Gln Asp Val Asp Gln Arg
            35                  40                  45

Glu Ala Pro Leu Asn Asn Phe Ser Val Ala Gln Cys Gln Leu Met Lys
        50                  55                  60

Thr Glu Arg Pro Arg Pro Asn Thr Phe Ile Ile Arg Cys Leu Gln Trp
65                  70                  75                  80

Thr Thr Val Ile Glu Arg Thr Phe His Val Glu Thr Pro Glu Glu Arg
                85                  90                  95

Glu Glu Trp Thr Thr Ala Ile Gln Thr Val Ala Asp Gly Leu Lys Lys
            100                 105                 110

Gln Glu Glu Glu Glu Met Asp Phe Arg Ser Gly Ser Pro Ser Asp Asn
        115                 120                 125

Ser Gly Ala Glu Glu Met Glu Val Ser Leu Ala Lys Pro Lys His Arg
    130                 135                 140

Val Thr Met Asn Glu Phe Glu Tyr Leu Lys Leu Leu Gly Lys Gly Thr
145                 150                 155                 160

Phe Gly Lys Val Ile Leu Val Lys Glu Lys Ala Thr Gly Arg Tyr Tyr
                165                 170                 175

Ala Met Lys Ile Leu Lys Lys Glu Val Ile Val Ala Lys Asp Glu Val
            180                 185                 190
```

```
Ala His Thr Leu Thr Glu Asn Arg Val Leu Gln Asn Ser Arg His Pro
            195                 200                 205

Phe Leu Thr Ala Leu Lys Tyr Ser Phe Gln Thr His Asp Arg Leu Cys
    210                 215                 220

Phe Val Met Glu Tyr Ala Asn Gly Gly Glu Leu Phe Phe His Leu Ser
225                 230                 235                 240

Arg Glu Arg Val Phe Ser Glu Asp Arg Ala Arg Phe Tyr Gly Ala Glu
                245                 250                 255

Ile Val Ser Ala Leu Asp Tyr Leu His Ser Glu Lys Asn Val Val Tyr
            260                 265                 270

Arg Asp Leu Lys Leu Glu Asn Leu Met Leu Asp Lys Asp Gly His Ile
        275                 280                 285

Lys Ile Thr Asp Phe Gly Leu Cys Lys Glu Gly Ile Lys Asp Gly Ala
    290                 295                 300

Thr Met Lys Thr Phe Cys Gly Thr Pro Glu Tyr Leu Ala Pro Glu Val
305                 310                 315                 320

Leu Glu Asp Asn Asp Tyr Gly Arg Ala Val Asp Trp Trp Gly Leu Gly
                325                 330                 335

Val Val Met Tyr Glu Met Met Cys Gly Arg Leu Pro Phe Tyr Asn Gln
            340                 345                 350

Asp His Glu Lys Leu Phe Glu Leu Ile Leu Met Glu Glu Ile Arg Phe
        355                 360                 365

Pro Arg Thr Leu Gly Pro Glu Ala Lys Ser Leu Leu Ser Gly Leu Leu
    370                 375                 380

Lys Lys Asp Pro Lys Gln Arg Leu Gly Gly Gly Ser Glu Asp Ala Lys
385                 390                 395                 400

Glu Ile Met Gln His Arg Phe Phe Ala Gly Ile Val Trp Gln His Val
                405                 410                 415

Tyr Glu Lys Lys Leu Ser Pro Pro Phe Lys Pro Gln Val Thr Ser Glu
            420                 425                 430

Thr Asp Thr Arg Tyr Phe Asp Glu Glu Phe Thr
        435                 440

<210> SEQ ID NO 7
<211> LENGTH: 33
<212> TYPE: PRT
<213> ORGANISM: Unknown
<220> FEATURE:
<223> OTHER INFORMATION: Akt variant polypeptide

<400> SEQUENCE: 7

Met Ser Asp Val Ala Ile Val Lys Glu Gly Trp Leu Lys Lys Arg Gly
1               5                   10                  15

Lys Tyr Ile Lys Thr Trp Arg Pro Arg Tyr Phe Leu Leu Lys Asn Asp
            20                  25                  30

Gly

<210> SEQ ID NO 8
<211> LENGTH: 443
<212> TYPE: PRT
<213> ORGANISM: Unknown
<220> FEATURE:
<223> OTHER INFORMATION: wild-type Akt1 polypeptide

<400> SEQUENCE: 8

Met Ser Asp Val Ala Ile Val Lys Glu Gly Trp Leu His Lys Arg Gly
1               5                   10                  15
```

```
Glu Tyr Ile Lys Thr Trp Arg Pro Arg Tyr Phe Leu Leu Lys Asn Asp
             20                  25                  30

Gly Thr Phe Ile Gly Tyr Lys Glu Arg Pro Gln Asp Val Asp Gln Arg
         35                  40                  45

Glu Ala Pro Leu Asn Asn Phe Ser Val Ala Gln Cys Gln Leu Met Lys
50                  55                  60

Thr Glu Arg Pro Arg Pro Asn Thr Phe Ile Ile Arg Cys Leu Gln Trp
65                  70                  75                  80

Thr Thr Val Ile Glu Arg Thr Phe His Val Glu Thr Pro Glu Glu Arg
             85                  90                  95

Glu Glu Trp Thr Thr Ala Ile Gln Thr Val Ala Asp Gly Leu Lys Lys
            100                 105                 110

Gln Glu Glu Glu Glu Met Asp Phe Arg Ser Gly Ser Pro Ser Asp Asn
        115                 120                 125

Ser Gly Ala Glu Glu Met Glu Val Ser Leu Ala Lys Pro Lys His Arg
        130                 135                 140

Val Thr Met Asn Glu Phe Glu Tyr Leu Lys Leu Leu Gly Lys Gly Thr
145                 150                 155                 160

Phe Gly Lys Val Ile Leu Val Lys Glu Lys Ala Thr Gly Arg Tyr Tyr
                165                 170                 175

Ala Met Lys Ile Leu Lys Lys Glu Val Ile Val Ala Lys Asp Glu Val
            180                 185                 190

Ala His Thr Leu Thr Glu Asn Arg Val Leu Gln Asn Ser Arg His Pro
        195                 200                 205

Phe Leu Thr Ala Leu Lys Tyr Ser Phe Gln Thr His Asp Arg Leu Cys
210                 215                 220

Phe Val Met Glu Tyr Ala Asn Gly Gly Glu Leu Phe Phe His Leu Ser
225                 230                 235                 240

Arg Glu Arg Val Phe Ser Glu Asp Arg Ala Arg Phe Tyr Gly Ala Glu
                245                 250                 255

Ile Val Ser Ala Leu Asp Tyr Leu His Ser Glu Lys Asn Val Val Tyr
            260                 265                 270

Arg Asp Leu Lys Leu Glu Asn Leu Met Leu Asp Lys Asp Gly His Ile
        275                 280                 285

Lys Ile Thr Asp Phe Gly Leu Cys Lys Glu Gly Ile Lys Asp Gly Ala
290                 295                 300

Thr Met Lys Thr Phe Cys Gly Thr Pro Glu Tyr Leu Ala Pro Glu Val
305                 310                 315                 320

Leu Glu Asp Asn Asp Tyr Gly Arg Ala Val Asp Trp Trp Gly Leu Gly
                325                 330                 335

Val Val Met Tyr Glu Met Met Cys Gly Arg Leu Pro Phe Tyr Asn Gln
            340                 345                 350

Asp His Glu Lys Leu Phe Glu Leu Ile Leu Met Glu Glu Ile Arg Phe
        355                 360                 365

Pro Arg Thr Leu Gly Pro Glu Ala Lys Ser Leu Leu Ser Gly Leu Leu
370                 375                 380

Lys Lys Asp Pro Lys Gln Arg Leu Gly Gly Gly Ser Glu Asp Ala Lys
385                 390                 395                 400

Glu Ile Met Gln His Arg Phe Phe Ala Gly Ile Val Trp Gln His Val
                405                 410                 415

Tyr Glu Lys Lys Leu Ser Pro Pro Phe Lys Pro Gln Val Thr Ser Glu
            420                 425                 430

Thr Asp Thr Arg Tyr Phe Asp Glu Glu Phe Thr
```

```
                     435                 440

<210> SEQ ID NO 9
<211> LENGTH: 33
<212> TYPE: PRT
<213> ORGANISM: Unknown
<220> FEATURE:
<223> OTHER INFORMATION: wild-type Akt1 polypeptide

<400> SEQUENCE: 9

Met Ser Asp Val Ala Ile Val Lys Glu Gly Trp Leu Lys Lys Arg Gly
1               5                  10                  15

Glu Tyr Ile Lys Thr Trp Arg Pro Arg Tyr Phe Leu Leu Lys Asn Asp
            20                  25                  30

Gly

<210> SEQ ID NO 10
<211> LENGTH: 39
<212> TYPE: DNA
<213> ORGANISM: Artificial Sequence
<220> FEATURE:
<223> OTHER INFORMATION: Synthetic primer

<400> SEQUENCE: 10
agagaatcca tgtccgacgt cgcgatcgta aaggaaggg                          39

<210> SEQ ID NO 11
<211> LENGTH: 26
<212> TYPE: DNA
<213> ORGANISM: Artificial Sequence
<220> FEATURE:
<223> OTHER INFORMATION: Synthetic primer

<400> SEQUENCE: 11
tctgcggccg cttagtggtg atgatg                                        26

<210> SEQ ID NO 12
<211> LENGTH: 24
<212> TYPE: DNA
<213> ORGANISM: Artificial Sequence
<220> FEATURE:
<223> OTHER INFORMATION: Synthetic primer

<400> SEQUENCE: 12
aagatgggga tgagcgacgt ggct                                          24

<210> SEQ ID NO 13
<211> LENGTH: 25
<212> TYPE: DNA
<213> ORGANISM: Artificial Sequence
<220> FEATURE:
<223> OTHER INFORMATION: Synthetic primer

<400> SEQUENCE: 13
tccccgaccg gaagtccatc tcctc                                         25

<210> SEQ ID NO 14
<211> LENGTH: 6
<212> TYPE: PRT
<213> ORGANISM: Artificial Sequence
<220> FEATURE:
<223> OTHER INFORMATION: Synthetic peptide

<400> SEQUENCE: 14

Glu Gly Trp Leu His Lys
```

```
<210> SEQ ID NO 15
<211> LENGTH: 15
<212> TYPE: PRT
<213> ORGANISM: Artificial Sequence
<220> FEATURE:
<223> OTHER INFORMATION: Synthetic peptide

<400> SEQUENCE: 15

Glu Glu Trp Thr Thr Ala Ile Gln Thr Val Ala Asp Gly Leu Lys
1               5                   10                  15

<210> SEQ ID NO 16
<211> LENGTH: 16
<212> TYPE: PRT
<213> ORGANISM: Artificial Sequence
<220> FEATURE:
<223> OTHER INFORMATION: Synthetic peptide

<400> SEQUENCE: 16

Glu Ala Pro Leu Asn Asn Phe Ser Val Ala Gln Cys Gln Leu Met Lys
1               5                   10                  15

<210> SEQ ID NO 17
<211> LENGTH: 10
<212> TYPE: PRT
<213> ORGANISM: Human immunodeficiency virus

<400> SEQUENCE: 17

Tyr Gly Arg Lys Lys Arg Arg Gln Arg Arg
1               5                   10

<210> SEQ ID NO 18
<211> LENGTH: 7
<212> TYPE: PRT
<213> ORGANISM: Artificial Sequence
<220> FEATURE:
<223> OTHER INFORMATION: Synthetic peptide

<400> SEQUENCE: 18

Ala Leu Ala Pro Tyr Ile Pro
1               5

<210> SEQ ID NO 19
<211> LENGTH: 5
<212> TYPE: PRT
<213> ORGANISM: Artificial Sequence
<220> FEATURE:
<223> OTHER INFORMATION: Synthetic peptide

<400> SEQUENCE: 19

Gln Phe Leu Trp Glu
1               5

<210> SEQ ID NO 20
<211> LENGTH: 5
<212> TYPE: PRT
<213> ORGANISM: Artificial Sequence
<220> FEATURE:
<223> OTHER INFORMATION: Synthetic peptide

<400> SEQUENCE: 20

Tyr Pro Trp Val Glu
1               5
```

```
<210> SEQ ID NO 21
<211> LENGTH: 5
<212> TYPE: PRT
<213> ORGANISM: Artificial Sequence
<220> FEATURE:
<223> OTHER INFORMATION: Synthetic peptide

<400> SEQUENCE: 21

Gln Phe Lys Trp Glu
1               5

<210> SEQ ID NO 22
<211> LENGTH: 5
<212> TYPE: PRT
<213> ORGANISM: Artificial Sequence
<220> FEATURE:
<223> OTHER INFORMATION: Synthetic peptide

<400> SEQUENCE: 22

Ile Ser Glu Tyr Glu
1               5

<210> SEQ ID NO 23
<211> LENGTH: 4
<212> TYPE: PRT
<213> ORGANISM: Artificial Sequence
<220> FEATURE:
<223> OTHER INFORMATION: Synthetic peptide

<400> SEQUENCE: 23

Asn Leu Val Pro
1

<210> SEQ ID NO 24
<211> LENGTH: 5
<212> TYPE: PRT
<213> ORGANISM: Artificial Sequence
<220> FEATURE:
<223> OTHER INFORMATION: Synthetic peptide

<400> SEQUENCE: 24

Ala Leu Asn Ser Lys
1               5

<210> SEQ ID NO 25
<211> LENGTH: 5
<212> TYPE: PRT
<213> ORGANISM: Artificial Sequence
<220> FEATURE:
<223> OTHER INFORMATION: Synthetic peptide

<400> SEQUENCE: 25

Asn Arg Tyr Val Arg
1               5

<210> SEQ ID NO 26
<211> LENGTH: 5
<212> TYPE: PRT
<213> ORGANISM: Artificial Sequence
<220> FEATURE:
<223> OTHER INFORMATION: Synthetic peptide

<400> SEQUENCE: 26

Leu Leu Leu Leu Leu
1               5

<210> SEQ ID NO 27
```

```
<211> LENGTH: 4
<212> TYPE: PRT
<213> ORGANISM: Artificial Sequence
<220> FEATURE:
<223> OTHER INFORMATION: Synthetic peptide

<400> SEQUENCE: 27

Ala Leu Ala Phe
1

<210> SEQ ID NO 28
<211> LENGTH: 5
<212> TYPE: PRT
<213> ORGANISM: Artificial Sequence
<220> FEATURE:
<223> OTHER INFORMATION: Synthetic peptide

<400> SEQUENCE: 28

Tyr His Leu Phe Trp
1               5

<210> SEQ ID NO 29
<211> LENGTH: 5
<212> TYPE: PRT
<213> ORGANISM: Artificial Sequence
<220> FEATURE:
<223> OTHER INFORMATION: Synthetic peptide

<400> SEQUENCE: 29

Asn Val Tyr Pro Thr
1               5

<210> SEQ ID NO 30
<211> LENGTH: 4
<212> TYPE: PRT
<213> ORGANISM: Artificial Sequence
<220> FEATURE:
<223> OTHER INFORMATION: Synthetic peptide

<400> SEQUENCE: 30

Val Tyr Pro Thr
1

<210> SEQ ID NO 31
<211> LENGTH: 5
<212> TYPE: PRT
<213> ORGANISM: Artificial Sequence
<220> FEATURE:
<223> OTHER INFORMATION: Synthetic peptide

<400> SEQUENCE: 31

Asn His Trp Gly Ser
1               5

<210> SEQ ID NO 32
<211> LENGTH: 5
<212> TYPE: PRT
<213> ORGANISM: Artificial Sequence
<220> FEATURE:
<223> OTHER INFORMATION: Synthetic peptide

<400> SEQUENCE: 32

His Ala Arg His Gln
1               5

<210> SEQ ID NO 33
<211> LENGTH: 5
```

```
<212> TYPE: PRT
<213> ORGANISM: Artificial Sequence
<220> FEATURE:
<223> OTHER INFORMATION: Synthetic peptide

<400> SEQUENCE: 33

Asp His Trp Gly Ser
1               5

<210> SEQ ID NO 34
<211> LENGTH: 5
<212> TYPE: PRT
<213> ORGANISM: Artificial Sequence
<220> FEATURE:
<223> OTHER INFORMATION: Synthetic peptide

<400> SEQUENCE: 34

His Glu Trp Val Thr
1               5

<210> SEQ ID NO 35
<211> LENGTH: 5
<212> TYPE: PRT
<213> ORGANISM: Artificial Sequence
<220> FEATURE:
<223> OTHER INFORMATION: Synthetic peptide

<400> SEQUENCE: 35

Asn Gln Asp Thr Arg
1               5

<210> SEQ ID NO 36
<211> LENGTH: 5
<212> TYPE: PRT
<213> ORGANISM: Artificial Sequence
<220> FEATURE:
<223> OTHER INFORMATION: Synthetic peptide

<400> SEQUENCE: 36

Asp Gln Asn Thr Arg
1               5

<210> SEQ ID NO 37
<211> LENGTH: 5
<212> TYPE: PRT
<213> ORGANISM: Artificial Sequence
<220> FEATURE:
<223> OTHER INFORMATION: Synthetic peptide

<400> SEQUENCE: 37

Asp Gln Asp Thr Arg
1               5

<210> SEQ ID NO 38
<211> LENGTH: 5
<212> TYPE: PRT
<213> ORGANISM: Artificial Sequence
<220> FEATURE:
<223> OTHER INFORMATION: Synthetic peptide

<400> SEQUENCE: 38

Asp Asp Asp Asp Asp
1               5

<210> SEQ ID NO 39
<211> LENGTH: 5
<212> TYPE: PRT
```

```
<213> ORGANISM: Artificial Sequence
<220> FEATURE:
<223> OTHER INFORMATION: Synthetic peptide

<400> SEQUENCE: 39

His Phe Asn Lys His
1               5

<210> SEQ ID NO 40
<211> LENGTH: 5
<212> TYPE: PRT
<213> ORGANISM: Artificial Sequence
<220> FEATURE:
<223> OTHER INFORMATION: Synthetic peptide

<400> SEQUENCE: 40

His Phe Asp Lys His
1               5

<210> SEQ ID NO 41
<211> LENGTH: 5
<212> TYPE: PRT
<213> ORGANISM: Artificial Sequence
<220> FEATURE:
<223> OTHER INFORMATION: Synthetic peptide

<400> SEQUENCE: 41

Glu Leu Asn His Tyr
1               5

<210> SEQ ID NO 42
<211> LENGTH: 5
<212> TYPE: PRT
<213> ORGANISM: Artificial Sequence
<220> FEATURE:
<223> OTHER INFORMATION: Synthetic peptide

<400> SEQUENCE: 42

Asp Leu Leu Thr Phe
1               5

<210> SEQ ID NO 43
<211> LENGTH: 5
<212> TYPE: PRT
<213> ORGANISM: Artificial Sequence
<220> FEATURE:
<223> OTHER INFORMATION: Synthetic peptide

<400> SEQUENCE: 43

Tyr Leu Glu Ala Phe
1               5

<210> SEQ ID NO 44
<211> LENGTH: 5
<212> TYPE: PRT
<213> ORGANISM: Artificial Sequence
<220> FEATURE:
<223> OTHER INFORMATION: Synthetic peptide

<400> SEQUENCE: 44

Leu Phe His Gln Val
1               5

<210> SEQ ID NO 45
<211> LENGTH: 5
<212> TYPE: PRT
<213> ORGANISM: Artificial Sequence
```

```
<220> FEATURE:
<223> OTHER INFORMATION: Synthetic peptide

<400> SEQUENCE: 45

Tyr His Glu Trp Phe
1               5

<210> SEQ ID NO 46
<211> LENGTH: 5
<212> TYPE: PRT
<213> ORGANISM: Artificial Sequence
<220> FEATURE:
<223> OTHER INFORMATION: Synthetic peptide

<400> SEQUENCE: 46

Gly Gly Gly Gly Gly
1               5

<210> SEQ ID NO 47
<211> LENGTH: 5
<212> TYPE: PRT
<213> ORGANISM: Artificial Sequence
<220> FEATURE:
<223> OTHER INFORMATION: Synthetic peptide

<400> SEQUENCE: 47

Ala Lys Ala Phe Tyr
1               5

<210> SEQ ID NO 48
<211> LENGTH: 5
<212> TYPE: PRT
<213> ORGANISM: Artificial Sequence
<220> FEATURE:
<223> OTHER INFORMATION: Synthetic peptide

<400> SEQUENCE: 48

Gly Val Glu Lys Phe
1               5

<210> SEQ ID NO 49
<211> LENGTH: 5
<212> TYPE: PRT
<213> ORGANISM: Artificial Sequence
<220> FEATURE:
<223> OTHER INFORMATION: Synthetic peptide

<400> SEQUENCE: 49

Ala Arg Ser Asp Phe
1               5

<210> SEQ ID NO 50
<211> LENGTH: 5
<212> TYPE: PRT
<213> ORGANISM: Artificial Sequence
<220> FEATURE:
<223> OTHER INFORMATION: Synthetic peptide

<400> SEQUENCE: 50

Tyr Glu Ser Ser Gly
1               5

<210> SEQ ID NO 51
<211> LENGTH: 5
<212> TYPE: PRT
<213> ORGANISM: Artificial Sequence
<220> FEATURE:
```

<223> OTHER INFORMATION: Synthetic peptide

<400> SEQUENCE: 51

Glu Glu Pro Asn Phe
1               5

<210> SEQ ID NO 52
<211> LENGTH: 5
<212> TYPE: PRT
<213> ORGANISM: Artificial Sequence
<220> FEATURE:
<223> OTHER INFORMATION: Synthetic peptide

<400> SEQUENCE: 52

Tyr His Lys Phe Trp
1               5

<210> SEQ ID NO 53
<211> LENGTH: 4
<212> TYPE: PRT
<213> ORGANISM: Artificial Sequence
<220> FEATURE:
<223> OTHER INFORMATION: Synthetic peptide

<400> SEQUENCE: 53

Asn Trp Arg Leu
1

<210> SEQ ID NO 54
<211> LENGTH: 4
<212> TYPE: PRT
<213> ORGANISM: Artificial Sequence
<220> FEATURE:
<223> OTHER INFORMATION: Synthetic peptide

<400> SEQUENCE: 54

Asn Glu Arg Tyr
1

<210> SEQ ID NO 55
<211> LENGTH: 4
<212> TYPE: PRT
<213> ORGANISM: Artificial Sequence
<220> FEATURE:
<223> OTHER INFORMATION: Synthetic peptide

<400> SEQUENCE: 55

His Tyr Arg Trp
1

<210> SEQ ID NO 56
<211> LENGTH: 4
<212> TYPE: PRT
<213> ORGANISM: Artificial Sequence
<220> FEATURE:
<223> OTHER INFORMATION: Synthetic peptide

<400> SEQUENCE: 56

Tyr Trp Lys Gly
1

<210> SEQ ID NO 57
<211> LENGTH: 4
<212> TYPE: PRT
<213> ORGANISM: Artificial Sequence
<220> FEATURE:
<223> OTHER INFORMATION: Synthetic peptide

<400> SEQUENCE: 57

Tyr Trp Arg Leu
1

<210> SEQ ID NO 58
<211> LENGTH: 4
<212> TYPE: PRT
<213> ORGANISM: Artificial Sequence
<220> FEATURE:
<223> OTHER INFORMATION: Synthetic peptide

<400> SEQUENCE: 58

Trp Phe Arg Ile
1

<210> SEQ ID NO 59
<211> LENGTH: 4
<212> TYPE: PRT
<213> ORGANISM: Artificial Sequence
<220> FEATURE:
<223> OTHER INFORMATION: Synthetic peptide

<400> SEQUENCE: 59

Asn Val Tyr Leu
1

<210> SEQ ID NO 60
<211> LENGTH: 4
<212> TYPE: PRT
<213> ORGANISM: Artificial Sequence
<220> FEATURE:
<223> OTHER INFORMATION: Synthetic peptide

<400> SEQUENCE: 60

Ala Ala Arg Trp
1

<210> SEQ ID NO 61
<211> LENGTH: 4
<212> TYPE: PRT
<213> ORGANISM: Artificial Sequence
<220> FEATURE:
<223> OTHER INFORMATION: Synthetic peptide

<400> SEQUENCE: 61

His Trp Pro Arg
1

<210> SEQ ID NO 62
<211> LENGTH: 4
<212> TYPE: PRT
<213> ORGANISM: Artificial Sequence
<220> FEATURE:
<223> OTHER INFORMATION: Synthetic peptide

<400> SEQUENCE: 62

Leu Leu Leu Leu
1

<210> SEQ ID NO 63
<211> LENGTH: 4
<212> TYPE: PRT
<213> ORGANISM: Artificial Sequence
<220> FEATURE:
<223> OTHER INFORMATION: Synthetic peptide

```
<400> SEQUENCE: 63

Ala Tyr Leu Tyr
1

<210> SEQ ID NO 64
<211> LENGTH: 4
<212> TYPE: PRT
<213> ORGANISM: Artificial Sequence
<220> FEATURE:
<223> OTHER INFORMATION: Synthetic peptide

<400> SEQUENCE: 64

Asp Trp Trp Arg
1

<210> SEQ ID NO 65
<211> LENGTH: 4
<212> TYPE: PRT
<213> ORGANISM: Artificial Sequence
<220> FEATURE:
<223> OTHER INFORMATION: Synthetic peptide

<400> SEQUENCE: 65

Arg Pro Tyr Tyr
1

<210> SEQ ID NO 66
<211> LENGTH: 4
<212> TYPE: PRT
<213> ORGANISM: Artificial Sequence
<220> FEATURE:
<223> OTHER INFORMATION: Synthetic peptide

<400> SEQUENCE: 66

Arg His Trp Ser
1

<210> SEQ ID NO 67
<211> LENGTH: 4
<212> TYPE: PRT
<213> ORGANISM: Artificial Sequence
<220> FEATURE:
<223> OTHER INFORMATION: Synthetic peptide

<400> SEQUENCE: 67

Gly Gly Gly Gly
1

<210> SEQ ID NO 68
<211> LENGTH: 4
<212> TYPE: PRT
<213> ORGANISM: Artificial Sequence
<220> FEATURE:
<223> OTHER INFORMATION: Synthetic peptide

<400> SEQUENCE: 68

Arg Arg Arg Arg
1

<210> SEQ ID NO 69
<211> LENGTH: 4
<212> TYPE: PRT
<213> ORGANISM: Artificial Sequence
<220> FEATURE:
<223> OTHER INFORMATION: Synthetic peptide

<400> SEQUENCE: 69
```

Asp Asp Asp Asp
1

<210> SEQ ID NO 70
<211> LENGTH: 4
<212> TYPE: PRT
<213> ORGANISM: Artificial Sequence
<220> FEATURE:
<223> OTHER INFORMATION: Synthetic peptide

<400> SEQUENCE: 70

Val Trp Phe Arg
1

<210> SEQ ID NO 71
<211> LENGTH: 4
<212> TYPE: PRT
<213> ORGANISM: Artificial Sequence
<220> FEATURE:
<223> OTHER INFORMATION: Synthetic peptide

<400> SEQUENCE: 71

Tyr Tyr Ser Arg
1

<210> SEQ ID NO 72
<211> LENGTH: 4
<212> TYPE: PRT
<213> ORGANISM: Artificial Sequence
<220> FEATURE:
<223> OTHER INFORMATION: Synthetic peptide

<400> SEQUENCE: 72

Gly Arg Trp Tyr
1

<210> SEQ ID NO 73
<211> LENGTH: 4
<212> TYPE: PRT
<213> ORGANISM: Artificial Sequence
<220> FEATURE:
<223> OTHER INFORMATION: Synthetic peptide

<400> SEQUENCE: 73

Ser Arg Phe Tyr
1

<210> SEQ ID NO 74
<211> LENGTH: 4
<212> TYPE: PRT
<213> ORGANISM: Artificial Sequence
<220> FEATURE:
<223> OTHER INFORMATION: Synthetic peptide

<400> SEQUENCE: 74

Tyr Asn Tyr Lys
1

<210> SEQ ID NO 75
<211> LENGTH: 4
<212> TYPE: PRT
<213> ORGANISM: Artificial Sequence
<220> FEATURE:
<223> OTHER INFORMATION: Synthetic peptide

<400> SEQUENCE: 75

Arg Asp Tyr Arg
1

<210> SEQ ID NO 76
<211> LENGTH: 4
<212> TYPE: PRT
<213> ORGANISM: Artificial Sequence
<220> FEATURE:
<223> OTHER INFORMATION: Synthetic peptide

<400> SEQUENCE: 76

Tyr Lys Ser Tyr
1

<210> SEQ ID NO 77
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 77

Glu Glu Phe Glu Phe
1               5

<210> SEQ ID NO 78
<211> LENGTH: 5
<212> TYPE: PRT
<213> ORGANISM: Artificial Sequence
<220> FEATURE:
<223> OTHER INFORMATION: Synthetic peptide

<400> SEQUENCE: 78

Ile Val Asp Ala Glu
1               5

<210> SEQ ID NO 79
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa is Leu or Lys

<400> SEQUENCE: 79

Pro His Trp Xaa Phe
1               5

<210> SEQ ID NO 80
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is Leu or Lys

<400> SEQUENCE: 80

Phe Xaa Gly Thr
1

<210> SEQ ID NO 81
<211> LENGTH: 4

```
<212> TYPE: PRT
<213> ORGANISM: Artificial Sequence
<220> FEATURE:
<223> OTHER INFORMATION: Synthetic peptide

<400> SEQUENCE: 81

Phe Glu Ile Gln
1

<210> SEQ ID NO 82
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa is Asp or Asn

<400> SEQUENCE: 82

Glu Glu Pro Xaa Phe
1               5

<210> SEQ ID NO 83
<211> LENGTH: 5
<212> TYPE: PRT
<213> ORGANISM: Artificial Sequence
<220> FEATURE:
<223> OTHER INFORMATION: Synthetic peptide

<400> SEQUENCE: 83

Phe Glu Glu Ala Ile
1               5

<210> SEQ ID NO 84
<211> LENGTH: 5
<212> TYPE: PRT
<213> ORGANISM: Artificial Sequence
<220> FEATURE:
<223> OTHER INFORMATION: Synthetic peptide

<400> SEQUENCE: 84

Asn Trp Tyr Ala Trp
1               5

<210> SEQ ID NO 85
<211> LENGTH: 5
<212> TYPE: PRT
<213> ORGANISM: Artificial Sequence
<220> FEATURE:
<223> OTHER INFORMATION: Synthetic peptide

<400> SEQUENCE: 85

Asn Leu Val Pro Asn
1               5

<210> SEQ ID NO 86
<211> LENGTH: 4
<212> TYPE: PRT
<213> ORGANISM: Artificial Sequence
<220> FEATURE:
<223> OTHER INFORMATION: Synthetic peptide

<400> SEQUENCE: 86

Arg Arg Arg Phe
1
```

```
<210> SEQ ID NO 87
<211> LENGTH: 4
<212> TYPE: PRT
<213> ORGANISM: Artificial Sequence
<220> FEATURE:
<223> OTHER INFORMATION: Synthetic peptide

<400> SEQUENCE: 87

Pro Ala Tyr Asn
1

<210> SEQ ID NO 88
<211> LENGTH: 4
<212> TYPE: PRT
<213> ORGANISM: Artificial Sequence
<220> FEATURE:
<223> OTHER INFORMATION: Synthetic peptide

<400> SEQUENCE: 88

Tyr Lys Thr Trp
1

<210> SEQ ID NO 89
<211> LENGTH: 4
<212> TYPE: PRT
<213> ORGANISM: Artificial Sequence
<220> FEATURE:
<223> OTHER INFORMATION: Synthetic peptide

<400> SEQUENCE: 89

Pro Trp Trp Arg
1

<210> SEQ ID NO 90
<211> LENGTH: 4
<212> TYPE: PRT
<213> ORGANISM: Artificial Sequence
<220> FEATURE:
<223> OTHER INFORMATION: Synthetic peptide

<400> SEQUENCE: 90

Asn Phe Arg Tyr
1

<210> SEQ ID NO 91
<211> LENGTH: 4
<212> TYPE: PRT
<213> ORGANISM: Artificial Sequence
<220> FEATURE:
<223> OTHER INFORMATION: Synthetic peptide

<400> SEQUENCE: 91

His Trp Arg Trp
1

<210> SEQ ID NO 92
<211> LENGTH: 5
<212> TYPE: PRT
<213> ORGANISM: Artificial Sequence
<220> FEATURE:
<223> OTHER INFORMATION: Synthetic peptide

<400> SEQUENCE: 92

Ile Arg Tyr Arg Asn
1               5
```

```
<210> SEQ ID NO 93
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 93

Ala Leu Ala Pro Tyr Ile Pro
1               5
```